(12) United States Patent
Nolling et al.

(10) Patent No.: US 9,376,711 B2
(45) Date of Patent: Jun. 28, 2016

(54) MULTIMODAL METHODS FOR SIMULTANEOUS DETECTION AND QUANTIFICATION OF MULTIPLE NUCLEIC ACIDS IN A SAMPLE

(71) Applicant: PrimeraDx, Inc., Mansfield, MA (US)

(72) Inventors: Jork Nolling, Hopedale, MA (US); Vincent Miles, Chestnut Hill, MA (US)

(73) Assignee: QIAGEN MANSFIELD, INC., Mansfield, MA (US)

( * ) Notice: Subject to any disclaimer, the term of this patent is extended or adjusted under 35 U.S.C. 154(b) by 0 days.

(21) Appl. No.: 14/153,550

(22) Filed: Jan. 13, 2014

(65) Prior Publication Data

US 2014/0302496 A1   Oct. 9, 2014

Related U.S. Application Data

(63) Continuation of application No. PCT/US2012/046656, filed on Jul. 13, 2012.

(60) Provisional application No. 61/507,382, filed on Jul. 13, 2011.

(51) Int. Cl.
*C12Q 1/68* (2006.01)

(52) U.S. Cl.
CPC .............. *C12Q 1/6813* (2013.01); *C12Q 1/686* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 5,582,989 A | 12/1996 | Caskey et al. | |
| 5,876,924 A | 3/1999 | Zhang et al. | |
| 5,942,391 A | 8/1999 | Zhang et al. | |
| 6,368,801 B1 | 4/2002 | Faruqi | |
| 6,428,963 B2 | 8/2002 | Danenberg et al. | |
| 6,569,647 B1 | 5/2003 | Zhang et al. | |
| 6,593,086 B2 | 7/2003 | Zhang | |
| 6,610,488 B2 | 8/2003 | Danenberg et al. | |
| 6,613,518 B2 | 9/2003 | Danenberg et al. | |
| RE38,442 E | 2/2004 | Zhang et al. | |
| 6,783,943 B2 | 8/2004 | Christian et al. | |
| 6,855,523 B2 | 2/2005 | Zhang et al. | |
| 7,101,663 B2 | 9/2006 | Godfrey et al. | |
| 7,361,489 B2 | 4/2008 | Zhang et al. | |
| 7,364,858 B2 | 4/2008 | Barany et al. | |
| 7,429,453 B2 | 9/2008 | Barany et al. | |
| 7,445,893 B2 * | 11/2008 | Slepnev ............... | C12Q 1/6851 435/6.1 |
| 7,455,965 B2 | 11/2008 | Barany et al. | |
| 7,494,791 B2 | 2/2009 | Goel | |
| 7,556,924 B2 | 7/2009 | Barany et al. | |
| 7,767,391 B2 | 8/2010 | Scott et al. | |
| 7,803,550 B2 | 9/2010 | Makarov et al. | |
| 7,858,304 B2 | 12/2010 | Baker et al. | |
| 7,862,999 B2 | 1/2011 | Zheng et al. | |
| 7,879,555 B2 | 2/2011 | Erlander et al. | |
| 7,893,233 B2 | 2/2011 | Barany et al. | |
| 8,551,708 B2 * | 10/2013 | Bernitz ................ | C12Q 1/6809 435/6.12 |
| 2002/0160404 A1 | 10/2002 | Dietmaier et al. | |
| 2002/0177142 A1 | 11/2002 | Christian et al. | |
| 2002/0182598 A1 | 12/2002 | Zhang | |
| 2003/0017482 A1 | 1/2003 | Godfrey et al. | |
| 2003/0017491 A1 | 1/2003 | Shi et al. | |
| 2003/0032016 A1 | 2/2003 | Barany et al. | |
| 2003/0175706 A1 | 9/2003 | Zhang | |
| 2003/0180758 A1 | 9/2003 | Bacher | |
| 2003/0190604 A1 | 10/2003 | Zhang et al. | |
| 2004/0009475 A1 | 1/2004 | Danenberg | |
| 2004/0072305 A1 | 4/2004 | Erlander et al. | |
| 2004/0137484 A1 | 7/2004 | Zhang et al. | |
| 2004/0137489 A1 | 7/2004 | Shaughnessy | |
| 2004/0167086 A1 | 8/2004 | Heiskala | |
| 2004/0203061 A1 | 10/2004 | Barany et al. | |
| 2004/0214224 A1 | 10/2004 | Barany et al. | |
| 2004/0259105 A1 | 12/2004 | Fan et al. | |
| 2005/0009047 A1 | 1/2005 | Erlander et al. | |
| 2005/0032109 A1 | 2/2005 | Roemisch et al. | |
| 2005/0095634 A1 | 5/2005 | Baker et al. | |
| 2005/0196782 A1 | 9/2005 | Kiefer et al. | |
| 2005/0196792 A1 | 9/2005 | Fodor et al. | |
| 2005/0202473 A1 | 9/2005 | Bacher et al. | |
| 2005/0239101 A1 | 10/2005 | Sukumar et al. | |
| 2006/0024731 A1 | 2/2006 | Barany et al. | |
| 2006/0035240 A1 * | 2/2006 | Seul et al. ............ | 435/6 |
| 2006/0063170 A1 | 3/2006 | Erlander et al. | |

(Continued)

FOREIGN PATENT DOCUMENTS

| | | |
|---|---|---|
| WO | 98/04745 A1 | 2/1998 |
| WO | 98/04746 A1 | 2/1998 |
| WO | 00/06780 | 2/2000 |
| WO | 02/44339 A2 | 6/2002 |
| WO | 02/50310 A2 | 6/2002 |
| WO | 03/033722 A2 | 4/2003 |
| WO | 2004/033728 A2 | 4/2004 |
| WO | 2005/040396 A2 | 5/2005 |
| WO | 2005/042713 A2 | 5/2005 |
| WO | 2005/060725 A2 | 7/2005 |
| WO | 2005/061722 A1 | 7/2005 |

(Continued)

*Primary Examiner* — Prabha Chunduru
(74) *Attorney, Agent, or Firm* — Nixon Peabody LLP; Mark J. FitzGerald

(57) ABSTRACT

Described herein are approaches for the detection, identification, and/or quantification of target nucleic acids, including, but not limited to partially, substantially randomly, degraded target nucleic acids, in a biological sample, such as a formalin-fixed, paraffin-embedded (FFPE) sample. These approaches provide a means of detecting, identifying, and/or quantifying target nucleic acid molecules, including DNA and RNA molecules, further including RNAs of different classes, from the same sample, and in the same reaction, by using "expander oligonucleotides," as the term is defined herein, to convert fragments of target nucleic acids into discretely sized DNA fragments, each with a chosen length characteristic for the target nucleic acid from which it is derived.

10 Claims, 14 Drawing Sheets

(56) References Cited

U.S. PATENT DOCUMENTS

| | | |
|---|---|---|
| 2006/0078894 A1 | 4/2006 | Winkler et al. |
| 2006/0078925 A1 | 4/2006 | Mourelatos et al. |
| 2006/0172316 A1 | 8/2006 | Anderson et al. |
| 2006/0199197 A1 | 9/2006 | Danenberg et al. |
| 2006/0205006 A1 | 9/2006 | Godfrey et al. |
| 2006/0216724 A1 | 9/2006 | Christian et al. |
| 2006/0223075 A1 | 10/2006 | Davis et al. |
| 2006/0240451 A1 | 10/2006 | Jendrisak et al. |
| 2006/0281108 A1 | 12/2006 | Monforte et al. |
| 2006/0286579 A1 | 12/2006 | Erlander et al. |
| 2006/0292585 A1 | 12/2006 | Nautiyal et al. |
| 2007/0003953 A1 | 1/2007 | Palaniappan et al. |
| 2007/0015187 A1 | 1/2007 | Lao et al. |
| 2007/0031857 A1 | 2/2007 | Makarov et al. |
| 2007/0031858 A1 | 2/2007 | Makarov et al. |
| 2007/0037137 A1 | 2/2007 | Gyllensten et al. |
| 2007/0042419 A1 | 2/2007 | Barany et al. |
| 2007/0048759 A1 | 3/2007 | Luo et al. |
| 2007/0048783 A1 | 3/2007 | Barany et al. |
| 2007/0054305 A1 | 3/2007 | Barany et al. |
| 2007/0054306 A1 | 3/2007 | Barany et al. |
| 2007/0059685 A1 | 3/2007 | Kohne |
| 2007/0059737 A1 | 3/2007 | Baker et al. |
| 2007/0065844 A1 | 3/2007 | Golub et al. |
| 2007/0092883 A1 | 4/2007 | Schouten et al. |
| 2007/0128628 A1 | 6/2007 | Krupp et al. |
| 2007/0141589 A1 | 6/2007 | Baker et al. |
| 2007/0161020 A1 | 7/2007 | Luo et al. |
| 2007/0190540 A1 | 8/2007 | Stanley |
| 2007/0212695 A1* | 9/2007 | Aivazachvili ........ C12Q 1/6827 435/6.12 |
| 2007/0231803 A1 | 10/2007 | Jensen |
| 2007/0254305 A1 | 11/2007 | Paik et al. |
| 2007/0269799 A9 | 11/2007 | Zhang |
| 2007/0275925 A1 | 11/2007 | Woodruff et al. |
| 2008/0050746 A1 | 2/2008 | McMaster et al. |
| 2008/0085515 A1 | 4/2008 | Remacle et al. |
| 2008/0131878 A1 | 6/2008 | Latham et al. |
| 2008/0182255 A1 | 7/2008 | Baker et al. |
| 2008/0199916 A1 | 8/2008 | Zheng et al. |
| 2008/0233563 A1 | 9/2008 | Mitas et al. |
| 2008/0241831 A1* | 10/2008 | Fan et al. ........................ 435/6 |
| 2008/0261217 A1 | 10/2008 | Melnikov et al. |
| 2009/0029346 A1 | 1/2009 | Millar et al. |
| 2009/0042192 A1 | 2/2009 | Kiefer et al. |
| 2009/0075258 A1 | 3/2009 | Latham et al. |
| 2009/0092979 A1 | 4/2009 | Danenberg |
| 2009/0203015 A1 | 8/2009 | Chang et al. |
| 2010/0092963 A1 | 4/2010 | Ju |
| 2010/0129792 A1 | 5/2010 | Makrigiorgos |
| 2010/0129822 A1 | 5/2010 | Siva et al. |
| 2010/0173311 A1 | 7/2010 | Grow et al. |
| 2010/0190167 A1 | 7/2010 | Getts et al. |
| 2010/0197511 A1 | 8/2010 | Erlander et al. |
| 2010/0203532 A1 | 8/2010 | Makrigiorgos |
| 2010/0203538 A1 | 8/2010 | Dube et al. |
| 2010/0209920 A1 | 8/2010 | Baker et al. |
| 2011/0136116 A1 | 6/2011 | Barany et al. |

FOREIGN PATENT DOCUMENTS

| | | |
|---|---|---|
| WO | 2006/042303 A2 | 4/2006 |
| WO | 2006/086668 A2 | 8/2006 |
| WO | 2006/087559 A1 | 8/2006 |
| WO | 2006/119439 A2 | 11/2006 |
| WO | 2006/127860 A2 | 11/2006 |
| WO | 2006/135904 A2 | 12/2006 |
| WO | 2007/005482 A1 | 1/2007 |
| WO | 2007/018601 A1 | 2/2007 |
| WO | 2007/025340 A1 | 3/2007 |
| WO | 2007/058898 A2 | 5/2007 |
| WO | 2007/106507 A2 | 9/2007 |
| WO | 2007/106802 A2 | 9/2007 |
| WO | 2007/127458 A2 | 12/2007 |
| WO | 2008/070675 A2 | 6/2008 |
| WO | 2008/079987 A2 | 7/2008 |
| WO | 2008/150937 A2 | 12/2008 |
| WO | 2009/017784 A2 | 2/2009 |
| WO | 2010/045462 A1 | 4/2010 |
| WO | 2010/065626 A1 | 6/2010 |
| WO | 2010/068473 A1 | 6/2010 |
| WO | 2010/088288 A2 | 8/2010 |
| WO | 2010/088517 A1 | 8/2010 |
| WO | 2010/111682 A2 | 9/2010 |
| WO | 2011/019964 A1 | 2/2011 |

\* cited by examiner

SEQUENCE LISTING

<160> NUMBER OF SEQ ID NOS: 71

<210> SEQ ID NO 1
<211> LENGTH: 16
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 1
ggcagagatg atgacc                                                        16

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccttttattt ccccagc                                                       17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acaaaggcag atggatc                                                       17

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actcaggccc atttcc                                                        16

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagttgaagg tagtttcg                                                      18

<210> SEQ ID NO 6
<211> LENGTH: 106
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtggttgga gctgtctcag tcttcatata aatttttata aattttatta tttttaataa        60
ataatatttt taaatataaa agtccactgg cgtcttcacc accatg                      106

<210> SEQ ID NO 7
<211> LENGTH: 56
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
aagcgtgcac ttacctagtg tgctgatata cgtggttgga gagctcattt ggaatt          56

<210> SEQ ID NO 8
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcacctatc gagcctactc tacgcatata aatttttata aattttatta tttttaataa     60
ataatatttt taaatacgga ttacaccttc ccacttgctg                          100

<210> SEQ ID NO 9
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagcgtgcac ttacctagtg tgctgatata aatttttata aattttatta tttttaatcc     60
aactgctttc atttgtgagg gatctga                                         87

<210> SEQ ID NO 10
<211> LENGTH: 137
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
actgttggaa ctccactggt gagagatata aatttttata aattttatta tttttaataa     60
ataatatttt taaatataaa aattaatatt tatataaatt taaattataa aagaggcact    120
cttccagcct tccttcc                                                   137

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agtggttgga gctgtctcag tcttc                                           25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
aagcgtgcac ttacctagtg tgctg                                         25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcacctatc gagcctactc tacgc                                         25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagcgtgcac ttacctagtg tgctg                                         25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actgttggaa ctccactggt gagag                                         25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aggcagagat gatgaccctt ttggct                                        26

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17 ccttttatt ccccagcact ctcgtcg                                        27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acaaaggcag atggatcagc caagaag                                       27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
actcaggccc atttccttta tgtctgc                                            27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agagttgaag gtagtttcgt ggatgcca                                           28

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagtcgcact aaaagc                                                        16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccagtacctg gcgaag                                                        16

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gttggggttc agtacag                                                       17

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctaactagaa cttgttactt aactatac                                           28

```
<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctaactagaa cttgttactt attataacca cac                                    33

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atagacgagt ctcaacacag acgcgatata aatgtggatt ggagaaagaa aggctacgtg       60

<210> SEQ ID NO 27
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
agtggttgga gctgtctcag tcttcatata aatttttata aatttttatta tttttaataa      60 ataatatttt taaatatagc gatgtgacgc cactcacctt tac                        103

<210> SEQ ID NO 28
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
taccagtctg tgtcgaacag cgatcatata aatttttata aatttattta tttttaataa      60
ataatatttt taaatataaa aattaatatt tatataaatt tccacctcca agcccagatt     120
caga                                                                  124

<210> SEQ ID NO 29
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
actgttggaa ctccactggt gagagatata aatttttata aatttttatta tttttaataa      60 ataatatttt taaattgagg tagtaggttg                                        90

<210> SEQ ID NO 30
<211> LENGTH: 54
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 30
gcgctcctga gtctctaact accacataaa tctgtggatt agagacctag gaca         54

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atagacgagt ctcaacacag acgcg                                          25

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cagtcgcact aaaagcccaa caagaac                                        27

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agtggttgga gctgtctcag tcttc                                          25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccagtacctg gcgaagtcga tcatg                                          25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
taccagtctg tgtcgaacag cgatc                                          25

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
agttggggtt cagtacagag atgccc                                          26

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
actgttggaa ctccactggt gagag                                           25

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acacaacggc gtctaactag aacttgttac tt                                   32

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcgctcctga gtctctaact accac                                           25

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ataaaaatta tgcctgggag acatgagtga cagaa                                35

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttgctcagct tgtactcagg gctc                                            24

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ataaaaatta agcactacac aggccacttc ct        32

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ataaaaatta tgatgttgcc agcactgagt cattatc        37

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ataaaaatta gatcgcacca gtgcattgat atctgt        36

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ataaaaatta atatttaaag cctccctgga tctccatatc ct        42

<210> SEQ ID NO 46
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ataaaattaa tatttatata agcctccctg gatctccata tcct        44

<210> SEQ ID NO 47
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ataaaaatta atatttatac aagtggacca tattctatcg gcaa        44

<210> SEQ ID NO 48
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 48
ccaccgcctt caagtttaac gacacatata aatttttata aatttttatta ttttttaataa      60 ataatatttg gaagttctgg agtttgtcac                                         90

<210> SEQ ID NO 49
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acctcgctgg tagacctcgt ctaacatata aatttttata aatttttatta ttttttaataa      60 ataatatttt taaataatct ttctccggca tcatgattgt                             100

<210> SEQ ID NO 50
<211> LENGTH: 97
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttgcaccgca ccacatacta gtacgatata aatttttata aatttttatta ttttttaataa      60 ataatatttt taaggacatt gattggacga catatac                                 97

<210> SEQ ID NO 51
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agccttgcgg tacggttagt gtttcatata aatttttata aatttttatta ttttttaataa      60 ataataacac ctgggaaagg accta                                              85

<210> SEQ ID NO 52
<211> LENGTH: 92
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agccttgcgg tacggttagt gtttcatata aatttttata aatttttatta ttttttaataa      60 ataataactc gggagactat gaaatattgt ac                                      92

<210> SEQ ID NO 53
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agccttgcgg tacggttagt gtttcatata cataaagatg tcatcatcaa ccaagtg           57
```

<210> SEQ ID NO 54
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agccttgcgg tacggttagt gtttcatata aatttttata aatttttatta tttttgtcaa    60 ctcgcgaaaa aaacag                                                     76

<210> SEQ ID NO 55
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agccttgcgg tacggttagt gtttcatata aatttttata aattaatgat ggcttccaaa    60
tagaagtac                                                             69

<210> SEQ ID NO 56
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agccttgcgg tacggttagt gtttcatata aatttgacag aaaaataatt ctgtgggatc    60
a                                                                     61

<210> SEQ ID NO 57
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agccttgcgg tacggttagt gtttcatata aatttgacag aaaaataatt ctgtgggatc    60
a                                                                     61

<210> SEQ ID NO 58
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agccttgcgg tacggttagt gtttcatata actcagtgaa aaaatcagtc tcaagtaa      58

<210> SEQ ID NO 59
<211> LENGTH: 92
<212> TYPE: DNA
<213> ORGANISM: Artificial Sequence
<220> FEATURE:

<223> OTHER INFORMATION: Description of Artificial Sequence: Synthetic
       primer

<400> SEQUENCE: 59
ccaccgcctt caagtttaac gacacatata aattttata aatttttatta tttttaataa      60 ataatatttg ccatcatttt ggagaggatt ga                                    92

<210> SEQ ID NO 60
<211> LENGTH: 16
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 60
ttgctcagct tgtact                                                      16

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 61
tgatgttgcc agcac                                                       15

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 62
gatcgcacca gtgca                                                       15

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 63
aagcctccct ggatc                                                       15

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 64
acaagtggac catattct                                                    18

<210> SEQ ID NO 65
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 65
agccttgcgg tacggttagt gtttc                                               25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acctcgctgg tagacctcgt ctaac                                               25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccaccgcctt caagtttaac gacac                                               25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttgcaccgca ccacatacta gtacg                                               25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agccttgcgg tacggttagt gtttc                                               25

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccaccgcctt caagtttaac gacac                                               25

<210> SEQ ID NO 71
<211> LENGTH: 25
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 71
ttgcaccgca ccacatacta gtacg                                              25
```

MULTIMODAL METHODS FOR SIMULTANEOUS DETECTION AND QUANTIFICATION OF MULTIPLE NUCLEIC ACIDS IN A SAMPLE

CROSS-REFERENCE TO RELATED APPLICATIONS

This application is a continuation application of International Application No. PCT/US12/46656 filed on Jul. 13, 2012, which claims the benefit under 35 U.S.C. §119(e) of U.S. Provisional Patent Application Ser. No. 61/507,382 filed on Jul. 13, 2011, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 13, 2012, is named 20120713_SequenceListing-TextFile_046264_068701_PCT.txt and is 17,878 bytes in size.

FIELD OF THE INVENTION

The invention generally relates to methods for the detection, identification, and/or quantification of target nucleic acids in a sample.

BACKGROUND

Formalin-fixed archival tissues represent an invaluable resource for genetic and gene expression analysis, as they are the most widely available materials for studies of human disease. Tissue samples collected during medical procedures, such as surgery and biopsies, are often fixed in formalin, followed by embedding in paraffin for long-term preservation and archival storage. It is estimated that there were over 300 million of these formalin-fixed, paraffin-embedded (FFPE) samples archived in North America for cancer alone in 1999, with more samples accumulating at a rate of over 20 million per year. Many of these samples represent clinical outcomes with the potential to provide critical insight into expression profiles of biomarkers associated with the development of complex diseases. However, FFPE archival samples are considered poor material for PCR analytical applications due to chemical modification and cross-linking of, as well as substantial degradation of, nucleic acids. Targeting RNA extracted from FFPE specimens is a particular challenge since degradation can result in an average template size well below 200 nucleotides, and loss of poly-A tracts.

SUMMARY OF THE INVENTION

Described herein are approaches for the detection, identification, and/or quantification of target nucleic acids, including, but not limited to partially, substantially randomly, degraded target nucleic acids, in a biological sample, such as a formalin-fixed, paraffin-embedded (FFPE) sample. These approaches provide a means of detecting, identifying, and/or quantifying target nucleic acid molecules, including DNA and RNA molecules, further including RNAs of different classes, from the same sample, and in the same reaction, by using "expander oligonucleotides," as the term is defined herein, to convert fragments of target nucleic acids into discretely sized DNA fragments, each with a chosen length characteristic for the target nucleic acid from which it is derived.

Thus, provided by the methods, compositions, and kits comprising expander oligonucleotides described herein is the ability to detect nucleic acids of more than one chemical structure, i.e., DNA and RNA, and/or multiple classes of nucleic acids, simultaneously within the same reaction. Further, these methods, compositions, and kits comprising expander oligonucleotides can be used to detect nucleic acids of more than one chemical structure, i.e., DNA and RNA, and/or multiple classes of nucleic acids, isolated or obtained from samples that have undergone partial degradation.

In some embodiments of these approaches, each expander oligonucleotide is substantially identical in sequence along much of its length to a sequence within a specific target nucleic acid, and is referred to as a "splint molecule," which is further defined herein below. In other embodiments of these aspects, the expander oligonucleotide has only a short stretch at one end that is substantially identical in sequence to a sequence within a specific target nucleic acid, and is referred to herein as a "prosthetic molecule," which is further defined herein below. The approaches described herein provide the advantage of not only permitting the specific detection and quantification of an individual species of a target nucleic acid in a nucleic acid sample, but also provide multiplex approaches that permit determination of the presence of and/or amounts of a plurality of target nucleic acids in a single reaction, including determination of the presence and/or amount of nucleic acids of different type or chemical structure (e.g., DNA, RNA) and/or different class (e.g., mRNA, miRNA, etc.) in a single reaction mixture.

Accordingly, described herein, in part, are novel approaches for the detection and quantification of a plurality of target nucleic acid sequences based on using expander oligonucleotides of particular design, each specific for one of the target nucleic acids being detected and, in some embodiments, different in length from each of the expander oligonucleotides specific for other target nucleic acids in a mixture, and conversion of hybridized expander molecules by DNA polymerases into double-stranded DNA fragments. In particular embodiments, the length of each such double-stranded DNA produced is characteristic of the target nucleic acid to which it corresponds. Alternatively, in other embodiments, the length of amplified products derived from such polymerase-extended expander molecules is different for each different target nucleic acid represented. What is critical is that each different target nucleic acid is represented by an extension or amplification product of different size. Various approaches for achieving differently sized representative products, also referred to herein as "surrogate markers," are discussed elsewhere herein.

Also provided herein, as further embodiments of such novel approaches, are methods for the detection and quantification of a plurality of different classes of target RNA sequences in a sample, based on using, for each target RNA sequence, a prosthetic molecule that is substantially identical at its 3'-end to at least a portion of the sequence of such target RNA and is characteristic for the target RNA being detected, and, in some embodiments, is different in length from prosthetic molecules specific for other target RNAs in a mixture, such that extension of this prosthetic molecule by DNA polymerases, and, in some embodiments, subsequent amplification, leads to the production of an extended prosthetic molecule, or an amplified extended prosthetic molecule, of discrete length that acts as a surrogate marker for the presence of such target RNA sequences in the sample.

Also provided herein, as embodiments of such novel approaches, are methods for the detection and quantification of a plurality of different classes of target RNA sequences using splint molecules of particular design, each corresponding to a specific target RNA and, in some embodiments, different in length from splint molecules specific for other target RNAs in a mixture, and extension of such hybridized splint molecules by DNA polymerases, thus leading to the production of extended splint molecules or amplified products thereof that act as discretely sized surrogate markers for each of the target RNAs present in the sample.

Accordingly, provided herein are methods for producing a discretely sized surrogate marker indicative of the presence and/or quantity of each of a plurality of target nucleic acid molecules present in a nucleic acid sample. In some aspects, the methods comprise:

a) hybridizing a plurality of different reverse-transcription primers to a nucleic acid sample comprising target RNA molecules, wherein each different reverse-transcription primer is specific for a target RNA member of the plurality of target nucleic acid molecules;

b) extending the hybridized reverse-transcription primers of step (a) with an enzyme comprising reverse-transcriptase activity to produce a mixture comprising a population of cDNA molecules corresponding to the population of target RNA molecules hybridized in step (a), where the cDNA molecules corresponding to any given target RNA can differ in size;

c) hybridizing the nucleic acids existing in the mixture after step (b) with a plurality of different single-stranded expander oligonucleotides to produce a plurality of expander oligonucleotide:DNA hybrid molecules, where each said expander oligonucleotide (i) corresponds to one member of the plurality of target nucleic acid molecules, and (ii) comprises a replica sequence that is substantially identical to a mirrored sequence within its corresponding target nucleic acid molecule, where, if such target nucleic acid molecule is an RNA molecule, the mirrored sequence is located closer to the 5'-end of the target RNA molecule than the sequence to which the reverse-transcription primers of step (a) hybridizes, and where T is substituted for U in the replica sequence;

d) extending the 3' end of the expander oligonucleotide strand of each of the plurality of expander oligonucleotide:DNA hybrid molecules produced in step (c) using a template-dependent polymerase enzyme, the extension producing, for each target nucleic acid molecule, a surrogate marker for the presence of such target nucleic acid molecule present in the nucleic acid sample, where either: (i) each surrogate marker is of a different characteristic size relative to surrogate markers for other target nucleic acids; or (ii) amplification products of respective surrogate markers are of different characteristic sizes relative to other surrogate markers or amplification products thereof.

In some aspects, the methods comprise:

a) hybridizing a plurality of different reverse-transcription primers to a nucleic acid sample comprising target RNA molecules, where each different reverse-transcription primer is specific for a target RNA member of the plurality of target nucleic acid molecules;

b) extending the hybridized reverse-transcription primers of step (a) with an enzyme comprising reverse-transcriptase activity to produce a mixture comprising a population of cDNA molecules corresponding to the population of target RNA molecules hybridized in step (a), where the cDNA molecules corresponding to any given target RNA can differ in size;

c) hybridizing the nucleic acids existing in the mixture after step (b) with a plurality of different single-stranded expander oligonucleotides to produce a plurality of expander oligonucleotide:DNA hybrid molecules, wherein each of the expander oligonucleotides (i) correspond to one member of the plurality of target nucleic acid molecules, (ii) differs in length from each of the expander oligonucleotide corresponding to all other target nucleic acid molecules, and (iii) comprises a replica sequence that is substantially identical to a mirrored sequence within its corresponding target nucleic acid molecule, where, if such target nucleic acid molecule is an RNA molecule, the mirrored sequence is located closer to the 5'-end of the target RNA molecule than the sequence to which the reverse-transcription primers of step (a) hybridizes, and where T is substituted for U in the replica sequence;

d) extending the 3' end of the expander oligonucleotide strand of each of the plurality of expander oligonucleotide:DNA hybrid molecules produced in step (c) using a template-dependent polymerase enzyme, the extension producing, for each target nucleic acid molecule, a discretely sized surrogate marker for the presence such target nucleic acid molecule present in the nucleic acid sample.

In some embodiments of these aspects and all such aspects described herein, the plurality of target nucleic acid molecules comprises target RNA molecules and target DNA molecules.

In some embodiments of these aspects and all such aspects described herein, the plurality of target nucleic acid molecules comprises target RNAs of different classes. In some such embodiments, the target RNAs of different classes include two or more of mRNA, microRNA, siRNA, or hnRNA.

In some embodiments of these aspects and all such aspects described herein, when the target nucleic acid is an RNA molecule, the mirrored sequence of the target RNA molecule, to which the replica sequence is substantially identical, is immediately 5' of the sequence to which the reverse-transcription primers of step (a) hybridizes.

In some embodiments of these aspects and all such aspects described herein, when the target nucleic acid is an RNA molecule, the reverse-transcription primer of step (a) hybridizes to a sequence within the mirrored sequence of the target RNA molecule, to which the replica sequence is substantially identical.

In some embodiments of these aspects and all such aspects described herein, when the target nucleic acid is an RNA molecule, there is gap between the 3' end of the mirrored sequence of the target RNA molecule, to which the replica sequence is substantially identical, and the 5' end of the sequence to which the reverse-transcription primer of step (a) hybridizes.

In some aspects, the method for producing a discretely sized surrogate marker indicative of the presence and/or quantity of each of a plurality of target nucleic acid molecules present in a nucleic acid sample comprises:

a) hybridizing a nucleic acid sample comprising target DNA molecules with a plurality of different single-stranded expander oligonucleotides to produce a plurality of expander oligonucleotide:DNA hybrid molecules, wherein each said expander oligonucleotide (i) corresponds to one member of the plurality of target nucleic acid molecules, and (ii) comprises a replica sequence that is substantially identical to a mirrored sequence within its corresponding target nucleic acid molecule;

b) extending the 3' end of the expander oligonucleotide strand in each of the plurality of expander oligonucleotide:DNA hybrid molecules produced in step (c) using a template-dependent polymerase enzyme, the extension producing, for each target nucleic acid molecule, a surrogate marker for the presence of each of the plurality of target nucleic acid molecules present in the nucleic acid sample, wherein either: (i) each surrogate marker is of a different characteristic size relative to surrogate markers for other target nucleic acids; or amplification products of respective surrogate markers are of different characteristic sizes relative to other surrogate markers or amplification products thereof.

In some embodiments of these aspects and all such aspects described herein, each expander oligonucleotide further comprises a forward primer sequence 5' of the replica sequence of the expander oligonucleotide.

In some embodiments of these aspects and all such aspects described herein, each expander oligonucleotide further comprises a spacer sequence, where the spacer sequence is immediately 5' of the replica sequence of the expander oligonucleotide that is substantially identical to the mirrored sequence within the corresponding target nucleic acid molecule. In some such embodiments, the spacer sequence within each member of the plurality of expander oligonucleotides is of a different, discrete length than the spacer sequence in all other members of said plurality of expander oligonucleotides.

In some embodiments of these aspects and all such aspects described herein, the replica sequence within each member of the plurality of expander oligonucleotides is at least 10 nucleotides in length.

In some embodiments of these aspects and all such aspects described herein, each expander oligonucleotide further comprises at least part of a forward primer sequence immediately 5' of the spacer sequence of the expander oligonucleotide.

In some embodiments of these aspects and all such aspects described herein, the replica sequence within each member of the plurality of expander oligonucleotides comprises 75% or more of the total length of the expander oligonucleotide.

In some embodiments of these aspects and all such aspects described herein, the nucleic acid sample comprises partially, substantially randomly degraded target nucleic acids.

In some embodiments of these aspects and all such aspects described herein, the methods further comprise the step, after step (d), of amplifying at least a portion of the plurality of extended expander oligonucleotides by PCR amplification using a plurality of amplification primer pairs, thereby generating a plurality of extended expander oligonucleotide amplicons, such that each of the amplification primer pairs comprises a forward amplification primer and a reverse amplification primer, where each amplicon generated has a different length, and where each amplicon generated provides a surrogate marker amplicon indicative of the presence and/or amount of one of the plurality of target nucleic acid molecules present in the nucleic acid sample.

In some such embodiments, each of the plurality of forward amplification primers used for amplification comprises a common 5' tag sequence. In some such embodiments the plurality of forward amplification primers used for amplification are not all of the same length. In some such embodiments, when one or more target nucleic acids are RNA molecules, each of the plurality of reverse amplification primers used for amplification of extended expander molecules corresponding to the target nucleic acids comprises a sequence consisting of the sequence of the reverse-transcription primer sequence specific for its target RNA molecule of step (a). In other such embodiments, the plurality of reverse amplification primers used for amplification are not all of the same length.

DEFINITIONS

As used herein, the terms "sample" or, more particularly, "nucleic acid sample" refer to any substance containing or presumed to contain a nucleic acid, and includes, for example, a formalin-fixed, paraffin-embedded (FFPE) material or sample, cellular extract, a tissue extract, or fluid extract, isolated from an individual(s) or organism, or any polynucleotide(s) purified or isolated from such FFPE materials, cellular, tissue or fluid extracts, including, but not limited to, skin, plasma, serum, spinal fluid, lymph fluid, synovial fluid, urine, tears, blood cells, organs, tumors, and also to samples of in vitro cell culture constituents (including, but not limited to, conditioned medium resulting from the growth of cells (including prokaryotic and eukaryotic cells) in cell culture medium, recombinant cells, and cell components). In regard to FFPE samples, these samples can comprise cellular or tissue explants obtained from an individual or organism during a medical procedure or intervention, such as a surgical procedure or biopsy. Nucleic acid samples from environmental sources are also included among "samples" to which the methods described herein can be applied.

As used herein, the terms "nucleic acid," "polynucleotide," and "oligonucleotide" generally refer to any polyribonucleotide or poly-deoxyribonucleotide, and includes unmodified RNA, unmodified DNA, modified RNA, and modified DNA. Polynucleotides include, without limitation, single- and double-stranded DNA and RNA polynucleotides. The term polynucleotide, as it is used herein, embraces chemically, enzymatically or metabolically modified forms of polynucleotides, as well as the naturally occurring chemical forms of DNA and RNA found in or characteristic of viruses and cells, including for example, simple (prokaryotic) and complex (eukaryotic) cells. A nucleic acid polynucleotide or oligonucleotide as described herein retains the ability to hybridize to its cognate complimentary strand. A nucleic acid sample will comprise nucleic acids that serve as templates for and/or substrates for a polymerization reaction. A polynucleotide useful for the methods described herein can be an isolated or purified polynucleotide; it can be an amplified polynucleotide in an amplification reaction, or a transcribed product from an in vitro transcription reaction.

Accordingly, as used herein, the terms nucleic acid, polynucleotide and oligonucleotide also encompass primers and probes, as well as oligonucleotide fragments, and is generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including, but not limited to, abasic sites). There is no intended distinction in length between the term "nucleic acid," "polynucleotide," and "oligonucleotide," and these terms are used interchangeably. These terms refer only to the primary structure of the molecule. An oligonucleotide is not necessarily physically derived from any existing or natural sequence, but can be generated in any manner, including chemical synthesis, DNA replication, DNA amplification, reverse transcription or any combination thereof.

The terms "nucleotide" or "mononucleotide," as used herein, refer to a phosphate ester of a nucleoside, e.g., mono-, di-, tri-, and tetraphosphate esters, wherein the most common site of esterification is the hydroxyl group attached to the C-5 position of the pentose (or equivalent position of a non-pentose "sugar moiety"). The term "nucleotide" includes both a conventional nucleotide and a non-conventional nucleotide which includes, but is not limited to, phosphorothioate, phosphite, ring atom modified derivatives, and the like.

As used herein, the term "conventional nucleotide" refers to one of the "naturally occurring" deoxynucleotides (dNTPs), including dATP, dTTP (or TTP), dCTP, dGTP, dUTP, and dITP.

As used herein, the term "nonextendable nucleotide" refers to nucleotides that prevent extention of a polynucleotide chain by a polymerase. Examples of such nucleotides include dideoxy nucleotides (ddA, ddT, ddG, ddC) that lack a 3'-hydroxyl on the ribose ring, thereby preventing 3' extension by DNA polymerases. Other examples of such nucleotides include, but are not limited to, inverted bases, which can be incorporated at the 3'-end of an oligo, leading to a 3'-3' linkage, which inhibits extension by DNA polymerases.

As used herein, the term "non-conventional nucleotide" refers to a nucleotide that is not a naturally occurring nucleotide. The term "naturally occurring" refers to a nucleotide that exists in nature without human intervention. In contradistinction, the term "non-conventional nucleotide" refers to a nucleotide that exists only with human intervention, i.e., an "artificial nucleotide." A "non-conventional nucleotide" can include a nucleotide in which the pentose sugar and/or one or more of the phosphate esters is replaced with a respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. A non-conventional nucleotide can show a preference of base pairing with another non-conventional or "artificial" nucleotide over a conventional nucleotide (e.g., as described in Ohtsuki et al. 2001, Proc. Natl. Acad. Sci., 98: 4922-4925, hereby incorporated by reference). The base pairing ability may be measured by the T7 transcription assay as described in Ohtsuki et al. (supra). Other non-limiting examples of "non-conventional" or "artificial" nucleotides can be found in Lutz et al. (1998) Bioorg. Med. Chem. Lett., 8: 1149-1152); Voegel and Benner (1996) Helv. Chim. Acta 76, 1863-1880; Horlacher et al. (1995) Proc. Natl. Acad. Sci., 92: 6329-6333; Switzer et al. (1993), Biochemistry 32:10489-10496; Tor and Dervan (1993) J. Am. Chem. Soc. 115: 4461-4467; Piccirilli et al. (1991) Biochemistry 30: 10350-10356; Switzer et al. (1989) J. Am. Chem. Soc. 111: 8322-8323, all of which are hereby incorporated by reference. A "non-conventional nucleotide" can also be a degenerate nucleotide or an intrinsically fluorescent nucleotide.

Because mononucleotides are reacted to make poly- and oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring, and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends.

As used herein, "complementary" refers to the ability of a single strand of a polynucleotide (or portion thereof) to hybridize to an anti-parallel polynucleotide strand (or portion thereof) by contiguous base-pairing, i.e., hydrogen bonding, between the nucleotides of the anti-parallel polynucleotide single strands, thereby forming a double-stranded polynucleotide comprising the complementary strands. A first polynucleotide is said to be "completely complementary" to a second polynucleotide strand if each and every nucleotide of the first polynucleotide forms a hydrogen-bonded base-pair with nucleotides within the complementary region of the second polynucleotide. A first polynucleotide is not completely complementary (i.e., "partially complementary") to the second polynucleotide if at least one nucleotide in the first polynucleotide does not base pair with the corresponding nucleotide in the second polynucleotide.

The degree of complementarity between polynucleotide strands has significant effects on the efficiency and strength of annealing or hybridization between polynucleotide strands. This is of particular importance in transcription, extension, and amplification reactions, such as those described herein, which depend upon binding and annealing between polynucleotide strands. Accordingly, an oligonucleotide primer, such as a reverse-transcription primer, a splint molecule, or the target-binding 3'-portion of a larger oligonucleotide primer, such as a prosthetic molecule, is "complementary" to a strand of a target nucleic acid if at least 50% (preferably, at least 60%, more preferably at least 70%, at least 80%, still more preferably at least 90% or more, up to and including 100%) of the nucleotides of the primer or splint molecule, or, in those embodiments relating to a prosthetic molecule, the target-binding 3'-portion of the oligonucleotide primer, i.e., the replica sequence, form base-pairs with nucleotides on the target polynucleotide. Generally, the 3' terminal nucleotide of a primer must base pair with a corresponding nucleotide on the target polynucleotide for a template-dependent polymerase enzyme to extend the primer. It is understood that a primer or oligonucleotide molecule, such as a splint molecule or prosthetic molecule, that is said to be "specific for" a target nucleic acid sequence comprises at least a portion of sequence that is completely complementary to or has a high degree of complementarity to a portion of the sequence of the target nucleic acid.

As used herein, the terms "target nucleic acid," "target RNA," "target DNA," "target oligonucleotide," and "target polynucleotide," refer to a nucleic acid of interest, e.g., a nucleic acid of a particular nucleotide sequence one wishes to detect and/or quantify in a sample. The terms can refer to a single-stranded or double-stranded polynucleotide molecule (e.g., RNA, DNA, as the case may be), or a specific strand thereof, to which, for example, an oligonucleotide primer or reverse transcription primer that is "specific for" the target nucleic acid anneals or hybridizes. Methods described herein are capable of detecting and/or quantifying target nucleic acids that belong to different "classes" of RNA molecules including, but not limited to, an mRNA (messenger RNA) molecule or fragment thereof, a microRNA (miRNA), a short interfering RNA (siRNA), a short hairpin RNA (shRNA), or any precursor molecule thereof. In some preferred embodiments, the target nucleic acids detected and/or quantified in a sample can belong to different classes of RNA molecules. For example, in one such preferred embodiment, multiple different miRNAs and mRNAs are quantified, In other preferred embodiments, the target nucleic acids that are detected and/or quantified also comprise or include DNA molecules, with or without simultaneous detection and/or quantification of target RNAs belonging to one or more classes of RNA molecule. In some embodiments of the aspects described herein, annealing or hybridizing of a plurality of reverse-transcription primers to a nucleic acid sample comprising, for example, one or more target RNA molecules, under specific conditions permits a reverse-transcriptase polymerase to extend the reverse-transcription primers to form a population of cDNA molecules complementary to the population of target RNA sequences. A target RNA or target nucleic acid as used herein has at least a portion of sequence that is complementary to a target-specific oligonucleotide molecule, such as a reverse-transcription primer.

As used herein, the phrases "partially degraded nucleic acid molecule," "partially, substantially randomly, degraded nucleic acid molecule," or variations thereof, including subspecies of "partially degraded RNA molecule" and "partially degraded DNA molecule," refer to a nucleic acid molecule that has undergone some degradation to generate fragments of an average size of at least 20 nucleotides in length. It is preferred that such fragments are of an average size of at least 20 nucleotides, at least 25 nucleotides, 30 nucleotides, at least 35 nucleotides, 40 nucleotides, at least 45 nucleotides, at least 50 nucleotides, at least 55 nucleotides, at least 60 nucleotides, at least 75 nucleotides, at least 80 nucleotides, at least 85 nucleotides, at least 90 nucleotides, at least 95 nucleotides, at least 100 nucleotides, at least 110 nucleotides, at least 120 nucleotides, at least 130 nucleotides, at least 140 nucleotides, or at least 150 nucleotides in length. By "substantially randomly" is meant that the nucleic acid fragments were not generated by cleavage at specific sites, such as would occur if an enzyme specific for certain sequences was present or active (e.g., a ribozyme or nuclease recognizing a specific sequence motif of, e.g., 4, 6, or more nucleotides). Such substantially random degradation is instead the consequence of, for example, non-sequence specific endo and exo-nucleases, and environmental conditions, such as repeated freeze-thawing or the process whereby the sample is prepared and stored, e.g., FFPE archiving.

In addition, a sample comprising such partially degraded nucleic acid molecules or partially, substantially randomly, degraded nucleic acid molecules, or variations thereof, refers to any sample in which fewer than 50% of the target nucleic acid molecules in the sample (particularly, but not necessarily, target RNA molecules) are full-length or less, i.e., 50% or more of the target nucleic acid molecules in the sample have undergone some amount of degradation to generate fragments of, on average, 150 nucleotides in length or less, including, for example, 140 nucleotides or less, including 130 nucleotides or less, 120 nucleotides or less, 110 nucleotides or less, 100 nucleotides or less, 90 nucleotides or less, 80 nucleotides or less, 70 nucleotides or less, 60 nucleotides or less, 50 nucleotides or less, 40 nucleotides or less, 30 nucleotides or less, but generally at least 20 nucleotides long. In some embodiments of the various aspects described herein, fewer than 45%, fewer than 40%, fewer than 35%, fewer than 30%, fewer than 25%, fewer than 20%, fewer than 15%, fewer than 10%, fewer than 5%, or less, of the nucleic acid molecules in the sample are full-length, i.e., have undergone some amount of degradation to generate fragments of, on average, 150 nucleotides in length or less, including, for example, 140 nucleotides or less, including 130 nucleotides or less, 120 nucleotides or less, 110 nucleotides or less, 100 nucleotides or less, 90 nucleotides or less, 80 nucleotides or less, 70 nucleotides or less, 60 nucleotides or less, 50 nucleotides or less, 40 nucleotides or less, 30 nucleotides or less, but generally at least 20 nucleotides long.

As used herein, an "oligonucleotide primer" refers to a polynucleotide molecule (i.e., DNA, RNA, artificial nucleotides or a combination thereof) capable of annealing to a portion of a sequence of a target nucleic acid, such as a target RNA, and providing a 3' end substrate for a polymerase enzyme to produce an enzymatic extension product that is complementary to the nucleic acid to which the polynucleotide is annealed. In one embodiment, an oligonucleotide primer is not an RNA molecule, or does not comprise ribonucleotides. An oligonucleotide primer can refer to more than one primer and can be naturally occurring, as in, for example, a purified restriction digest, or can refer to a molecule produced synthetically. An oligonucleotide primer can act as a point of initiation for the synthesis of a strand complementary to a sequence of a target nucleic acid, when placed under conditions in which primer extension can be catalyzed. A primer as described herein can be provided as a single- or double-stranded molecule. That is, in one embodiment, a primer is not double-stranded. The primer is preferably single-stranded for maximum efficiency in amplification. The conditions for initiation and extension usually include the presence of four different deoxyribonucleoside triphosphates (dNTPs) and a polymerization-inducing agent, such as a DNA polymerase or a reverse transcriptase, in a suitable buffer ("buffer" includes constituents that are cofactors for the enzymatic reactions, and/or which affect pH, ionic strength, etc.) and at a suitable temperature. "Primers" useful in the methods described herein are generally less than or equal to 200 nucleotides in length, e.g., less than or equal to 175 nucleotides in length, less than or equal to 150 nucleotides in length, less than or equal to 140 nucleotides in length, less than or equal to 130 nucleotides in length, less than or equal to 120 nucleotides in length, less than or equal to 110 nucleotides in length, less than or equal to 100 nucleotides in length, less than or equal to 90 nucleotides in length, less than or equal to 80 nucleotides in length, less than or equal to 70 nucleotides in length, less than or equal to 60 nucleotides in length, less than or equal to 50 nucleotides in length, less than or equal to 40 nucleotides in length, less than or equal to 30 nucleotides in length, less than or equal to 20 nucleotides in length, or less than or equal to 15 nucleotides in length, but preferably at least 10 nucleotides in length.

The term "primer site" or "primer binding site" refers to the segment of the sequence of a target nucleic acid sequence to which a primer hybridizes, i.e., the primer is specific for or complementary to the primer binding site. It is preferred, in some embodiments, that a primer oligonucleotide anneals or hybridizes to a target nucleic acid under stringent conditions. That is, in some embodiments, a primer oligonucleotide hybridizes to a target nucleic acid under stringent conditions. By "stringent conditions" is meant that the conditions under which hybridization or annealing is occurring permit only hybridization between nucleic acid sequences that are highly complementary, e.g., only a primer "specific for" the target nucleic acid will hybridize under stringent conditions. Stringent conditions can be achieved, for example, by increasing the temperature of and/or decreasing the salt concentrations in a reaction mixture.

As used herein, the terms "hybridizing" or "annealing" refer to the hydrogen-bonded base-pairing interaction of one oligonucleotide or polynucleotide with another oligonucleotide or polynucleotide (typically an antiparallel or complementary polynucleotide) that results in formation of a duplex, typically termed a "hybridization complex" or a "hybridized duplex." More specifically, when two sequences are said to "hybridize," as the term is used herein, each sequence is in opposite or reverse orientation with respect to the other sequence, e.g., a 5' to 3' sequence anneals to a complementary sequence that is 3' to 5' with respect to the first sequence. The ability of two oligonucleotide sequences to hybridize is a function of not only the complementarity of the two sequences, but also includes such factors as the temperature under which the two sequences are contacted (higher temperatures inhibit annealing of oligonucleotides), the pH and concentrations and identities of the salt(s) in the reaction mixture, and the concentrations of the respective oligonucleotides. It is not a requirement that two oligonucleotides have 100% complementarity over their full length to achieve hybridization. However, the greater the degree of complementarity, the greater the ability of two sequences to hybridize under what are termed "stringent hybridization conditions." Hybridization conditions useful in the methods described herein are well known to those of skill. Hybridization can be performed at elevated temperatures (such as 40-70° C.) to provide conditions under which only perfectly matched or substantially identical sequences can form a double-stranded complex. Hybridization can be preceded by brief exposure to denaturing temperature conditions (such as heating to 80-90° C.) to relax secondary structures in short RNA fragments, or to separate strands of pre-existing complexes, e.g., during a PCR amplification.

As noted above, an indication that two nucleic acid sequences are highly complementary is that the two molecules hybridize specifically to each other under stringent conditions. The phrase "hybridizing specifically to" refers to the binding, duplexing, or hybridizing of a molecule only to a particular nucleotide sequence under stringent conditions. "Stringent hybridization conditions" in the context of nucleic acid hybridization experiments are sequence dependent, and are different under different environmental parameters. Longer sequences hybridize specifically at higher temperatures. The $T_m$ is the temperature (under defined ionic strength and pH) at which 50% of the strands capable of forming a duplex structure are actually involved in such a structure. For DNA-DNA hybrids longer than 50 nucleotides at a pH between 5 and 9, for example, the $T_m$ can be approximated from the equation of Meinkoth and Wahl, *Anal. Biochem.*, 138:267 (1984), which is hereby incorporated by reference in its entirety, $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$ and/or hybridization conditions can be adjusted by one of skill in the art to permit annealing to sequences of the desired complementarity. For RNA-RNA hybrids, the $T_m$ can be approximated from the equation: $T_m$=79.8+18.5 (log M)+58.4 (XG+XC)+11.8 (XG+XC)2−820/L−0.35F, where XG+XC are the mole fractions of G and C respectively in the oligonucleotide, L is the length of the shortest strand in the duplex, and F is the molar concentration of formamide. For DNA-RNA hybrids, the $T_m$ can be approximated from the equation: $T_m$=79.8+18.5 log M+58.4 (XG+XC)+11.8 (XG+XC)2−820/L−0.50F, where XG+XC are the mole fractions of G and C respectively in the oligonucleotide, L is the length of the shortest strand in the duplex, and F is the molar concentration of formamide.

Generally, stringent conditions are selected to be about 5° C. lower than the thermal melting point ($T_m$) for the specific sequence and its complement at a defined ionic strength and pH. However, highly stringent conditions can utilize a hybridization at 1, 2, 3, or 4° C. lower than the thermal melting point ($T_m$). Using the equation, hybridization, and desired T, those of ordinary skill will understand that variations in the stringency of hybridization are inherently described. An extensive guide to the hybridization of nucleic acids is found in Tijssen, *Laboratory Techniques in Biochemistry and Molecular Biology Hybridization with Nucleic Acid Probes*, Part I Chapter 2 "Overview of Principles of Hybridization and the Strategy of Nucleic Acid Probe Assays," Elsevier, New York (1993), which is hereby incorporated by reference in its entirety.

The term "mirrored portion," as used herein, refers to a sequence within a target nucleic acid, e.g., a target RNA or DNA molecule, to which a sequence within an expander oligonucleotide, splint molecule or prosthetic molecule, as these terms are defined herein, is substantially identical. A mirrored portion preferably comprises at least 10 nucleotides, at least 12 nucleotides, at least 15 nucleotides, at least 20 nucleotides, or more, within the target nucleic acid sequence.

The term "replica sequence," as used herein, refers to a sequence within an expander oligonucleotide, splint molecule or prosthetic molecule, as these terms defined herein, that is substantially identical to the mirrored portion within a target nucleic acid. A replica sequence preferably comprises at least 10 nucleotides, at least 12 nucleotides, at least 15 nucleotides, at least 20 nucleotides, or more, of the expander oligonucleotide, splint molecule or prosthetic molecule.

The term "RT primer site," as used herein, refers to the sequence within a target RNA sequence to which a reverse-transcription primer used for cDNA synthesis is complementary and/or hybridizes. An RT primer site preferably comprises at least 8 nucleotides, more preferably at least 15 nucleotides, within the target RNA.

As used herein, a "corresponding cDNA molecule" refers to a cDNA molecule produced by reverse transcription of a particular target RNA molecule, i.e., the target RNA molecule to which it corresponds.

When used in connection with the cDNA molecules produced by reverse transcription from any given target RNA, the phrase "can differ in size" refers to the fact that different fragments of such target RNA can have different lengths—because these fragments were generated by strand breaks at different places in such target RNA—and therefore represent templates of different sizes for the reverse transcription process, resulting in the production of cDNAs that differ in size even though they correspond to the same target RNA.

As defined herein, an "expander oligonucleotide" refers to a polynucleotide, preferably a DNA polynucleotide, preferably single-stranded, of predefined and specific sequence length, comprising a replica sequence substantially identical to the mirrored portion of a specific target nucleic acid. The replica sequence of the expander oligonucleotide can thus hybridize to a complementary nucleic acid molecule, such as a complementary DNA molecule, that comprises a sequence complementary to the mirrored portion of the target RNA or DNA molecule to which it corresponds, such as, in the case of a target RNA, a sequence within a cDNA molecule transcribed from such target RNA. Polymerase extension of the 3'-end of the expander oligonucleotide, or the 3'-end of both the expander oligonucleotide and the DNA molecule to which it is hybridized, forms an extension product of specific length termed herein as an "extended expander oligonucleotide" that provides for a "surrogate marker" indicative of the presence of the target RNA or DNA sequence in a sample. The extended expander oligonucleotide can be amplified with appropriate primers to generate a surrogate marker of selected length indicative of the presence of the target RNA or DNA sequence in a sample. An expander nucleotide is added to a reaction described herein, rather than being synthesized during a reaction described herein. Thus, the complement of a target nucleic synthesized, e.g., by reverse transcription or template-dependent amplification using the target is not an expander oligonucleotide.

As defined herein, a "prosthetic molecule" refers to a polynucleotide, preferably a DNA polynucleotide, preferably single-stranded, of predefined and specific sequence length comprising, in the 5' to 3' direction: (i) a spacer sequence of defined length, and (ii) a replica sequence substantially identical to the mirrored portion of a specific target nucleic acid. Accordingly, prosthetic molecules are a subset of expander molecules as described herein. In one preferred embodiment, the prosthetic molecule further comprises a forward primer sequence at its 5'-end, such that the prosthetic molecule comprises, in the 5' to 3' direction, (i) a forward primer sequence, (ii) a spacer sequence, and (iii) a replica sequence. The spacer sequence in a prosthetic molecule can be of any sequence, and is preferably designed to minimize the potential of the spacer sequence to anneal with any other nucleic acids present in the same reactions as the prosthetic molecule, for example, by including a multiplicity of A and T nucleotides that will reduce the $T_m$ of any duplexes involving the spacer sequence. The replica sequence of the prosthetic molecule can hybridize to any cDNA or DNA molecule that comprises a sequence complementary to the mirrored portion of the target RNA or DNA molecule, such that polymerase extension of the hybridized prosthetic molecule forms an extension product of discrete length termed herein as an "extended prosthesis" that, upon amplification, can be used as a "surrogate marker" indicative of the presence of the target nucleic acid sequence in a sample. In those embodiments of the methods relating to target RNA sequences, this requires that the mirrored portion of the prosthetic molecule is closer than the RT primer site to the 5'-end of the target RNA. The 3'-end of the prosthetic molecule can be located immediately adjacent, on the 5'-side, to the RT primer site within the target RNA sequence, or can even overlap such site. Alternatively, in other embodiments, there can be a gap between the 3'-end of the prosthetic molecule and the RT primer site within the target RNA sequence.

As used herein, a "splint molecule" or "splint probe" refer to a polynucleotide, preferably a DNA polynucleotide, preferably single-stranded, of predefined and specific sequence length, the greater part or all of which sequence comprises a replica sequence substantially identical to the mirrored portion of a specific target nucleic acid, such that the splint molecule can serve as a template for extension of nucleic acid sequences complementary to the target nucleic acid. Accordingly, splint molecules are a subset of expander molecules as described herein. In those embodiments relating to target RNA sequences, this requires that the mirrored portion is 5' of the RT primer site within the target RNA sequence. The replica sequence of the splint molecule extends to and comprises the 3'-end of the splint molecule, and can preferably comprise at least 25 nucleotides, at least 30 nucleotides, at least 35 nucleotides, at least 50 nucleotides, at least 75 nucleotides, at least 100 nucleotides, at least 150, or at least 175 nucleotides. In those embodiments relating to target RNA sequences, the 3'-end of the splint molecule can be located immediately adjacent, on the 5'-side, to the RT primer site within the target RNA, or can even overlap such site. Alternatively, there can be a gap between the 3'-end of the splint molecule and the RT primer site within the target RNA sequence. In some embodiments, an amplification primer for use in amplification of an extended splint molecule comprises a sequence within the 5' end of the splint molecule. The extension of a splint molecule hybridized to a nucleic acid sequence complementary to the target nucleic acid sequence to which the splint molecule corresponds forms an extension product of discrete length, termed herein an "extended splint" or "extended splint molecule," that provides for a surrogate marker indicative of the presence of such target nucleic acid sequence(s) in a sample. Amplification of the extended splint molecule with appropriate primers provides a surrogate marker of selected length that is indicative of the presence of the target nucleic acid sequence in a sample.

As used herein, a "surrogate marker" refers to an extended expander oligonucleotide, an extended prosthetic molecule, or an extended splint molecule. As used herein, the term "surrogate marker" also includes any amplified products or amplicons of an extended expander oligonucleotide, extended prosthetic molecule, or an extended splint molecule, i.e., an extended expander oligonucleotide amplicon, an extended prosthetic molecule amplicon, or an extended splint molecule amplicon, as those terms are defined herein.

As used herein, the use of the term "discrete length" or "discrete size" to describe a surrogate marker means that the length or size of such surrogate marker is characteristic of the particular target nucleic acid from which it is derived and different from the lengths or sizes of surrogate markers derived from other target nucleic acids in the sample.

A "polymerase," as used herein, refers to an enzyme that catalyzes polynucleotide synthesis by addition of nucleotide units to a nucleotide chain using DNA or RNA as a template. The term refers to either a complete enzyme as it occurs in nature, or an isolated, active catalytic domain, or fragment. Generally, the polymerase enzyme initiates synthesis at the 3'-end of a primer or oligonucleotide, such as an expander oligonucleotide, annealed or hybridized to a template target sequence, and proceeds in the 5'-direction along the target nucleic acid to synthesize a strand complementary to the target nucleic acid until synthesis terminates.

As used herein, the term "thermostable nucleic acid polymerase" refers to an enzyme that is relatively stable to heat when compared, for example, to nucleotide polymerases from *E. coli*, and which catalyzes the template-dependent polymerization of nucleoside triphosphates. A "thermostable nucleic acid polymerase," as the term is used herein, retains enzymatic activity for polymerization and exonuclease activities when subjected to the repeated heating and cooling cycles used in PCR. Preferably, a "thermostable nucleic acid polymerase" has optimal activity at a temperature above 45° C. A representative thermostable polymerase enzyme isolated from *Thermus aquaticus* (Taq) is described in U.S. Pat. No. 4,889,818 and methods for using it in conventional PCR are described in Saiki et al., 1988, Science 239:487 and Gelfand, "Taq DNA Polymerase" in PCR Technology; Principles and Applications for DNA Amplification, Erlich, Ed., Stockton Press, N.Y. (1989), Chapter 2). Thermostable polymerases useful for e.g., PCR and related methods are well known to those of skill in the art and are widely available.

As used herein, "extending" refers to any enzyme-catalyzed, in vitro method for synthesizing a new strand of polynucleotide or elongating an existing polynucleotide or oligonucleotide (e.g., a reverse transcription oligonucleotide primer hybridized to a target RNA, or an expander oligonucleotide, e.g., prosthetic molecule or splint molecule, hybridized to a complementary DNA) in a template-dependent manner. The act of extending according to the methods described herein, can be a component of amplification, which increases the number of copies of a polynucleotide template sequence with the use of a polymerase. Extending a polynucleotide results in the incorporation of nucleotides into a polynucleotide (including nucleotides complementary to those in the template that comprise a spacer or span a gap), thereby forming an extended polynucleotide molecule complementary to the polynucleotide template. The extended polynucleotide molecule can be used as a template for PCR amplification or as a template to transcribe polynucleotide molecules. Optionally the transcription can be performed in the presence of labeled nucleotides or ribonucleotides, further facilitating detection and/or quantification. In some embodiments, to prevent extension of a polynucleotide that would be undesirable, the polynucleotide can include a non-extendable base at its 3'-end such as a dideoxy nucleotide or inverted base. Extension can be performed at an elevated temperature to preserve specificity of hybridization, ensuring that only perfectly matched, i.e., completely complementary, sequences are extended by the polymerase.

When two different, non-overlapping oligonucleotides anneal or hybridize to different regions of the same linear complementary target nucleic acid sequence, and the 3' end of the first oligonucleotide points toward the 5' end of the other, second oligonucleotide, the former can be called the "upstream" oligonucleotide and is considered "5'" of the second oligonucleotide, and the latter the "downstream" oligonucleotide and is "3'" of the first oligonucleotide.

As understood by one of skill in the art, in those embodiments where there is a gap between the 3' end of the mirrored portion of the target RNA sequence and the 5'-end of the RT primer site, the length of such gap should be less than the average length of the degraded RNA molecules in a sample.

As used herein, the terms a "spacer" or a "spacer sequence" refer to a heterologous or random nucleotide sequence containing a known number of nucleotides. The number of nucleotides, or analogues thereof, in the spacer can range from at least 2 nucleotides, or analogues thereof up to and including at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, or at least 175 nucleotides or analogues thereof.

As used herein, "isolated" or "purified" when used in reference to a polynucleotide means that a naturally occurring sequence has been removed from its normal cellular environment or is in a non-natural environment. Thus, an "isolated" or "purified" sequence can be in a cell-free solution or placed in a different cellular environment. The term "purified" does not imply that the sequence is the only polynucleotide present, but that it is essentially free (about 90-95%, up to 99-100% pure) of non-polynucleotide material naturally associated with it.

The term "amplification reaction" refers to an in vitro process for providing multiple copies of a target sequence of nucleic acid, i.e., where more than one copy of a target nucleic acid sequence is made. "Amplifying" refers to a step of subjecting nucleic acids in a solution to conditions sufficient to allow for amplification of a target nucleic acid polynucleotide, if all of the components of the reaction are intact. Components of an amplification reaction include, e.g., primer pairs (a "forward primer" and a "reverse primer"), a polynucleotide template, polymerase, nucleotides, and the like. The term "amplifying" typically refers to an "exponential" increase in the number of copies of a target nucleic acid. However, "amplifying" as used herein can also refer to linear increases in the number of copies of a select target sequence of nucleic acid. Accordingly, the term "amplification reaction mixture" refers to an aqueous solution comprising the various reagents used to amplify a target nucleic acid. These include components such as enzymes, aqueous buffers, salts, amplification primers, target nucleic acid, and nucleoside triphosphates. Depending upon the context, the mixture can be either a complete or incomplete amplification reaction mixture. In one embodiment of the aspects described herein, an amplification reaction is a PCR reaction.

"Polymerase chain reaction" or "PCR" refers to a method whereby a specific segment or subsequence of a target nucleic acid, is amplified in a geometric progression, using repeated cycles of forward and reverse primer annealing, primer extension, and thermal strand separation. PCR is well known to those of skill in the art; see, e.g., U.S. Pat. Nos. 4,683,195 and 4,683,202; and PCR Protocols: A Guide to Methods and Applications, Innis et al., eds., 1990; Sambrook and Russell, MOLECULAR CLONING, A LABORATORY MANUAL (3rd ed. 2001); and CURRENT PROTOCOLS IN MOLECULAR BIOLOGY (Ausubel et al., eds., John Wiley & Sons, Inc. 1994-1997, 2001 version).

"Multiplex amplification" refers to amplification of multiple different target nucleic acid sequences in the same reaction (see, e.g., PCR PRIMER, A LABORATORY MANUAL (Dieffenbach, ed. 1995) Cold Spring Harbor Press, pages 157-171). "Multiplex amplification," as used herein, refers to amplification of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30 or more targets, e.g., at least 50, at least 100, at least 250, or more, targets.

As used herein, reference to a "size distinguishable by capillary electrophoresis" means a difference of at least one nucleotide, but preferably at least 5 nucleotides or more.

As used herein, "label" or "detectable label" refers to any moiety or molecule that can be used to provide a detectable (preferably quantifiable) signal. A "labeled nucleotide" (e.g., a NTP or dNTP), or "labeled polynucleotide", is one linked to a detectable label. The term "linked" encompasses covalently and non-covalently bonded, e.g., by hydrogen, ionic, or Van der Waals bonds. Such bonds can be formed between at least two of the same or different atoms or ions as a result of redistribution of electron densities of those atoms or ions. Labels can provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A nucleotide useful in the methods described herein can be labeled so that the transcribed product can incorporate the labeled nucleotide and becomes detectable. A fluorescent dye is a preferred label according to the methods described herein. Suitable fluorescent dyes include fluorochromes such as Cy5, Cy3, rhodamine and derivatives (such as Texas Red), fluorescein and derivatives (such as 5-bromomethyl fluorescein), Lucifer Yellow, IAEDANS, 7-Me.sub.2N-coumarin-4-acetate, 7-OH-4-CH.sub.3-coumarin-3-acetate, 7-NH.sub.2-4-CH.sub.3-coumarin-3-acetate (AMCA), monobromobimane, pyrene trisulfonates, such as Cascade Blue, and monobromorimethyl-ammoniobimane (see for example, DeLuca, Immunofluorescence Analysis, in Antibody As a Tool, Marchalonis et al., eds., John Wiley & Sons, Ltd., (1982), which is incorporated herein by reference).

It is intended that the term "labeled nucleotide", as used herein, also encompasses a synthetic or biochemically derived nucleotide analog that is intrinsically fluorescent, e.g., as described in U.S. Pat. Nos. 6,268,132 and 5,763,167, Hawkins et al. (1995, Nucleic Acids Research, 23: 2872-2880), Seela et al. (2000, Helvetica Chimica Acta, 83: 910-927), Wierzchowski et al. (1996, Biochimica et Biophysica Acta, 1290: 9-17), Virta et al. (2003, Nucleosides, Nucleotides & Nucleic Acids, 22: 85-98), the entirety of each is hereby incorporated by reference. By "intrinsically fluorescent", it is meant that the nucleotide analog is spectrally unique and distinct from the commonly occurring conventional nucleosides in their capacities for selective excitation and emission under physiological conditions. For the intrinsically fluorescent nucleotides, the fluorescence typically occurs at wavelengths in the near ultraviolet through the visible wavelengths. Preferably, fluorescence will occur at wavelengths between 250 nm and 700 nm and most preferably in the visible wavelengths between 250 nm and 500 nm.

The terms "detectable label" or "label" include a molecule or moiety capable of generating a detectable signal, either by itself or through the interaction with another label. The "label" can be a member of a signal generating system, and thus can generate a detectable signal in context with other members of the signal generating system, e.g., a biotin-avidin signal generation system, or a donor-acceptor pair for fluorescent resonance energy transfer (FRET) (Stryer et al., 1978, Ann. Rev. Biochem., 47:819; Selvin, 1995, Methods Enzymol., 246:300). In one aspect, a "label" does not require another moiety or member to generate a signal.

The practice of the methods described herein will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Polynucleotide Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). The practice of the methods described herein can also involve techniques and compositions as disclosed in U.S. Pat. Nos. 5,965,409; 5,665,547; 5,262,311; 5,599,672; 5,580,726; 6,045,998; 5,994,076; 5,962,211; 6,217,731; 6,001,230; 5,963,456; 5,246,577; 5,126,025; 5,364,521; 4,985,129; as well as in U.S. patent application Ser. Nos. 10/113,034; 10/387,286; 10/719,185; 10/600,201; 10/752,123 and 10/719,746. All patents, patent applications, and publications mentioned herein, both supra and infra, are hereby incorporated by reference.

BRIEF DESCRIPTION OF THE DRAWINGS

FIG. 7 schematically shows the design of primers/templates establishing a distinguishably sized product specific for each variant to be detected.

FIG. 8 shows the exon make-up of the ALK mRNA, the location of the tyrosine kinase domain in the polypeptide and the location of a fusion point that results in the EML4-ALK oncogene.

FIG. 9 shows results of an assay performed using primers and expander templates specific for EML4-ALK variants 1-6, with synthetic variant and wild-type target templates representing variants 1-6 and wild-type EML4 and ALK. Product sizes are as indicated in the chart at right.

FIG. 10 shows results of assays performed in which primers/expander templates for variants 1-6 were included in the assay, but only selected variant templates (v3a, left, v6, center, v4a right) were included, demonstrating the specificity of the assay.

DETAILED DESCRIPTION

Figure 1:
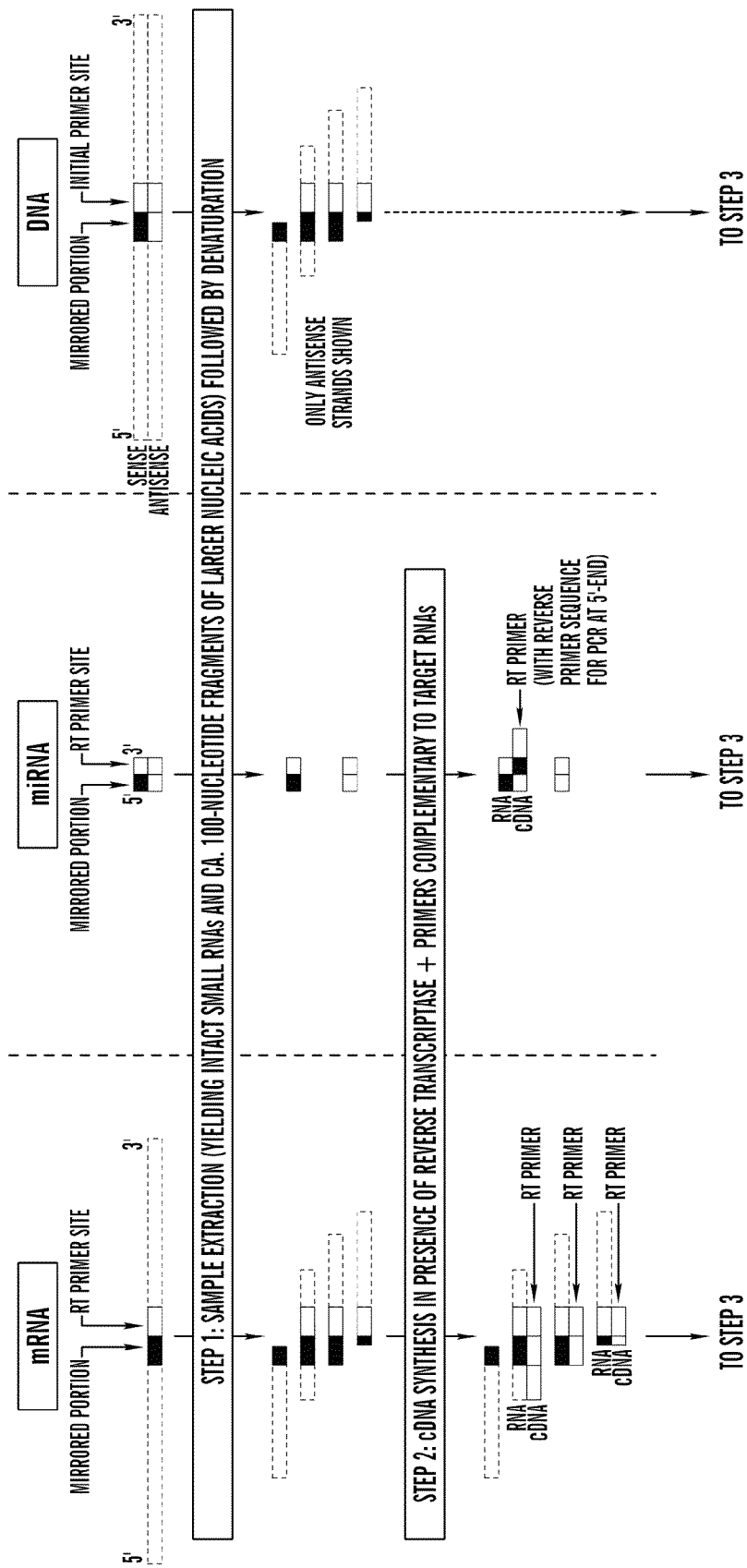
FIG. 1 provides a schematic for a method for generating extended expander/prosthetic molecule amplicons of different, predetermined lengths specific for both a DNA target as well as multiple classes of RNA targets from a nucleic acid sample in a single reaction, according to one embodiment of the methods described herein. In this schematic diagram, different prosthetic molecules of defined and different lengths and specific for three different target sequences are extended, upon hybridization to complementary DNA molecules, and amplified into multiple copies having specific, predefined lengths, such that each extended prosthetic molecule is indicative of the presence of a specific target DNA or RNA sequence in the sample. Nucleic acid molecules comprising target RNA sequences are shown herein using dotted lines for their outlines, with the solid line sections within each one indicating the mirrored portion of the target sequence and the RT primer site.
Figure 1:
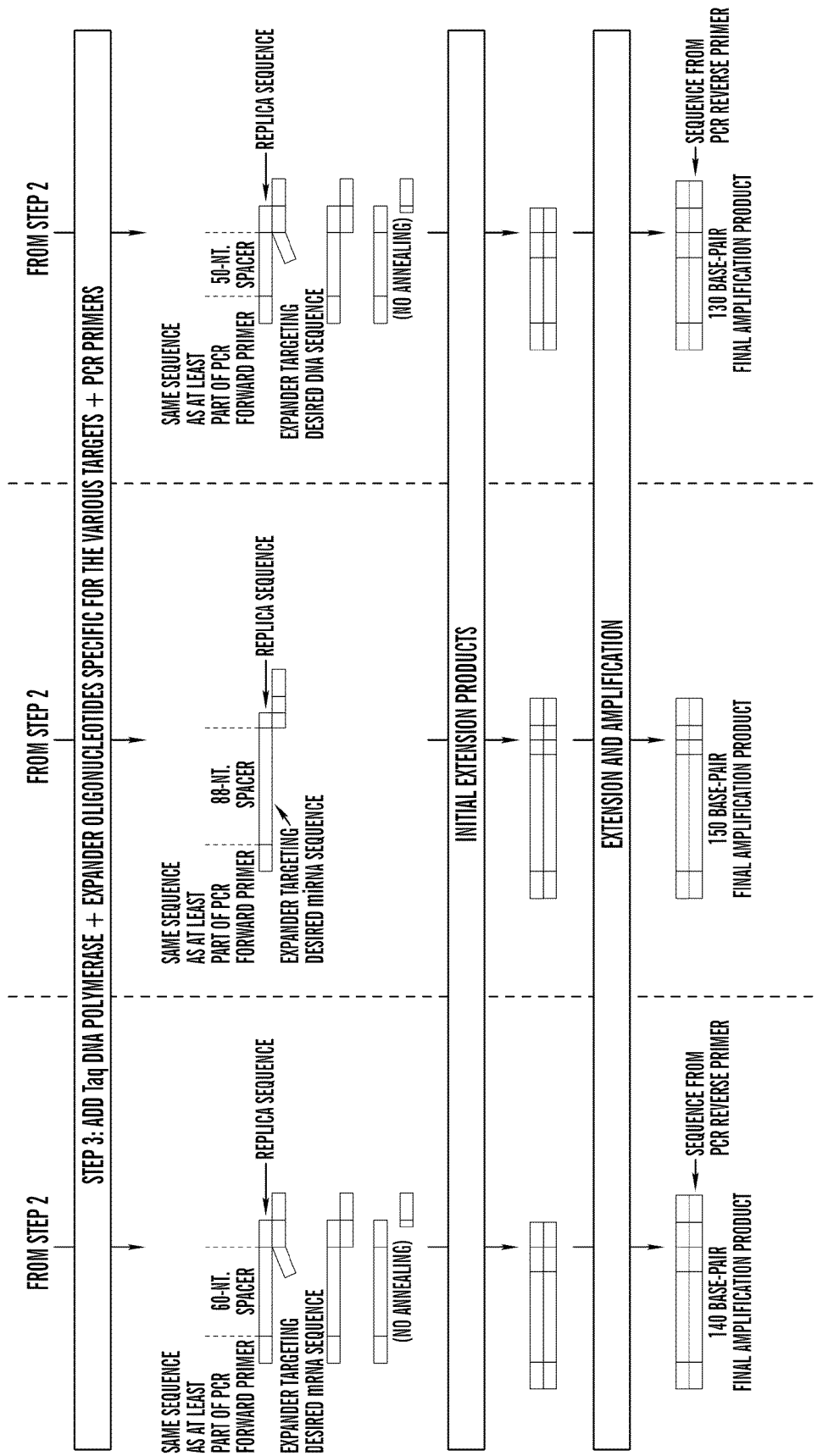
Figure 2:
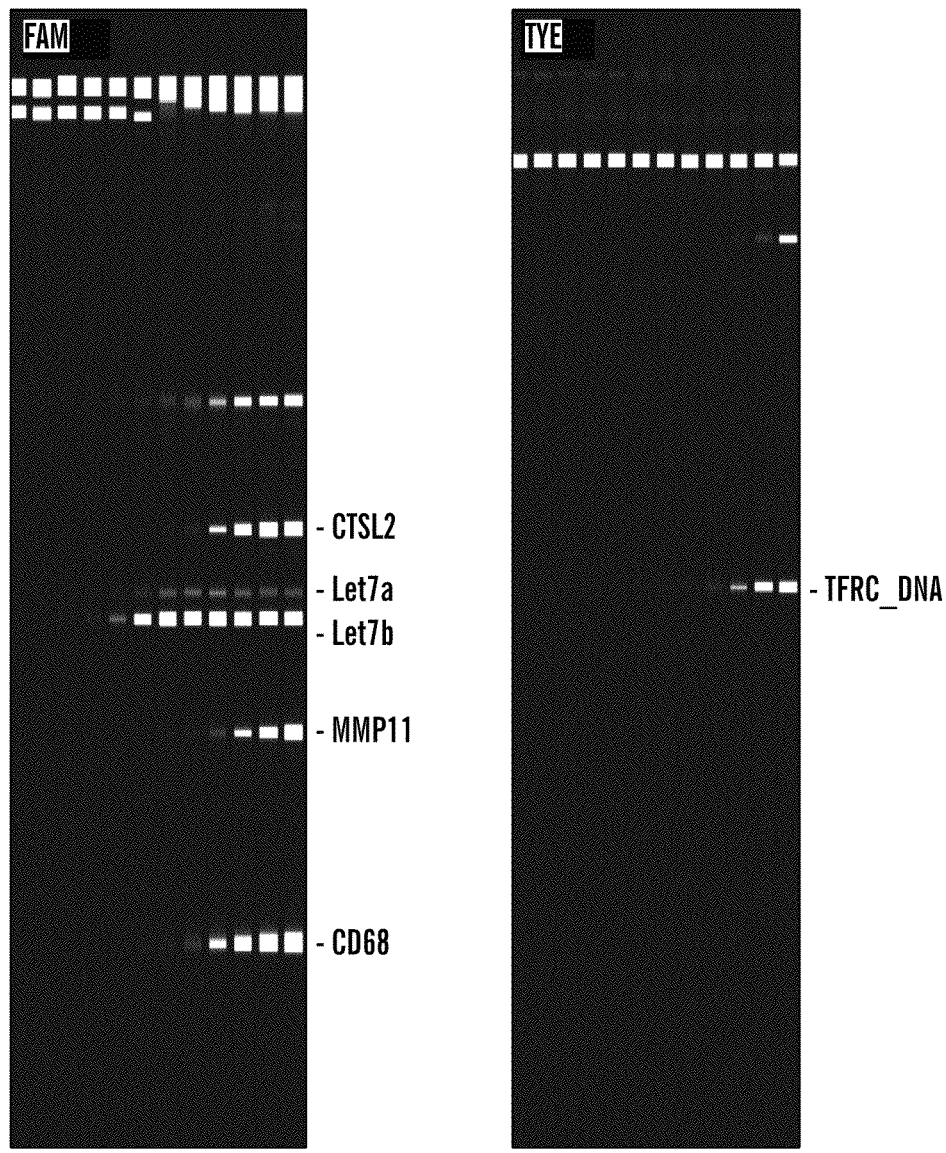
FIG. 2 demonstrates exemplary data generated using an embodiment of the multi-modal prosthetic oligonucleotide methods described herein, where multiple classes of RNA targets as well as a DNA target were detected from starting FFPE material. Using prosthetic oligonucleotides specific for each target, three mRNA targets (CTSL2, MMP11, CD68), two miRNA targets (let7a/b), and one DNA target (TFRC_DNA, TYE channel) were detected in a single reaction. Nucleic acids present in samples taken at stages during the PCR amplification were separated by capillary electrophoresis.

Described herein are approaches for the detection and quantification of target nucleic acid sequences, such as partially degraded nucleic acids, in a biological sample. These methods permit the detection and quantification of individual species of target RNA sequences and/or DNA sequences in a nucleic acid sample, both singly as well as in multiplex formats that permit the determination of the presence of and/or amounts of two or more such target nucleic acid sequences, including partially degraded nucleic acids, in a single reaction, through the generation of discretely-sized surrogate markers using splint molecules or prosthetic molecules, as described herein. The methods described herein permit the production and detection of surrogate markers that are substantially longer than the target nucleic acid sequences present in the sample from which they are generated, such as, for example, in samples comprising fragmented nucleic acids, such as fragmented RNA species or DNA molecules, thereby allowing size-based separation systems, such as capillary electrophoresis, to be used to identify and/or quantify target sequences in such samples.

Among the most reliable current method for quantitative detection of RNA are those that comprise reverse transcription of RNA molecules followed by real-time quantitative PCR analyses. Such methods typically require multiple different oligonucleotides specific for each target RNA that is being measured, which are used to prime cDNA synthesis, prime the PCR amplification steps, and generate a fluorescent signal, the growth or increase of which during the PCR amplification steps is used to estimate the quantity of RNA present in a sample. Because standard methods for real-time PCR are "homogeneous" assays in which no separation steps are required, they can be difficult to adapt for multiplex assays in which multiple different target RNA sequences are to be quantified in a single reaction, as the amplicons generated from different species of target RNA sequences can only be distinguished if the fluorescent signals they generate can be distinguished. This can be very challenging because of the significant overlap in the emission spectra of many commonly available fluorescent agents, and the requirement in such methods of having unique and distinguishable fluorescent agents or labels for each target RNA species to be detected, and the requisite instrumentation, e.g., multiple lasers, for detection of the different labels used.

The novel methods described herein, in contrast, avoid this difficulty by converting each target nucleic acid sequence of interest into a surrogate marker or surrogate marker amplicon of unique size, that can easily be separated from other surrogate markers or surrogate marker amplicons generated from other target nucleic acid sequences in the same reaction and then quantified, thereby allowing simultaneous detection and quantification of multiple, different target nucleic acid sequences in a single reaction, including both RNA targets and DNA targets. Thus, the expander oligonucleotides described herein, such as prosthetic molecules and splint molecules, allow reliable transformation of target nucleic acid sequences into homogenous populations of surrogate markers or surrogate marker amplicons, each with a length that is pre-defined and characteristic for the target nucleic acid sequence from which it was generated. These methods are particularly useful when such target nucleic acid sequences have been randomly degraded into short fragments of different lengths, by allowing multiplex analyses and size-based separation and detection methods to be used in spite of the short and random lengths of these fragments, as described herein.

The detection of individual species of discretely sized surrogate markers or surrogate marker amplicons generated for each of the target nucleic sequences present in a nucleic acid sample can be accomplished, in some embodiments, by size-separation of the discretely sized surrogate markers or surrogate marker amplicons, for example, by capillary electrophoresis, coupled with detection by, for example, fluorescence detection of labeled surrogate markers. Such quantification of the detected discretely sized surrogate markers or surrogate marker amplicons representing each of the target nucleic acid species in a sample can be accomplished, for example, by generating a standard curve by applying the methods described herein to control nucleic acids added to the test sample in various known concentrations. The standard curve permits the determination of the concentration(s) of the target nucleic acid sequences in the same reaction.

Accordingly, the approaches described herein provide methods of identifying, and/or detecting, and/or quantifying a target nucleic acid present in, or isolated from, a sample of interest comprising the following steps, which can be performed contemporaneously, but alternatively can be separated in time, e.g., as when reverse transcription and cDNA synthesis of, for example, each target RNA sequence, is followed some time later (e.g., hours, days, etc.) by hybridization of expander oligonucleotides and extension steps to produce surrogate markers for each target nucleic acid sequence, either target RNA molecules, target DNA molecules, or both, present in a sample.

In those embodiments of the methods involving detection of one or more target RNA sequences, the initial steps involve, in part, generating complementary DNA (cDNA) from the RNA sequences present in a sample, such as a sample comprising partially, substantially randomly, degraded nucleic acid molecules. This is accomplished by hybridization of one or more reverse transcription (RT) primer sequences to the target RNA, under conditions that permit the RT primer sequences to bind to any target RNA sequences present in the sample to which they are complementary. In preferred embodiments, reverse transcription (RT) primer sequences added to the nucleic acid sample are specific for each target RNA sequence of interest in the nucleic acid sample, under conditions which permit the target specific reverse-transcription primers to bind to RT primer sites in any target RNA sequences present in the sample. In other embodiments, RT priming can commence from random priming events by nucleic acids (RNAs or DNAs) already present in the sample in a process referred to herein as 'background priming,' as described in Frech, B. and Peterhans, E. (1994) RT-PCR: 'background priming' during reverse transcription. *Nucl. Acids Res.* 22, 4342-4343, the contents of which are herein incorporated by reference in their entireties. In other embodiments, RT primers added to the sample comprise random hexamer primers.

Subsequently, any hybridized reverse-transcription primers are extended, using an enzyme comprising reverse transcriptase activity, to produce a population of cDNA molecules corresponding to each target RNA fragment hybridized to a reverse transcription primer, such that the cDNA molecules corresponding to a given target RNA sequence in a sample can have different sizes depending upon the location of strand breaks in the nucleic acid molecule comprising the target RNA sequence, and, in the case where endogenous or exogenous random primers were used, on the site at which priming occurred. In embodiments in which cDNA synthesis is primed using target-specific RT primers, all of the cDNA molecules corresponding to a given target RNA sequence following reverse-transcription will have identical 5'-ends, even though these molecules can have different sizes.

The subsequent steps comprise, in part, hybridizing the nucleic acids now present in the sample, comprising reverse-transcription cDNA products corresponding to the various target RNAs, together with any target DNAs originally present in the sample, with a separate set of one or more expander oligonucleotides, each specific for one particular target nucleic acid sequence. In some embodiments, each expander oligonucleotide further differs in length from the expander oligonucleotides specific for other target nucleic acid sequences present in the sample. Each expander oligonucleotide comprises a replica sequence located at its 3' end that is substantially identical to the mirrored portion of the target nucleic sequence for which it is specific.

In those aspects and embodiments related to prosthetic molecules, each prosthetic molecule is preferably single-stranded and comprises, starting at the 5'-end, (i) a spacer sequence of defined length, and (ii) a target-specific replica sequence identical or substantially identical to the mirrored portion of a target nucleic acid sequence, depending on whether the target nucleic acid sequence is a DNA molecule or an RNA molecule. As used herein, a DNA molecule is said to be "substantially identical" to an RNA molecule, or vice versa, where the DNA molecule comprises T nucleotide substitutions for the U nucleotides present in the RNA molecule, and vice versa, but all other nucleotides in the sequence are identical or equivalent. The replica sequence of a prosthetic molecule is identical to or substantially identical to the mirrored portion of the corresponding target nucleic acid sequence. Where a prosthetic molecule is specific for a target RNA sequence, the 3' end of the mirrored portion of the target RNA sequence is 5' or upstream of at least part of the 5' end of the RT primer site in the target RNA molecule.

In some embodiments, a prosthetic molecule further comprises, at its 5' end and 5' of the spacer sequence, a sequence corresponding to a primer sequence or a portion of a primer sequence to be used in subsequent amplification steps.

Any prosthetic molecules hybridized to their corresponding target nucleic acid sequence, or cDNA reverse-transcribed from or corresponding to their target nucleic acid sequence, can then be extended from their 3' ends using a template-dependent polymerase, resulting in discretely sized "extended prosthetic molecules" or "surrogate markers" of predetermined size, each of which represents a target nucleic acid sequence present in the sample. In some embodiments, the extension step produces extended prosthetic molecules whose predetermined and discrete lengths are characteristic of the target nucleic acid molecule to which they correspond.

An important feature of those aspects and embodiments related to prosthetic molecules is that the extended prosthetic molecules, not the original cDNA molecules or target DNA molecules, are the basis for subsequent amplification and detection steps in the methods described herein. In most instances of such aspects, the prosthetic molecule does not itself serve as a template, because either the 3'-end of the target nucleic acid sequence or corresponding cDNA molecule to which the prosthetic molecule hybridizes is dangling freely, or the match or region of complementarity between the prosthetic molecule and target nucleic acid or corresponding cDNA molecule is too short, so that only in those very few instances where the 3'-end of the target nucleic acid or corresponding cDNA molecule matches and hybridizes to essentially the entire length of the replica sequence of the prosthetic molecule does extension of the cDNA molecule or target DNA nucleic acid occur—otherwise only the prosthetic molecules are extended. To the extent that the cDNA or target nucleic acid (e.g., DNA molecule) when hybridized to the prosthetic molecule is longer (in its 3' direction) than the replica sequence of the prosthetic molecule, the cDNA or target nucleic acid (e.g., DNA molecule) hybridized to the prosthetic molecule will not be extended by a template-dependent polymerase.

In those aspects and embodiments related to splint molecules, each oligonucleotide DNA splint molecule is preferably single-stranded and is comprised mostly or completely of a replica sequence substantially identical to the mirrored portion of the corresponding target nucleic acid. The double-stranded molecules comprising splint molecules hybridized to target DNA molecules or to cDNA molecules corresponding to target RNA molecules are then extended from each of their 3' ends using a template-dependent polymerase, resulting in discretely sized extended splints or "surrogate markers" of predetermined size, each of which represents a target nucleic acid sequence present in the sample. In some embodiments, In some embodiments, the extension step produces extended splint molecules whose predetermined and discrete lengths are characteristic of the target nucleic acid molecule to which they correspond.

An important feature of those aspects and embodiments related to splint molecules is that the extended splint molecules, not the original cDNA molecules or target DNA molecules, are the basis for subsequent amplification and detection steps in the methods described herein.

In some embodiments of these aspects and all such aspects described herein, the methods can further comprise amplification methods known to one of skill in the art, whereby the various surrogate markers derived from different target nucleic acids in the sample, i.e., the extended prosthetic molecules or the extended splint molecules, undergo one or more rounds of nucleic acid amplification to produce a plurality of amplicons of different lengths, each such amplicon indicating the presence of one particular target nucleic acid in the original sample. In some embodiments, the amplification step helps to further provide a measure or determination of the amount or quantity of this target nucleic acid sequence that was present in the original sample. Such amplification and quantification methods include, for example, polymerase chain reaction (PCR), strand-displacement amplification (SDA) or rolling circle amplification (RCA) methods.

Preferably, the amplification method used in the various aspects and embodiments of the methods described herein is polymerase chain reaction. This requires both forward and reverse primers. For both extended prosthetic molecules and extended splint molecules, when a target nucleic acid molecule is an RNA sequence, such as an mRNA sequence, microRNA sequence, or any other class of RNA molecule, a target-specific reverse primer can be used that is identical in sequence, or comprises a sequence at the 3' end of the reverse primer identical in sequence, to the target-specific primer used for the initial reverse transcription step. Alternatively, in embodiments in which the priming of cDNA synthesis from target RNA molecules is accomplished using random hexamers or "background priming" as described herein, which can result in the extended expander oligonucleotides corresponding to any given target RNA molecule having different lengths and 3'-ends, reverse primers can be selected such that amplified copies of these extended expander oligonucleotides have common 3'-ends, and the amplification products from any given target RNA molecule will all be of the same size. The nature of the forward primers will depend on whether the method being used involves splint molecules or prosthetic molecules, and on the design of these molecules. For amplification of extended splints, the forward primers used in the amplification steps can be target-specific sequences complementary to the 5'-ends of the various splint molecules Alternatively, in some embodiments, multiple splint molecules used in a reaction are designed to further comprise a common sequence present at their 5'-ends, upstream or 5' of their unique replica sequences. In such embodiments, a common forward primer can be used for the amplification of all extended splint molecules. In those embodiments where this strategy is adopted, however, the length of the replica sequence in each splint molecule should preferably exceed the average length of the nucleic acid fragments derived from the corresponding target nucleic acid sequence, to ensure that the splint molecule is long enough to serve as a template for extension of the nucleic acids copied from these fragments.

Similarly, in some embodiments, multiple prosthetic molecules are designed to have a common sequence present at their 5'-ends, upstream or 5' of their spacer sequences. For amplification of extended prosthetic molecules in such embodiments where the prosthetic molecules all comprise a common primer sequence at the 5'-end, i.e., upstream of the spacer sequence, the same forward primer can be used for all extended prosthetic molecules being amplified.

To allow detection of the amplification products of either extended splints or extended prosthetic molecules, one of the primers, preferable the reverse primer, can be labeled with a fluorescent dye, such as FAM. The detection and quantification or quantification steps can further comprise, in some embodiments, real-time PCR as taught, for example, in U.S. Pat. Nos. 5,210,015, 5,487,972, 5,804,375, 5,994,056, 5,538,848 and 6,030,787. Accordingly, in some embodiments, the amplified surrogate markers or amplicons, such as extended prosthetic molecule amplicons or extended splint molecule amplicons, each corresponding to a specific target nucleic acid sequence, can be separated by methods providing size discrimination such as electrophoresis or chromatography, as described herein, which can be further coupled, in some embodiments, with detection by, for example, fluorescence detection.

The methods described herein are adapted to provide analysis of two or more species (i.e., a plurality, e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 75, at least 100, at least 250, at least 500, at least 1000, or more) of target nucleic acid sequences in a single sample, such as, for example, target RNA sequences and/or target DNA sequences having undergone partial degradation, by varying the length of the splint molecules or the prosthetic molecules or amplicons generated from them, such that each splint molecule, prosthetic molecule, extended splint molecule, extended prosthetic molecule, extended splint molecule amplicon, and/or extended prosthetic molecule amplicon has a predetermined length characteristic for one of the target nucleic acid species of interest. When multiple species of nucleic acid targets are used as templates for producing surrogate markers in accordance with the methods described herein, the lengths of the surrogate markers generated by the extension steps following hybridization of the splint molecules or prosthetic molecules to their specific target nucleic acids or corresponding cDNA molecules differ. The separation of the surrogate markers and/or amplification products thereof according to size allows for the identification of the distinct surrogate markers, thereby identifying or indicating the presence of the corresponding target nucleic acid species in the starting nucleic acid sample. In preferred embodiments of these aspects, the relative sizes of the surrogate markers or surrogate marker amplicons thereof are distinguishable by electrophoresis or capillary electrophoresis.

The components and steps of the methods described herein are provided in more detail below.

Samples

For the methods described herein, a nucleic acid sample, such as a sample comprising multiple target DNA molecules and/or target RNA classes, e.g., mRNA, microRNA, tRNA, etc., or a sample comprising such nucleic acid molecules in a partially degraded form, is provided that is suspected to or presumed to contain, comprise, or be comprised by the particular target nucleic acid sequences of interest, i.e., specific, target nucleic acid species or sequence. Such a sample includes, for example, a cellular extract, a tissue extract, or a fluid extract, isolated or obtained from an individual(s) or organism, or a formalin-fixed, paraffin-embedded (FFPE) material or sample, or any polynucleotide(s) purified or isolated from such materials, cellular, tissue or fluid extracts, including, but not limited to, skin, plasma, serum, spinal fluid, lymph fluid, synovial fluid, urine, tears, blood cells, organs, tumors, and also to samples of in vitro cell culture constituents (including, but not limited to, conditioned medium resulting from the growth of cells (including prokaryotic and eukaryotic cells) in cell culture medium, recombinant cells, and cell components). In regard to those embodiments relating to FFPE samples, these samples can comprise cellular or tissue extracts or explants obtained from an individual or organism during a medical procedure or intervention, such as surgical procedures, or biopsies. Nucleic acid samples from environmental sources, including those that have undergone partial, substantially random degradation, are also contemplated as samples for use with the methods described herein.

In most instances, there will need to be a step(s) of isolating the nucleic acid molecules comprising, e.g., multiple target DNA molecules and/or target RNA classes, or such partially degraded products of such target nucleic acid molecules, from a given sample source, to provide target nucleic acid sequences of interest in a form accessible to performing the methods described herein. Typically, in regard to those nucleic acid samples obtained from formalin-fixed, paraffin-embedded (FFPE) materials or samples, these methods of isolation comprise "deparaffinisation," whereby the paraffin present in a sample is dissolved in a solvent, such as xylene, and/or cell lysis, followed by purification of the partially degraded nucleic acid molecules by standard methods known to one of skill in the art, such as phenol/chloroform extraction, electrophoresis, and/or chromatography. Often, such methods can include a step wherein the nucleic acid molecules are precipitated, e.g., with ethanol, and resuspended in an appropriate buffer for subsequent reaction steps, for example, cDNA synthesis or other reactions, as described herein.

In some embodiments, the isolation steps do not comprise any step of isolating a specific type of nucleic acid, i.e., DNA or RNA, or a specific class of RNA molecule, e.g., mRNA, microRNA, tRNA, etc. In other words, in some embodiments, the isolation steps do not distinguish between different types or classes of nucleic acids, such that the nucleic acids used in subsequent steps comprise most, if not all, the types and classes of nucleic acids found in the original sample.

In other embodiments, the isolation steps can comprise one or more additional steps to further purify the nucleic acid sample. For example, step(s) to isolate or purify all or most classes of RNA molecules, but no DNA molecules. In other embodiments, the one or more additional steps to further purify the nucleic acid sample can be used to isolate or purify a specific class of nucleic acid, e.g., only mRNA molecules, only tRNA molecules, only microRNA molecules, etc.

Following such isolation and/or purification steps, in those embodiments of the aspects described herein where one or more target nucleic sequences is an RNA sequence, an isolated/purified sample comprising, e.g., DNA and multiple RNA classes, multiple RNA classes, or partially degraded nucleic acids, is first reverse transcribed into one or more cDNAs, as described herein. In some embodiments, following the reverse transcription steps, a sample can be treated to remove the starting RNA template sequences, using any suitable method, including physical, chemical, or enzymatic means, which are known to those of skill in the art, to separate hybridized nucleic acid strands. A preferred physical means for strand separation involves heating the nucleic acid until it is completely (>99%) denatured. Typical heat denaturation involves temperatures ranging from about 80° C. to about 105° C., for times ranging from a few seconds to minutes. Such denaturing methods also kill or terminate any reverse transcriptase activity present in the sample. In some embodiments, RNA-specific degrading enzymes can be used to degrade any RNA remaining following cDNA transcription, such as RNase H.

In some embodiments of the various aspects described herein, two or more target nucleic acid sequences, such as target DNA and target RNA sequences, including RNA sequences of the same or different classes from one or more sample sources are analyzed in a single reaction. In some applications, a single target nucleic acid sequence is screened for and identified in a plurality of samples obtained from a multitude of sources by using different sized expander oligonucleotide molecules, each of which comprise the same replica sequence identical or substantially identical to the target nucleic acid sequence of interest, such that each expander oligonucleotide, upon extension, generates a different-sized surrogate marker or extended expander oligonucleotide that corresponds to a specific sample or source, i.e., the presence or absence of a single target nucleic acid sequence, e.g., a disease marker, in various sources can be determined, and analyzed simultaneously.

In other applications, a plurality of surrogate markers, each of which comprises a different replica sequence identical to or substantially identical to at least a portion of a different target nucleic acid sequence of interest, i.e., the mirrored portion, can be generated from a single sample or individual, thereby allowing the assessment of a variety of target nucleic acid sequences in a single sample, e.g., to simultaneously screen for a multitude of disease markers in an individual. Any of the above applications can be easily accomplished using the methods described herein.

Reverse Transcription Primers, Primers, & Expander Oligonucleotides

Isolated and/or purified nucleic acid molecules from a sample, including, but not limited to, DNA molecules and RNA molecules of different classes, RNA molecules of multiple RNA classes alone, or partially degraded fragments thereof, are incubated with preselected oligonucleotide reverse-transcription primers under hybridization conditions that permit the binding of the primers to the RNA molecules, in those embodiments of the aspects described herein where at least one target sequence is a target RNA sequence. As known in the art, where reverse transcription of an RNA sequence is desired, the reverse-transcription primers are selected so that their relative positions along an RNA sequence are such that an extension product comprises a DNA sequence complementary to the target RNA sequence, i.e., a "complementary DNA" or "cDNA." Accordingly, optimal oligonucleotide reverse-transcription primers for use with the methods described herein should hybridize efficiently to the target RNA sequence of interest with negligible hybridization to other RNA sequences present in a sample. That is, hybridization should be specific for a target sequence, and not, under the same conditions, hybridize to other sequences.

As used herein, a "primer" refers to any polynucleotide sequence that hybridizes to a sequence on a target nucleic acid template and serves as a substrate or point of initiation of nucleic acid synthesis. In the methods described herein, a "reverse transcription primer" is a component in a cDNA synthesis reaction that participates in the synthesis of a complementary DNA molecule from a target RNA sequence. The length 'n' of the reverse transcription primer used helps determine the final length of the surrogate marker generated using the methods described herein. The reverse transcription primer must be sufficiently long to prime the synthesis of cDNA products in the presence of the agent for polymerization, i.e., the polymerase comprising reverse transcriptase activity. The exact length and composition of the reverse transcription primer can depend on many factors, including temperature of the annealing reaction, source and composition of the primer, and ratio of primer:template concentration. In some embodiments of the aspects described herein, a "reverse transcription primer" can be a "gene-specific reverse transcription primer" or "target RNA-specific reverse transcription primer" such that the primer is designed to be specific for one RNA target sequence being detected using the methods described herein, i.e., the primer comprises a sequence complementary to at least part or a portion of the target sequence of interest. In such embodiments where target RNA-specific reverse transcription primers are used, the cDNA molecules synthesized from the sample, such as, for example, a sample comprising multiple RNA classes or a sample comprising, in part, degraded nucleic acid molecules, are all complementary to specific target RNA sequences of interest, depending on the number of gene-specific reverse transcription primers used. Such gene-specific and target RNA-specific reverse transcription primers are useful in those applications of the methods described herein where it is desirable to analyze or detect a specific panel of RNA target sequences of interest. For example in those embodiments when a specific set of RNA target sequences is used as a panel of biomarkers to determine whether the individual or patient from which the sample is derived has a disease or condition characterized by expression of those target RNA molecules.

In certain embodiments of the various aspects described herein, a "reverse transcription primer" can be a "random hexamer." As used herein, "random hexamer primers" refer to short oligonucleotides of random sequence ($d(N)_6$) that anneal randomly to complementary sites on the RNA molecules present in a sample. By using random hexamer primers to initiate reverse transcription, efficient conversion of the entirety of the RNA molecules present in a sample can be achieved, in those embodiments of the methods described herein where it is desired that, as far as possible, all RNA molecules present in a sample are reverse-transcribed. In those embodiments where random hexamers are used as reverse transcription primers in the methods described herein, the random hexamers are preferably removed, using, for example, a thermolabile single-stranded nuclease, prior to the addition of the splint molecules or prosthetic molecules.

In other embodiments of the aspects described herein, RT priming can commence from random priming events by nucleic acids (RNAs or DNAs) already present in the sample in a process referred to herein as 'background priming,' as described in Frech, B. and Peterhans, E. (1994) RT-PCR: 'background priming' during reverse transcription. *Nucl. Acids Res.* 22, 4342-4343, the contents of which are herein incorporated by reference in their entireties.

In some aspects and embodiments, additional steps to the methods described herein can further comprise amplification steps, such as PCR, to amplify the one or more surrogate markers generated, thus forming "surrogate marker amplicons" comprising "amplified extended splints," "extended splint amplicons," "amplified extended prosthetic molecules," or "amplified prosthetic amplicons," as the case may be. Such amplification steps can further comprise the use of additional oligonucleotide primer pairs, i.e., sets of "forward" and "reverse" primers, as further described herein. The length and sequences of primers for use in PCR can be designed based on principles known to those of skill in the art, see, e.g., Innis M A and Gelfand D H (1990; "Optimization of PCRs." In: PCR protocols. A guide to methods and applications. Academic Press, Inc, Chapter 1:3-12.).

Oligonucleotide primers for use in the methods described herein can be prepared using any suitable method known to those skilled in the art, such as, for example, methods using phosphotriesters and phosphodiesters. In some embodiments, one or more phosphorothioate linkages can be included in the primers. The oligonucleotide primer can also be modified at the base moiety, sugar moiety, or phosphate backbone with minor groove binders, intercalating agents and the like, so long as its ability to specifically bind template and serve as substrate for polymerase extension (for those embodiments requiring extension) are maintained.

The primers for the cDNA synthesis and/or amplification reactions can be designed according to known algorithms. Where amplification is desired, the primers are designed to hybridize to sequences that flank the target nucleic acid sequence being amplified, i.e., a "primer pair." Typically, commercially available or custom software use algorithms to design primers such that the annealing temperatures of the primers are close to melting temperature. Primers can be of a variety of lengths and are preferably less than 50 nucleotides in length and greater than 6 nucleotides in length, preferably 6-35 nucleotides, more preferably 12-30 nucleotides, and most preferably 15-25 nucleotides in length. Oligonucleotide primers are usually at least 6 bases, at least 8 bases, at least 10 bases, at least 12 bases, more often about 15 bases, about 16 bases, about 17 bases, about 18 bases, about 19 bases, about 20 bases, about 21 bases, about 22 bases, about 23 bases, about 24 bases, or about 25 bases in length. Primers are typically designed so that all primers participating in a particular reaction have melting temperatures that are within 10° C., preferably within 5° C., and most preferably within 2° C. of each other. Primers are further designed to avoid priming on themselves or another primer as templates in a reaction, and to avoid intra- and intermolecular complementarity. In some embodiments, the oligonucleotide primers for use in the methods described herein have a GC content similar to that of the template nucleic acid. It is preferred that oligonucleotide primers do not comprise unusual sequence runs, such as stretches of polypurines or polypyrimidines, as such stretches can result in secondary structures that inhibit amplification steps, such as PCR. It is also preferred a given set of oligonucleotide primers do not have complementarity to each other in their 3' ends.

The primers must be sufficiently complementary to their respective target nucleic acid strands to anneal or hybridize selectively and form stable duplexes. In some embodiments, oligonucleotide primers are designed to be exactly complementary to a target nucleic acid sequence. In other embodiments, base-pair mismatches or sites of non-complementarity can be included, e.g., to detect gene homologs where sequence information is lacking. In those embodiments where one or more mismatches are to be included in an oligonucleotide primer or primer set, it is preferred that the mismatches or non-complementary sites occur at the 5' end of the primer, as the closer a mismatch is to the 3' end of a primer, the more likely it is to prevent extension of the annealed primer.

As understood by one of skill in the art, when a DNA molecule is said to be "complementary" to an RNA sequence, any C, G, or A nucleotides on the RNA molecule is base-paired with the complementary G, C, and T, respectively, on the DNA molecule, while any U nucleotides on the RNA molecule are base-paired with A nucleotides on the DNA molecule. In some embodiments of the methods described herein, a primer can comprise a 5' end sequence of "n" nucleotides that is not complementary to a target sequence and a 3' end that is highly complementary to or exactly complementary to a target nucleic acid sequence, such that extension of the primer hybridized to a target RNA or DNA sequence generates a product comprising an extra "n" nucleotides.

In the case of an amplification reaction, primer concentrations should be sufficient to bind to the amount of target sequences that are amplified so as to provide an accurate assessment of the quantity of amplified sequence. Those of skill in the art will recognize that the amount or concentration of primer should vary according to the binding affinity of the primers as well as the quantity of sequence to be bound. Typical primer concentrations range from, for example, 0.01 µM to 1.0 µM in a reaction.

The cDNA synthesis and amplification reactions described herein are performed under conditions in which the primers hybridize to the target sequence template, i.e., RNA or DNA template, and are extended by a polymerase. As appreciated by those of skill in the art, such reaction conditions can vary, depending on the target nucleic acid of interest and the composition of the primer. cDNA synthesis and amplification reaction cycle conditions are selected so that the primers hybridize specifically to the target template sequence and are extended, if the appropriate polymerase is present. Primers that hybridize specifically to a target template enable amplification of the target sequence preferentially in comparison to other nucleic acids that can be present in the sample that is analyzed.

Prosthetic Molecules

One key and distinguishing feature of the aspects and embodiments of the methods described herein is the use of oligonucleotides, preferably single-stranded DNA oligonucleotides, termed "prosthetic molecules" or "prosthetic oligonucleotides" to generate surrogate markers of predetermined sizes, and in some embodiments, predetermined and discrete sizes, referred to herein as "extended prosthetic molecules," for a target nucleic acid sequence or plurality of target nucleic acid species present in a sample.

As described herein, through the use of these prosthetic molecules, nucleic acids that are short, and/or are heterogeneous with respect to their lengths, and/or are heterogeneous with respect to their 3'-ends, and/or comprise unknown sequence at their 3'-ends, and/or derived from multiple different target nucleic acid sequences and/or multiple different RNA classes, can be converted into homogeneous populations of extended prosthetic molecules such that the extended prosthetic molecules corresponding to a particular target nucleic acid sequence or corresponding cDNA molecule all have the same length. In some embodiments, the length of the extended prosthetic molecules corresponding to a particular target nucleic acid sequence or corresponding cDNA molecule is different from that of the extended prosthetic molecules corresponding to any other target nucleic acid sequence or corresponding cDNA molecule. In other words, as described herein, each target nucleic acid sequence or corresponding cDNA molecule acts as a template that is then copied into an amplifiable substrate using a prosthetic molecule of a characteristic length with the prosthetic molecule providing a 3' end for extension by a template-dependent polymerase.

As used herein, a "prosthetic molecule" comprises, in 5' to 3' order, (i) a spacer sequence of defined length, and (ii) a replica sequence identical or substantially identical to at least a portion of the target nucleic acid that the prosthetic molecule is designed to detect. In those embodiments of the aspects described herein, where the prosthetic molecule detects a target RNA sequence, the 3' end of the mirrored sequence of the target RNA sequence to which the replica sequence is substantially identical is 5' of the RT primer site on the target RNA molecule. In some preferred embodiments of the aspects described herein, the prosthetic molecule further comprises, 5' of the spacer sequence of defined length, a forward primer sequence that is identical to or which comprises a sequence identical to the forward primer sequence used for any subsequent amplification steps. Thus, these prosthetic molecules are designed so that each one comprises a replica sequence that is substantially identical to the mirrored portion of one of the target nucleic acid sequences, and, upon extension by a template-dependent polymerase, generates a surrogate marker of a predetermined length, and, in some embodiments, predetermined and discrete length. The length of the replica sequence is sufficient to ensure that, under stringent annealing conditions, the prosthetic molecule hybridizes specifically to the target nucleic acid molecule or corresponding cDNA sufficiently to permit extension by a template-dependent polymerase. As also explained elsewhere herein, when two or more sequences are said to be substantially identical, the sequences comprise the same order or sequence of nucleotides, but can utilize different nucleotide components (e.g., ribonucleotides vs. deoxyribonucleotides) and consequently use different bases at some positions. Size-based separation techniques can then be employed to distinguish the extended prosthetic molecules that are produced, and thereby to identify and/or quantify the target nucleic acid sequences of interest in a given sample. An exemplary prosthetic molecule-related embodiment is illustrated in FIG. 1.

In some embodiments, any extended prosthesis surrogate marker produced upon hybridization and extension of the prosthetic molecule is different in length from other extended prosthesis surrogate markers generated in the reaction, i.e., has a predetermined and discrete size. The extended prosthesis surrogate markers are preferably at least 100 nucleotides in length. In some such embodiments, to distinguish between different target nucleic acid sequences or species of interest, each prosthetic molecule is designed with a predetermined and specific total length. In some embodiments, the spacer sequences in different prosthetic molecules, each of which is specific for a different target nucleic acid species, are of different, discrete lengths, allowing the surrogate markers generated upon extension and/or amplification of the prosthetic molecules to be distinguished from one another, and thus to identify each target nucleic acid species present in a sample.

In other embodiments, the primers used in subsequent amplification steps to generate extended prosthetic molecules amplicons generate or determine the discrete length. In other words, in such embodiments, extended prosthesis surrogate markers produced upon hybridization and extension of the prosthetic molecules can be of the same predetermined length, and only the extended prosthetic molecules amplicons are of discrete lengths.

In those embodiments of the aspects described herein where the prosthetic molecule further comprises, 5' of the spacer sequence of defined length, a forward primer sequence that is identical to or which comprises a sequence identical to the forward primer sequence used for any subsequence amplification steps, this forward primer sequence of each prosthetic molecule sequence in a reaction is the same, i.e., the forward primer used in subsequent amplification steps is the same for all the prosthetic molecules. In other embodiments, the forward primer sequences within the various prosthetic molecules in a reaction can be different in sequence and/or length from one another.

Numerous factors influence the efficiency and selectivity of hybridization of a prosthetic molecule to the target nucleic acid or corresponding cDNA molecule. These factors, which include template or target length, nucleotide sequence and/or composition, hybridization temperature, buffer composition and potential for steric hindrance in the region to which the prosthetic molecule is required to hybridize, are considered when designing prosthetic molecules useful for the methods described herein. Prosthetic molecules useful in the methods described herein form hybrids that have a particular melting temperature ($T_m$) that can be useful in predicting or maximizing specificity. $T_m$ can be estimated using, e.g., commercial programs, including, e.g., Oligo-dT Obliged, Primer Design and other programs available on the world wide web, including Primer 3 and Oligo Calculator. Preferably, the $T_m$ of a hybrid duplex formed by a prosthetic molecule useful in the methods described herein, or more particularly the $T_m$ of the hybrid formed by the replica sequence of the prosthetic molecule and the cDNA molecule to which it is hybrizided, is between about 45 and 65° C., and more preferably between about 50 and 60° C.

For those embodiments where at least one target nucleic acid molecule is a target RNA sequence, as illustrated in FIG. 1, which shows a schematic of an embodiment using prosthetic molecules, following reverse-transcription and generation of a population of complementary DNA molecules of different lengths for each target RNA sequence of interest, a prosthetic molecule or plurality of prosthetic molecules of predetermined and, in some embodiments, discrete lengths, is added. Each prosthetic molecule is complementary to at least a part of a sequence of a specific target nucleic acid or corresponding cDNA of interest, i.e., comprises a replica sequence that is substantially identical to the mirrored portion of the target nucleic acid sequence, such that the replica sequence is at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, or more. In those embodiments of the methods described herein where the nucleic acid sample comprises partially degraded nucleic acid molecules, including partially degraded RNA molecules, the length of each target nucleic acid or corresponding cDNA molecule to which a given prosthetic molecule is complementary is dependent on the degree of degradation the original nucleic acid sample, or sample comprising partially degraded nucleic acids, underwent, i.e., the number of breaks in the nucleic acid molecule comprising the target nucleic acid sequence of interest. Thus, a given prosthetic molecule sequence can bind, anneal, or hybridize to a plurality of target nucleic acid or corresponding cDNA molecule sequences comprising part or all of a sequence of the target nucleic acid or corresponding cDNA sequence of interest.

In those embodiments where at least one target nucleic acid molecule is a target RNA sequence, the prosthetic molecule specific for the target RNA sequence is designed such that 3'-end of the replica sequence, which is at the 3' end of the prosthetic molecule, is just proximal to (i.e., just 5' of or 1 base pair upstream of) the 5' end of the RT primer site in the target RNA sequence. In other words, the 3' end of the mirrored portion on the target RNA, to which the replica sequence of the prosthetic molecule is substantially identical, is just proximal, or 1 base upstream of the RT primer site on the target RNA sequence. In other embodiments where at least one target nucleic acid molecule is a target RNA sequence, the 3' end of the replica sequence, which is at the 3'-end of the prosthetic molecule, is not exactly proximal to the 5' end of the RT primer site. That is, there can be a gap between the 3' end of the prosthetic molecule and the 5' end of the RT primer site on the target RNA sequence.

Following hybridization of a prosthetic molecule to a target nucleic acid or corresponding cDNA molecule comprising a complementary sequence during the course of the methods described herein, the prosthetic molecule is extended, as illustrated in the embodiment shown in FIG. 1, using a template-specific polymerase, e.g., DNA polymerase, such as Taq polymerase. In those embodiments where at least one target nucleic acid molecule is a target RNA sequence, and in which the 3'-end of mirrored portion of the target RNA sequence is immediately adjacent to the 5'-end of the RT primer site, extension of the hybridized prosthetic molecule generates an extended prosthesis the length of which is equal to the length of the prosthetic molecule and the length, "n," of the reverse-transcription primer used during the cDNA synthesis step, i.e., "prosthetic molecule length+n." Any gap of "y" nucleotides between the 3'-end of the mirrored portion of the target RNA sequence and the RT primer site will increase the length of the extended prosthesis by an additional 'y' nucleotides. In other words, in those embodiments where at least one target nucleic acid molecule is a target RNA sequence and the 3' end of the replica sequence of the prosthetic molecule is not exactly proximal to the 5' end of the RT primer site, an extended prosthesis is generated where its length is equal to the length of the prosthetic molecule plus the length, "n," of the reverse-transcription primer used during the cDNA synthesis step, plus the length of the gap "y" i.e., "prosthetic molecule length+n+y." In some embodiments, through the use of prosthetic molecules with spacer sequences of different lengths, as illustrated in FIG. 1, extended prosthetic molecules of different lengths characteristic for, or indicative of, different target nucleic acids can thus be generated.

Thus, while the starting nucleic acid molecules comprising target sequences, or the cDNA molecules complementary to the target RNA sequences, can have different lengths, because, for example, the nucleic acid fragments from which they were generated comprised different portions of the target sequence, following the hybridization of the prosthetic molecules and subsequent extension steps, a plurality of extended prosthetic molecules of the same size are generated from each such target nucleic acid sequence. These oligonucleotide molecules having a length equal to the "prosthetic molecule length+the reverse transcription primer length 'n,' and, in some embodiments, + the length of any gap 'y', as described above, are termed herein as "extended prosthetic molecules" and are another embodiment of "surrogate markers."

Following the extension step, the extended prosthetic molecules can then be amplified using forward and reverse primer pairs, as described later herein.

Accordingly, the result of these hybridization and polymerization steps is extended prosthetic molecules of predefined lengths. In some embodiments, each extended prosthetic molecule is of predefined and discrete length. In some further embodiments, each extended prosthetic molecule further comprises a terminal primer sequence useful for subsequent amplification steps. In other embodiments, the extended prosthetic molecules for a particular target nucleic acid can have the same predefined length as the extended prosthetic molecules for other target nucleic acids following the hybridization and polymerization steps, and only during subsequent amplification steps reach a discrete length unique for the target nucleic acid sequence of interest.

Design, detection, and/or determination of the precise sequence and length of a prosthetic molecule depends in part on the nature of the target polynucleotide sequence to which it binds, and the sequences and lengths of other prosthetic molecules present in a reaction. The binding location and length of a prosthetic molecule can be varied to achieve appropriate annealing and melting properties for a particular embodiment. Guidance for making such design choices can be found in many art recognized references.

Modifications of the primers and prosthetic molecule that can facilitate binding and hybridization to maximize the efficiency of the methods described herein include the incorporation of positively charged or neutral phosphodiester linkages in the primers and prosthetic molecules to decrease the repulsion of the polyanionic backbones of the probe and target (see Letsinger et al., 1988, J. Amer. Chem. Soc: 110: 4470); the incorporation of alkylated or halogenated bases, such as 5-bromouridine, to increase base stacking; the incorporation of ribonucleotides to force any duplexes formed into an "A" structure, which has increased base stacking; and the substitution of 2,6-diaminopurine (amino adenosine) for some, or all of the adenosines in the probe. In preparing such modified primers and prosthetic molecules, one should recognize that the rate-limiting step of duplex formation is "nucleation," the formation of a single base pair, and therefore, altering the biophysical characteristic of a portion of the primer or splint molecule, for instance, only the 3' or 5' terminal portion, can suffice to achieve the desired result.

Splint Molecules

Another key and distinguishing feature of certain aspects and embodiments of the methods described herein is the use of expander oligonucleotides, preferably single-stranded, DNA oligonucleotides, referred to as "splint molecules," to generate discretely-sized surrogate markers for a target nucleic sequence or plurality of target nucleic acid sequences or species present in a sample. These splint molecules are designed so that each one is comprised largely, i.e., at least 75%, at least 80%, at least 85%, at least 90%, at least 95%, or more, or completely (100%) of a replica sequence that is substantially identical to the desired mirrored portion of one of the target nucleic acid sequences, and upon copying and extension by a template-specific polymerase generates a surrogate marker of a predetermined size/length. In some embodiments, to distinguish between different target nucleic acid sequences of interest, each splint molecule is designed to have a predetermined and discrete specific total length, such that any surrogate marker produced upon hybridization and extension of a splint molecule is different in length from other surrogate markers generated in a given reaction, and is preferably at least 100 nucleotides in length.

Numerous factors influence the efficiency and selectivity of hybridization of a splint molecule to the target nucleic acid molecule. These factors, which include template and target length, nucleotide sequence and/or composition, hybridization temperature, buffer composition and potential for steric hindrance in the region to which the splint molecule is required to hybridize, are considered when designing splint molecules useful in the methods described herein. Splint molecules useful in the methods described herein will form hybrids with nucleic acid molecules that have a particular melting temperature ($T_m$) which can be useful in predicting or maximizing specificity. $T_m$ can be estimated using, e.g., commercial programs, including, e.g., Oligo-dT Obliged, Primer Design and programs available on the internet, including Primer 3 and Oligo Calculator. Preferably, the $T_m$ of the hybrids formed by a splint molecule useful in the methods described herein, or more particularly the $T_m$ of the hybrids formed by the replica sequence within the splint molecule, is between about 45 and 65° C., and more preferably between about 50 and 60° C.

As used herein, the terms a "splint molecule" or "splint probe" refer to a polynucleotide, preferably a DNA polynucleotide, preferably single-stranded, of predefined and specific sequence length, the greater part, i.e., at least 75%, at least 80%, at least 85%, at least 90%, at least 95%, or more) or all of which (100%) sequence comprises a replica sequence substantially identical to the mirrored portion of a specific target nucleic acid, such that the splint molecule can serve as a template for extension of nucleic acid sequences complementary to the target nucleic acid. In those embodiments relating to or comprising at least one target RNA sequence, this requires that the mirrored portion is 5' of the RT primer site within the target RNA sequence. The replica sequence of the splint molecule extends to and comprises the 3'-end of the splint molecule, and can preferably comprise at least 25 nucleotides, at least 30 nucleotides, at least 35 nucleotides, at least 50 nucleotides, at least 75 nucleotides, at least 100 nucleotides, at least 150, or at least 175 nucleotides. In those embodiments relating to target RNA sequences, the 3'-end of the splint molecule can be located immediately adjacent, on the 5'-side, to the RT primer site within the target RNA, or can even overlap such site. Alternatively, there can be a gap between the 3'-end of the splint molecule and the RT primer site within the target RNA sequence. A splint molecule can further comprise, in some embodiments, at its 5'-end, a forward primer sequence that is identical to or which comprises a sequence identical to the forward primer sequence used for any subsequent amplification steps.

The extension of a splint molecule hybridized to the mirrored portion of the target nucleic acid sequence, or to a sequence complementary to the mirrored portion of the target nucleic acid sequence, forms an extension product of predetermined length, termed herein an "extended splint" or "extended splint molecule," that provides a surrogate marker indicative of the presence of such target nucleic acid sequence(s) in a sample. In some embodiments, the extended splint molecule is of a predetermined and discrete length. In other words, the extended splint molecule is of a discrete length indicative of and unique for the target sequence of interest. In some embodiments, subsequent amplification of the extended splint molecule with appropriate primers provides a surrogate marker of predefined and discrete length that is indicative of and unique for the presence of the target nucleic acid sequence in a sample.

As illustrated in FIG. 1, in those embodiments relating to or comprising at least one target RNA sequence, following reverse-transcription and generation of a population of complementary DNA molecules for each target RNA sequence of interest, single-stranded splint molecules of predetermined and, in some embodiments, discrete lengths are added. Each splint molecule is complementary to at least a part of a sequence of a specific cDNA of interest or a target nucleic acid sequence of interest.

In those embodiments where at least one target nucleic acid molecule is a target RNA sequence, the splint molecule specific for the target RNA sequence is designed such that the 3'-end of the replica sequence, which is at the 3' end of the splint molecule, is just proximal to (i.e., just 5' of or 1 base pair upstream of) the 5' end of the RT primer site within the target RNA sequence. In other words, the 3' end of the mirrored portion on the target RNA, to which the replica sequence of the splint molecule is substantially identical, is just proximal, or 1 base upstream of the RT primer site within the target RNA sequence. In other embodiments where at least one target nucleic acid molecule is a target RNA sequence, the 3' end of the splint molecule is not exactly proximal to the 5' end of the RT primer site. That is, there can be a gap between the 3' end of the splint molecule and the 5' end of the RT primer site within the target RNA sequence.

Figure 3:
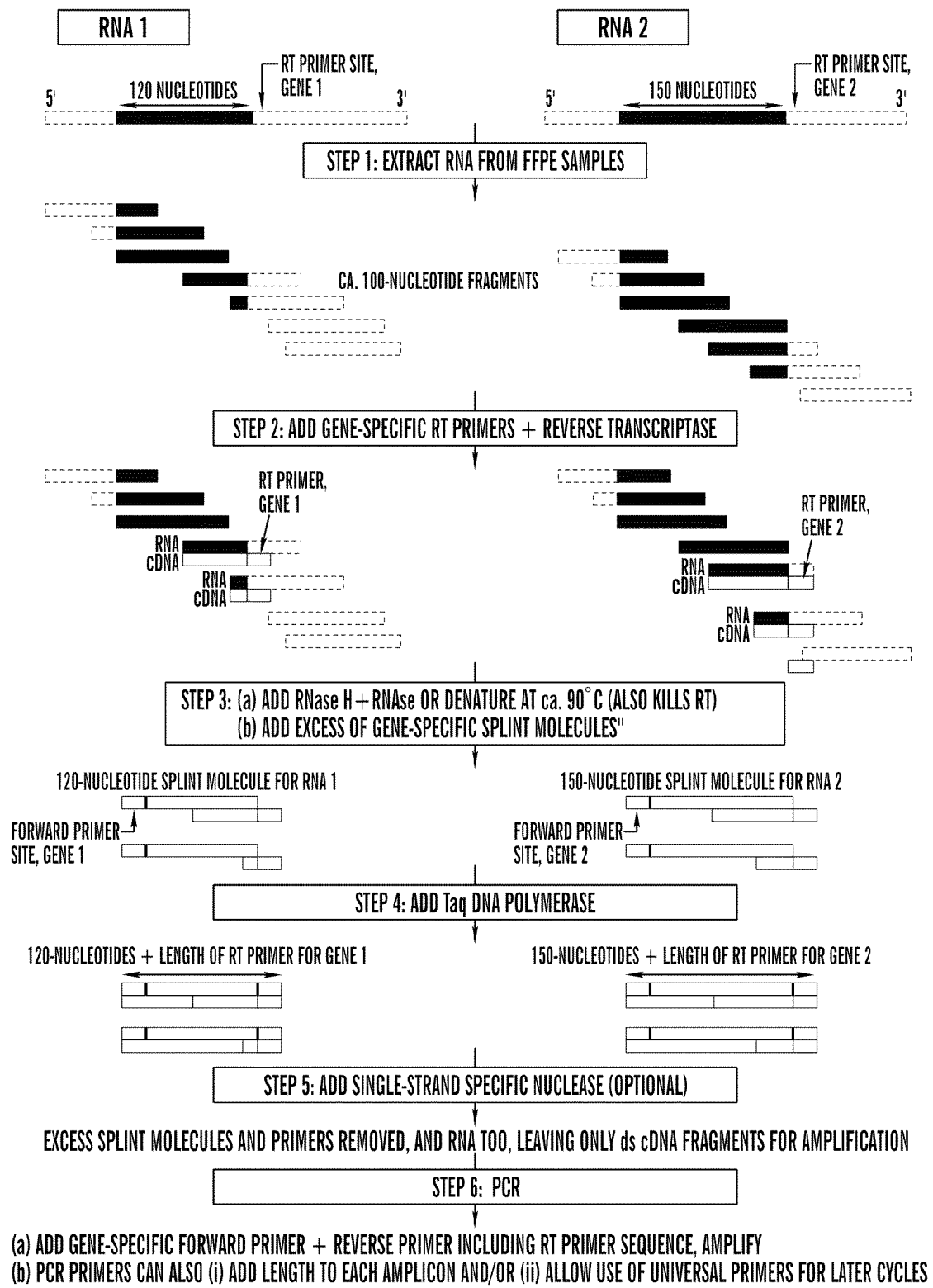
FIG. 3 depicts a multiplex expander/splint method for generating amplicons of different, predetermined lengths from a nucleic acid sample comprising RNA using an embodiment of the methods described herein. The method is well-adapted for multiplex detection and quantitation of target RNAs from degraded RNA samples, including, but not limited to FFPE RNA samples. In this schematic diagram, target regions of 120-150 nucleotides are amplified into amplicons of 120+n and 150+n respectively, where 'n' is the length in nucleotides of the target-specific reverse transcriptase primers used for initial cDNA synthesis. RNAs are shown using dotted lines for their outlines, with the solid line sections within each one indicating the mirrored portion of the target RNA sequence, which in this embodiment corresponds exactly in length with the target RNA region for amplification, and the RT primer site; in this instance, the forward primer sequence for amplification comprises part of the replica sequence of the splint molecule and the reverse primer for amplification has the same 5'-end as the RT primer.

Following hybridization to a target nucleic acid or corresponding cDNA molecule comprising a complementary sequence during the course of the methods described herein, the splint molecule is copied and extended, as illustrated in the embodiments shown in FIG. 3, using a template-specific DNA polymerase, such as Taq polymerase. In those embodiments where at least one target nucleic acid molecule is a target RNA sequence, and in which the 3'-end of mirrored portion of the target RNA sequence is immediately adjacent to the 5'-end of the RT primer site, copying and extension of both the hybridized splint molecule and the cDNA molecule generates a double-stranded DNA sequence the length of which is equal to the length of the splint molecule plus the length, "n," of the reverse-transcription primer, i.e., "splint molecule length+n." In those embodiments, where a gap of 'y' nucleotides is present between the 3' end of the splint molecule and the 5' end of the RT primer site within the target RNA sequence, this gap is bridged by the extension added to the reverse-transcription primer during the cDNA synthesis step, and the length of the double-stranded DNA sequence then generated is equal to the length of the splint molecule+ the length of the reverse-transcription primer sequence used during the cDNA synthesis step+the length of the aforementioned gap, i.e. "splint molecule length+n+y." The result of this polymerization step is an extended splint and complementary strand of predefined length. In some embodiments, the splint molecule can further comprise, at its 5' terminal end, primer sequences useful for subsequent amplification steps.

Design, detection, and/or determination of the precise sequence and length of a splint molecule depends in part on the nature of the target polynucleotide sequence to which it binds, and the sequences and lengths of other splint molecules present in a reaction. The binding location and length of a splint molecule can be varied to achieve appropriate annealing and melting properties for a particular embodiment. Guidance for making such design choices can be found in many art-recognized references.

Modifications of the primers and splint molecules that can facilitate binding and hybridization to maximize the efficiency of the methods described herein include the incorporation of positively charged or neutral phosphodiester linkages in the primers and splint molecules to decrease the repulsion of the polyanionic backbones of the probe and target (see Letsinger et al., 1988, J. Amer. Chem. Soc: 110: 4470); the incorporation of alkylated or halogenated bases, such as 5-bromouridine, to increase base stacking; the incorporation of ribonucleotides to force any duplexes formed into an "A" structure, which has increased base stacking; and the substitution of 2,6-diaminopurine (amino adenosine) for some, or all of the adenosines in the probe. In preparing such modified primers and splint molecules, one should recognize that the rate-limiting step of duplex formation is "nucleation," the formation of a single base pair, and therefore, altering the biophysical characteristic of a portion of the primer or splint molecule, for instance, only the 3' or 5' terminal portion, can suffice to achieve the desired result.

Nucleic Acid Polymerases

"Nucleic acid polymerases," as used herein, refer to a broad class of enzymes that catalyze the polymerization of individual nucleotides, e.g., deoxyribonucleotides and ribonucleotides, into a nucleic acid strand or polynucleotide in a template-dependent manner. Nucleic acid polymerases generally useful in the invention include reverse transcriptases, DNA polymerases, RNA polymerases, and mutant or altered forms of any of the foregoing. In some embodiments of the aspects described herein, the enzyme having polymerase activity can comprise a hybrid protein. The term "hybrid protein" is used herein to describe a protein that comprises amino acid residues from more than one parent sequence. Examples of hybrid polymerase proteins and methods of generating hybrid proteins are disclosed in WO2004011605, the contents of which are herein incorporated in their entirety by reference. Such polymerases are therefore non-naturally occurring variants of polymerases.

In the methods described herein, the samples comprising one or more target RNA molecules undergo cDNA synthesis using enzymes having reverse transcriptase activity. Reverse transcriptases are DNA polymerase enzymes that transcribe single-stranded RNA template to generate a "complementary DNA" strand, known as a "cDNA." Reverse transcriptase enzymes typically include an RNA-dependent DNA polymerase and a DNA-dependent DNA polymerase, which work together to perform transcription. Reverse transcriptases can thus also help in the formation of a double helix DNA, once RNA has been reverse transcribed into a single strand complementary DNA (cDNA). In some embodiments, the enzymes used in the methods described herein to convert target RNA sequences to cDNAs comprise only reverse transcriptase activity. A number of reverse trascriptases (RTases) can be used in the methods described herein. Suitable RTases are commercially available and can be employed to conduct the reverse-transcription primer extension at a range of temperatures. The examples of available RTase include, but are not limited to, AMV, MMLV and HIV reverse transcriptases, HTLV-1, HTLV-II, FeLV, My, SIV, AMV, MMTV, MoMuLV and other retroviral reverse transcriptases (see Levin, Cell 88:5-8 (1997); Verma, Biochim Biophys Acta. 473:1-38 (1977); Wu et al., CRC Crit. Rev Biochem. 3:289-347 (1975)), thermostable RTases such as ThermoScript™ RNase H-Reverse Transcriptase and Thermo-X™ Reverse Transcriptase (Invitrogen), and Transcriptor Reverse Transcriptase (Roche Applied Sciences). In addition, several thermostable DNA polymerases which display high reverse transcriptase activity such as Tht DNA Polymerase can be used to conduct reverse transcription and PCR amplification using a single enzyme. Guidance for the use of such polymerases can readily be found in product literature and in general molecular biology guides such as Sambrook or Ausubel, both supra. Polymerases can incorporate labeled (e.g., fluorescent) nucleotides or their analogs during synthesis of polynucleotides, see, e.g., Hawkins et al., U.S. Pat. No. 5,525,711.

At least five families of DNA-dependent naturally occurring DNA polymerases are known, although most fall into three families designated A, B and C. There is little or no structural or sequence similarity among the various families. As used herein, a "DNA polymerase" refers to any naturally occurring or recombinant enzyme that catalyzes the polymerization of deoxyribonucleotides into a polynucleotide DNA strand in a template-dependent manner. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In E. coli, three types of DNA polymerases have been found, DNA polymerases I (family A), II (family B), and III (family C). In eukaryotic cells, three different family B polymerases, DNA polymerases, α, δ, and ε, are implicated in nuclear replication, and a family A polymerase, polymerase γ, is used for mitochondrial DNA replication. Other types of DNA polymerases include phage polymerases.

Endogenous or naturally occurring DNA polymerases are critical for DNA replication, in which the polymerase reads an intact DNA strand as a template, and uses it as template to synthesize the new strand. The newly polymerized molecule is complementary to the template strand, and identical to the template's original partner strand. DNA polymerases can add free nucleotides only to the 3' end of the newly-forming strand, to a preexisting 3'-OH group. Therefore, DNA polymerases require a primer, splint molecule, or prosthetic molecule, as the terms are defined herein, to provide a 3'-OH end substrate at which it can add a first nucleotide. This polymerase activity results in elongation of the new strand in a 5'-3' direction. No known DNA polymerase is able to synthesize a new chain de novo.

Nucleic acid polymerases for use in the methods described herein are preferably, in some embodiments, thermostable. Among the advantages conferred by the thermostability of certain polymerases, such as Taq (*Thermus aquaticus*) DNA polymerase, is the ability to withstand the repeated heating and cooling inherent to PCR amplification reactions, and to synthesize nucleic acid strands at high temperatures. Such high temperatures prevent or do not permit hybridization of mismatched primers, and do not permit or reduce formation of regions of local secondary structure, thus increasing the efficiency and success of the synthesis.

It is preferred that DNA polymerases for use in the methods described herein have low error rates or high fidelity. As used herein, the "error rate" of a DNA polymerase refers to the number of incorrect, i.e., non-complementary base pairs, a DNA polymerase adds to a sequence being synthesized per 10000 nucleotides added per replication cycle. For example, the error rate of Taq polymerase was initially estimated at $2 \times 10^{-4}$ nucleotides/cycle (Saiki et al., 1988). Typically, polymerases with 3' to 5' exonuclease activity have low error rates, but can sometimes have decreased yields. Accordingly, in some embodiments, a polymerase for use in the methods described herein has 3' to 5' exonuclease activity. In other embodiments, the polymerase has no 3' to 5' exonuclease activity.

A wide variety of DNA polymerases can be used in the methods described herein. Suitable DNA polymerases for use in the subject methods may or may not be thermostable. DNA polymerases and their properties are described in detail in, among other places, DNA Replication 2nd edition, Kornberg and Baker, W. H. Freeman, New York, N.Y. (1991). Known conventional and/or thermostable DNA polymerases useful in the methods described herein include, but are not limited to, *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermus aquaticus* (Taq) DNA polymerase (Chien et al., 1976, J. Bacteoriol, 127: 1550), *Thermus flavus* (Tfl) polymerase (Kaledin, A. S. et al. (1981) Biokhimiia 46, 1576-84), Vent™ polymerase, Pfu polymerase, DNA polymerases derived from thermophilic microorganisms, and *E. coli* DNA polymerase I (Lecomte and Doubleday, 1983, Polynucleotides Res. 11:7505). In some embodiments, the DNA polymerase lacks 5'-nuclease activity. Examples of such polymerases include Klenow fragment of DNA polymerase 1, Stoeffel fragment of Taq polymerase, Pfu polymerase or Vent polymerase. In some embodiments, a thermoactivated DNA polymerase typically referred to as "hot-start" DNA polymerase can be used to perform extension at elevated temperatures. In addition, any mutants, variants, or fragments maintaining polymerase activity, and, when desired, thermostability, are also contemplated for use in the methods described herein.

Nucleic Acid Amplification

The methods described herein relate to the use of splint molecules and prosthetic molecules to generate surrogate markers for target sequences of interest present in a sample comprising, for example, different types of nucleic acid molecules, e.g., DNA and RNA molecules, multiple classes of RNA, and/or partially, substantially randomly, degraded nucleic acid molecules, thereby allowing size-based separation methods to detect and identify the presence and/or amount of one or more target nucleic acid sequences in the sample. These methods are especially suited for use in conjunction with a PCR-based amplification method or system, as described herein.

In some embodiments of the methods described herein, the surrogate markers of predetermined lengths, i.e., extended prosthetic molecules or extended splint molecules, indicative of the presence of one or more target nucleic acid sequences in a sample, further undergo amplification steps, thus generating surrogate marker amplicons, i.e., splint molecule amplicons, or prosthetic molecule amplicons, of different and predetermined lengths. It should be noted, as described herein, that it is possible to have splint molecules of the same size, or prosthetic molecules of the same size, yet generate surrogate marker amplicons of distinct sizes, e.g., in a multiplex reaction, by selecting primer-binding sites at different spacings on the various surrogate marker molecules, and/or by using amplification primers of different lengths for different surrogate marker molecules. The most common procedure for DNA amplification, the polymerase chain reaction (PCR) technique, is disclosed in U.S. Pat. Nos. 4,683,202; 4,683, 195; 4,800,159; and 4,965,188. The PCR method is also described in Saiki et al., 1985, Science 230:1350.

PCR provides an in vitro method for the enzymatic synthesis of specific nucleic acid sequences that uses two oligonucleotide primers that hybridize to opposite strands and flank the region of interest in the target nucleic acid sequence, i.e., a "forward" and "reverse" primer, or "primer pair." A repetitive series of reaction steps involving template denaturation, primer annealing, and the extension of the annealed primers by a DNA polymerase results in the exponential accumulation of a specific target nucleic acid fragment, the termini of which are defined by the 5' ends of the oligonucleotide primers. PCR is capable of producing a selective enrichment of a specific DNA sequence by a factor of at least $10^9$.

In a typical PCR protocol, a nucleic acid sample having a target nucleic acid sequence to be amplified is denatured by heating the sample. In the presence of a nucleic acid polymerase and excess nucleoside triphosphates, oligonucleotide primers that hybridize specifically to the target sequence can prime new nucleic acid synthesis. Generally, oligonucleotide primers are added in vast excess compared to the nucleic acid to be amplified. Under the appropriate conditions, oligonucleotide primers hybridize to opposite strands of a denatured double-stranded nucleic acid sequence and are oriented with their 3' ends facing each other on the two strands, so that synthesis by a nucleic acid polymerase that catalyzes growth of new strands in the 5' to 3' direction extends across the segment of nucleic acid between these primers.

One round of synthesis results in new strands of indeterminate length which, like the parental strands, can hybridize to the primers upon denaturation and annealing. These products accumulate only arithmetically with each subsequent cycle of denaturation, annealing to primers, and synthesis. However, the second cycle of denaturation, annealing, and synthesis produces two single-stranded products that together compose a discrete double-stranded product that is exactly the length between the primer ends. Each strand of this discrete product is complementary to one of the two primers and can therefore participate as a template in subsequent cycles. The amount of this product doubles with every subsequent cycle of synthesis, denaturation, and annealing, accumulating exponentially so that 30 cycles theoretically result in a $2^{28}$-fold (270 million-fold) amplification of the target nucleic acid product.

A typical PCR amplification cycle comprises three steps, "denaturation," "annealing" or "hybridizing," and "extension." As used herein, "denaturation" or "nucleic acid melting" refers to the separation or unwinding of double-stranded nucleic acids and separation into single-stranded strands through the breaking of hydrogen bonding between complementary bases. Both terms are used herein to refer to the process as it occurs when a mixture is heated to a specific temperature, although "denaturation" can also refer to the separation of nucleic acid strands induced by chemicals like urea. It is critical that complete strand separation occur during the denaturation step. Higher temperatures required for complete denaturation are associated with high GC content in the nucleic acids. A typical temperature for the denaturing step in a typical PCR cycle is at least 92° C., at least 93° C., at least 94° C., at least 95° C., at least 96° C., at least 97° C., at least 98° C., at least 99° C., or higher. The duration of the denaturing step in a typical PCR cycle is approximately 30 seconds.

The "annealing" or "hybridization" step of a PCR cycle refers to the step wherein the primers and/or probes stably anneal to the template. Primers with relatively low GC content (<50%) can require temperatures lower than 55° C. for full annealing. On the other hand, this can also increase the quantity of nonspecific products. For primers with high GC content, higher annealing temperatures can be tolerated. Methods for optimization of primer annealing are known to one of skill in the art. As with denaturation, the time for this step is based mainly on the time it takes to reach the proper temperature, because the primers are in such excess that the annealing reaction occurs very quickly.

The "extension" step of a PCR cycle refers to the step where the polymerase activity of a polymerase adds nucleotides to the 3'-OH of an annealed primer, thereby generating a strand complementary to the template nucleic acid. The extension temperature is chosen to be close to the optimal temperature of the polymerase being used, but is also chosen to be one at which the primers are prevented from dissociating. For example, 72° C. is close to the optimal temperature for Taq DNA polymerase (~75° C.), but is a low enough temperature to prevent annealed primers from dissociating from the nucleic acid template. Indeed, when Taq DNA polymerase is used, primer extension typically can begin during annealing, because Taq DNA polymerase is partially active at 55° C. and even lower temperatures (Gelfand, 1989). The duration of the extension step depends mainly on the length of the sequence to be amplified. Typically, a duration of 1 min per kb of target nucleic acid product length is sufficient. In some embodiments, a series of PCR cycles can end with a final and separate extension step that is longer, for example, 5-10 minutes to ensure completion of target nucleic acid product synthesis.

Accordingly, in those embodiments of the methods described herein where it is desired that a surrogate marker, such as an extended splint or extended prosthesis, undergoes PCR amplification, the following considerations specific for the amplification steps can be taken into account.

In some embodiments, in order to degrade any single-stranded sequences and prevent spurious amplification of non-surrogate markers, prior to surrogate marker amplification, a single-strand specific nuclease can be optionally added prior to the amplification steps, to degrade single-stranded molecules, such as unused reverse transcription primers, splint molecules, prosthetic molecules, or RNA molecules, present in the reaction mixture. In some embodiments, such as those relating to the use of prosthetic molecules, a single-strand-specific nuclease is not added prior to any amplification steps. In other embodiments, such as those relating to the use of prosthetic molecules, a single-strand-specific nuclease is added prior to any amplification steps.

In some embodiments of the aspects described herein, the primer pairs used in the PCR reactions comprise a forward primer comprising part of the sequence at the 5' end of the prosthetic molecule or splint molecule, and a reverse primer that is complementary to part of the 3' sequence of the target nucleic acid, i.e., the sequence 3' of the mirrored portion of the target nucleic acid. In some such embodiments, the forward primer comprises all or part of the forward primer sequence at the 5' end of the prosthetic molecule or splint molecule. In other such embodiments, the forward primer comprises part of the 5' end of the spacer sequence of a prosthetic molecule or the replica sequence of a splint molecule.

In some embodiments of the aspects described herein, where the target nucleic acid for which the expander oligonucleotide is specific is an RNA sequence, the primer pairs used in the PCR reactions can comprise a forward primer comprising part of the sequence at the 5' end of the prosthetic molecule or splint molecule, and a reverse primer that comprises all or part of the sequence of the reverse-transcription primer used in the original cDNA synthesis step. In some such embodiments, the forward primer comprises all or part of the forward primer sequence at the 5' end of the prosthetic molecule or splint molecule. In other such embodiments, the forward primer comprises sequence within the 5' end of the spacer sequence of a prosthetic molecule or the replica sequence of a splint molecule.

In some embodiments of the aspects described herein comprising amplification steps, the lengths of the surrogate marker amplicons are the same as the starting surrogate markers. In other embodiments, the surrogate marker amplicons generated upon PCR amplification of an extended splint or extended prosthesis can be longer or shorter than the original surrogate marker represented by such extended splint or extended prosthesis. The lengths are predetermined to permit identification of the given amplicon and assignment of a signal to a corresponding target nucleic acid sequence.

Figure 4:
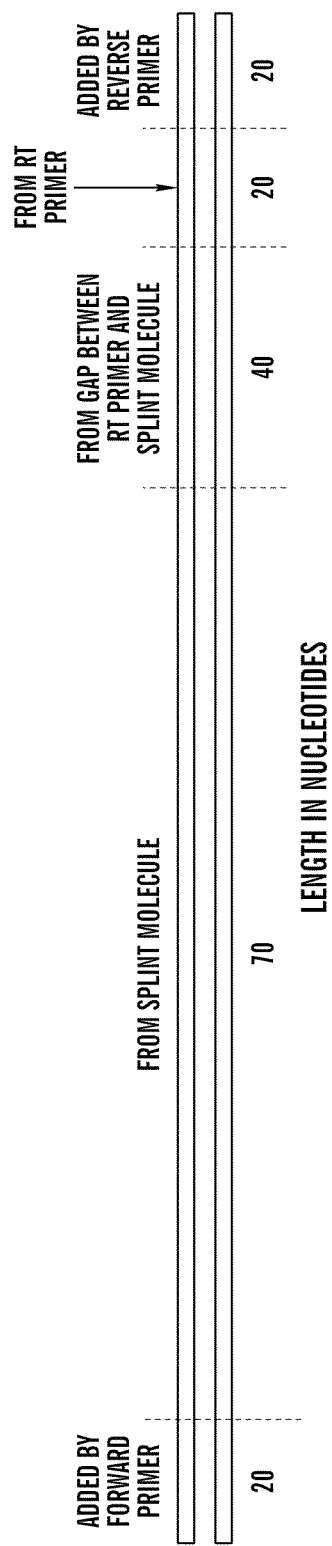
FIG. 4 depicts an exemplary surrogate marker amplicon generated using an embodiment of the methods described herein which demonstrate that if (i) the initial reverse transcription primer is 20 nucleotides long; (ii) there is a 40-nucleotide gap between the reverse transcription primer and the mirrored portion of a target RNA sequence; and (iii) the forward and reverse primers used during an amplification step add a further 40 nucleotides to the surrogate marker amplicon, then the splint molecule is only required to be 70 nucleotides long to produce a surrogate marker amplicon 170 base-pairs in length, using the methods described herein.
Figure 5:
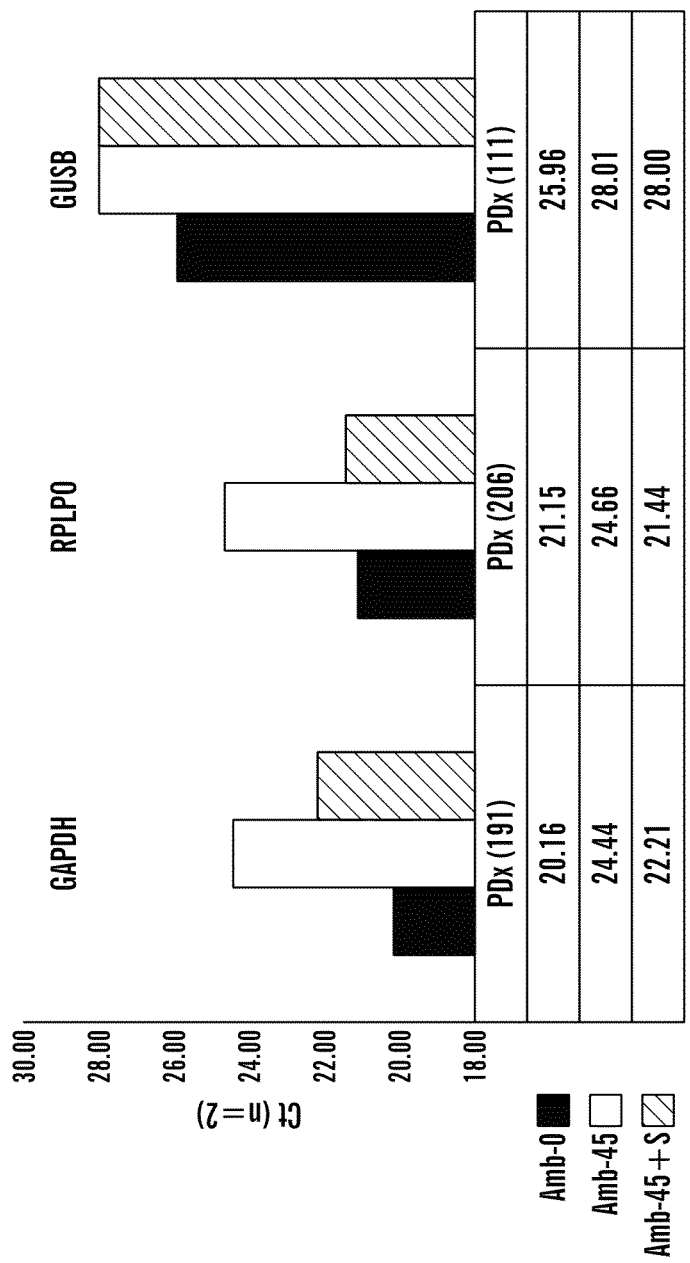
FIG. 5 demonstrates exemplary results generated using an embodiment of the methods described herein. Degraded or non-degraded RNA molecules were used as samples from which to amplify target RNA sequences ranging in length from approximately 111 to 206 nucleotides. These reactions were performed in the presence or absence of prosthetic oligonucleotide molecules. As demonstrated, addition of prosthetic oligonucleotide molecules allowed rescue of over 50% of large templates (GAP/RPL).

In some embodiments, various designs of PCR primers can be adopted to allow, for example, the addition of further length to the extended expander oligonucleotides, i.e., the extended splints or extended prosthetic molecules. If, for example, the surrogate marker indicative of a particular target nucleic acid sequence were to be amplified with 40-nucleotide-long forward and reverse primers, such that each primer comprises a 20-nucleotide "tag" sequence at the 5' end and a 20-nucleotide sequence at the 3' end specific for a sequence of the surrogate marker, the resulting surrogate marker amplicon would be 40 nucleotides longer than the original surrogate marker. Such embodiments could, in some applications, reduce the length of the expander oligonucleotide required to produce an amplicon of sufficient length for separation by capillary electrophoresis. An example of such an embodiment for those aspects relating to splint molecules is illustrated in FIG. 4, which depicts that, if (i) the initial reverse transcription primer is 20 nucleotides long; (ii) there is a 40-nucleotide gap between the 3' end of the replica sequence of the splint molecule and the 5' end of the RT primer site within the target RNA sequence; and (iii) the forward and reverse primers used in an amplification step add a further 40 nucleotides to the surrogate marker amplicon, then the splint molecule can be only 70 nucleotides long to produce a surrogate marker amplicon, i.e., an extended splint amplicon, of 170 base-pairs in length.

In other embodiments, if each of the reverse primers used for the initial round of amplification comprises a common 5' tag at the 5' end of the primer sequence, and the forward primers comprise a similar design but a different common 5' tag sequence, then subsequent rounds of amplification can be accomplished using universal forward and reverse primers complementary to the common 5' tags present in the initial primer sets. In some such embodiments, a 5' tag sequence of an amplification primer comprises at least 10 nucleotides, at least 12 nucleotides, at least 15 nucleotides, or at least 20 nucleotides.

In some embodiments of those aspects related to prosthetic molecules, each extended prosthetic molecule has a predetermined and discrete length characteristic for a particular target nucleic acid sequence, and is amplified using a specific set of primers. In such embodiments, each specific set of primers comprises a forward primer comprising part of the 5' end of the prosthetic molecule, and a reverse primer comprising a sequence complementary to part of the 3' end of the extended prosthetic molecule. In some such embodiments, where the target nucleic acid sequence is an RNA sequence, the reverse primer comprises all or part of the sequence of the target RNA-specific reverse transcription primer used in the initial reverse transcription step.

These primer pairs can be used to amplify the extended prosthetic molecules, such that annealing of the reverse primer to the extended prosthetic molecule, under the appropriate conditions for polymerase activity, first generates a strand complementary to the extended prosthetic molecule. In subsequent rounds of amplification of the extended prosthetic molecule and the strand complementary to the extended prosthetic molecule, the forward and reverse primer pairs produce amplified copies of the extended prosthetic molecule that act as a surrogate marker for the presence of the target nucleic acid sequence for which the prosthetic molecule is specific.

In some embodiments of those aspects relating to prosthetic molecules and multiplex reactions, distinction in the lengths between different amplified extended prosthetic molecules arises only from differences in their spacer sequence lengths. In some such embodiments of these aspects, the forward primer of each set of primers used during the amplification step is of the same length. In some embodiments of these aspects, the forward primer of each set of primers used during the amplification step comprises the same sequence. In some such embodiments of these aspects, the reverse primer of each set of primers used during the amplification step is of the same length.

In other embodiments of those aspects relating to prosthetic molecules and multiplex reactions, distinction in the length between different amplified extended prosthetic molecules or extended prosthetic amplicons can arise from differences in their spacer sequence lengths, as well as differences in primer lengths used during the amplification reactions. In some embodiments, the forward primer of each set of specific primers used during the amplification step is of a different, discrete length. In some such embodiments, the reverse primer of each set of primers used during the amplification step is of a different, discrete length.

In other embodiments of those aspects relating to prosthetic molecules and multiplex reactions, distinction in the lengths between different amplified extended prosthetic molecules occurs only during the amplification steps, such that the forward and reverse amplification primers add different lengths to the extended prosthetic molecules upon amplification. In some such embodiments, the forward primer of each set of specific primers used during the amplification step is of a different, discrete length. In some such embodiments, the reverse primer of each set of primers used during the amplification step is of a different, discrete length.

In some embodiments in which the priming of cDNA synthesis from target RNA molecules is accomplished using random hexamers or "background priming" as described herein, the extended expander oligonucleotides corresponding to any given target RNA molecule can have different lengths and 3'-ends, and reverse primers can be selected such that amplified copies of these extended expander oligonucleotides have common 3'-ends, and the amplification products from any given target RNA molecule will all be of the same size.

In some embodiments of these aspects and all such aspects described herein, labels or tags can be used to further aid in the detection and discrimination of the surrogate marker amplicons, e.g., amplified extended splints or amplified extended prosthetic molecules, generated using the methods described herein. Thus, in such embodiments, both size and label-specific detection methods can be used to identify surrogate marker amplicons that correspond to specific target nucleic acid sequences. Typically, a fluorescent molecule or dye is used as a label. Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein and derivatives, such as 5-bromomethyl fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, LuciferYellow, IAEDANS, 7-Me$_2$N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobiman. Other examples of fluorescent dyes for use as detectable labels in the methods described herein, can be found at, among other places, U.S. Pat. Nos. 5,750,409; 5,366,860; 5,231,191; 5,840,999; 5,847,162; 4,439,356; 4,481,136; 5,188,934; 5,654,442; 5,840,999; 5,750,409; 5,066,580; 5,750,409; 5,366,860; 5,231,191; 5,840,999; 5,847,162; 5,486,616; 5,569,587; 5,569,766; 5,627,027; 5,321,130; 5,410,030; 5,436,134; 5,534,416; 5,582,977; 5,658,751; 5,656,449; 5,863,753; PCT Publications WO 97/36960;

99/27020; 99/16832; European Patent EP 0 050 684; Sauer et al, 1995, J. Fluorescence 5:247-261; Lee et al., 1992, Nucl. Acids Res. 20: 2471-2483; and Tu et al., 1998, Nucl. Acids Res. 26:2797-2802, the contents of each of which are herein incorporated in their entireties by reference.

In addition, base-linked fluorophores and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). In some cases, base-linked fluorophores are incorporated into primers by post-synthesis modification of oligonucleotides that were synthesized with reactive groups linked to bases. The fluorophores can be attached, for example, to the 3' OH of the sugar or the base.

The literature includes references providing exhaustive lists of fluorescent and chromogenic molecules and their relevant optical properties (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949). Further, the literature provides ample guidance for derivatizing label molecules for covalent attachment via common reactive groups that can be added to an oligonucleotide (see, e.g., Haugland (supra); U.S. Pat. No. 3,996,345; and U.S. Pat. No. 4,351,760).

Methods for detecting and quantifying the amplified PCR products are well known in the art and any of them can be used in the methods described herein. Examples of such methods and systems include real-time PCR with detection of amplified nucleic acid with fluorescent dyes binding to double stranded DNA, such as SYBR Green or ethidium bromide, Real-time PCR with molecular beacons (detecting binding of fluorescently labeled probes to adjacent sequence in amplified PCR products), Real-Time PCR using a 5'-nuclease assay with Taqman probes (Applied BioSystems, Foster City, Calif.), involving Real-Time PCR thermocyclers such as the Lightcycler system from Roche (Indianapolis, Ind.), Applied Biosystems 7900HT, 7300, 7500 Real-time PCR systems (Foster City, Calif.), 1-cycler from Bio-rad (Hercules, Calif.), Rotorgene Real-time PCR cycler from Corbett (Sydney, Australia) and others.

Amplified PCR products or surrogate marker amplicons can also be separated and quantified by electrophoresis and, preferably, by capillary electrophoresis as described below.

Electrophoretic Separation Methods

Detection or verification of the surrogate markers and other reaction products, such as surrogate marker amplicons comprising amplified extended splints or amplified extended prosthetic molecules of different lengths and/or fluorescence, can be accomplished by a variety of methods and can be dependent on the label(s) employed. In some preferred embodiments of the aspects described herein, the reaction products, including any labeled surrogate marker amplicons, amplified extended splints or amplified extended prosthetic molecules, are subjected to size analysis methods. Size separation of nucleic acids is well known, e.g., by agars or polyacrylamide electrophoresis or by column chromatography, including HPLC separation. Methods for separating and detecting the presence or amount of polynucleotides are well known in the art and any of them can be used in the methods described herein so long as they are capable of separating individual polynucleotides by at least the difference in length between the various surrogate markers. It is preferred that the separation and detection permits detection of length differences as small as one nucleotide. It is further preferred that the separation and detection can be done in a high-throughput format that permits real time or contemporaneous determination of surrogate marker amplicons' abundance in a plurality of reaction aliquots taken during the cycling reaction. Useful methods for the separation and analysis of the amplified products include, but are not limited to, electrophoresis (e.g., capillary electrophoresis (CE)), chromatography (dHPLC), and mass spectrometry. A preferred approach for the aspects described herein uses capillary electrophoresis, which is both rapid and accurate, and readily achieves separation of molecules differing in size by as little as one nucleotide. Capillary electrophoresis uses small amounts of sample and is well-adapted for detection of nucleic acids by, for example, fluorescence.

Nucleic acid fragments, such as DNA fragments, have traditionally been separated and analyzed by electrophoretic methods, such as slab gel electrophoresis. Such electrophoretic techniques separate nucleic acid species based upon their size and ionic properties. An ion (i) placed in an electric field will move in the direction parallel to the field towards the oppositely charged electrode with a velocity ($v_i$) defined as follows:

$$v_i = \mu_i E = \mu_i V/L$$

where $\mu_i$ is the mobility of the ion, E is the electric field in volts per centimeter, V is the voltage across the column, and L is the total column length. The electrophoretic mobility of a given ion ($m_i$) is equal to:

$$m_i = q_i/6\pi\eta a_i$$

where $q_i$ is the charge on the ion, $\eta$ is the viscosity of the buffer or gel matrix, and $a_i$ is the radius of the ion.

In the case of slab gel electrophoretic methods, voltage applied at the ends of a gel, such as an agarose gel, generates an electric field with a strength defined by the length of the gel and the potential difference at the ends (V/cm). Nucleic acid molecules exposed to this electric field migrate toward the anode due to the negatively charged phosphates along the nucleic acid backbone. The migration velocity is limited by the frictional force imposed by the gel matrix. While charge and/or size can affect the rate at which macromolecules will pass through a gel, the charge to mass ratio is the same for DNA molecules of different lengths. It is generally the size of the DNA, therefore, that determines the rate at which it passes through the gel, thereby allowing an effective separation of DNA fragment-length mixtures by electrophoresis. It is noted that fluorescent labels can have effects on nucleic acid migration, but the influence of the label generally diminishes with increasing fragment size, particularly where labeled primers are used. Gel matrices are usually either polyacrylamide or agarose, and separations can be achieved in the presence (e.g., for ssDNA) or the absence (e.g., for dsDNA) of dissociating agents, such as urea or formamide. Such slab gel systems can analyze multiple samples in the same separation (i.e., gel(s)) at low cost, but normally take several hours to complete. The nucleic acid fragments or DNA are typically visualized with stains, UV shadowing, intercalating dyes, such as ethidium bromide, incorporated fluorescent labels, and sometimes radioactive labels.

Capillary electrophoresis (CE) is a very powerful electrophoretic method for the separation of nucleic acid fragments. CE can be performed by methods well known in the art, for example, as disclosed in U.S. Pat. Nos. 6,217,731; 6,001,230; and 5,963,456, the contents of each of which are herein incorporated in their entireties by reference. CE offers a number of advantages over slab gel separations in terms of speed, resolution, sensitivity, and data handling. This is, in part, because the CE separation occurs inside a small-diameter (50- to 100-µm) quartz capillary in the presence of high (kilovolt-level) separating voltages. Separation times are generally only a few minutes. The nucleic acid fragments can be detected, for example, by UV absorption or by fluorescent labeling, both of which eliminate the need to use mutagenic substances (e.g., ethidium bromide) or dispose of radioactive waste. The quantity of DNA required for the separation is in the nanogram range. Single-base resolution can be readily obtained on fragments up to several hundred base pairs in size. In the presence of appropriate standards, fragments can be accurately sized, based on relative electrophoretic mobility. Multicapillary automated instruments using laser fluorescence detection systems based on CE have also been developed, and are commercially available.

The separation of nucleic acid fragments by CE occurs within the walls of a capillary, such as a fused-silica capillary. Since the negatively charged nature of this surface has a dramatic impact on the resolution achieved during the separations, the vast majority of CE separations are done in "coated" capillaries whose surface has been modified to be chemically inert to nucleic acids. The capillaries are filled with a sieving matrix, and nucleic acid fragments are separated on the basis of size, analogously to slab gel separations. The sieving matrix can be a chemically cross-linked gel (static gel), such as polyacrylamide, or a flowable (non-cross-linked) polymer, such as modified cellulose or non-cross-linked polyacrylamide. Single-stranded DNA (ssDNA) fragments as small as 5 bases can be readily separated with single-base resolution. Fragments of double-stranded DNA (dsDNA) as large as 20 kb are also separated, although not with single-base-pair resolution.

The selection of the appropriate matrix can significantly affect the quality of the separation. The general rule for matrix selection is that the larger the DNA fragment, the weaker the sieving capabilities of the matrix should be. With either a cross-linked or non-cross-linked gel in the capillary, the matrix offers a frictional resistance to the movement of the DNA through the gel medium that is proportional to the size of the species. The frictional resistance can vary with the molecular weight, concentration, and chemical composition of the flowable gel polymer or the pore size in the cross-linked gel, and should be optimized for the particular size of the DNA to be separated. A detailed description of the theory of DNA motility in entangled polymer solutions can be found in Grossman (Grossman P. D. and Colburn J. C. (1992) Capillary Electrophoresis: Theory and Practice, 1sted., Academic Press, San Diego).

Cross-linked polyacrylamide is best used for the separation of synthetic oligonucleotides—both native and modified versions. However, flowable polymers can also be used for oligonucleotide analysis and for the separations of automated sequencing ladders. Where double-stranded DNA fragment analysis is required, flowable polymers are routinely used.

As used herein, "cross-linked gels" refer to fixed gels, such as polyacrylamide gel, that are polymerized inside the capillary, usually covalently bound to the capillary surface, and are not removed from the capillary between runs. Such cross-linked gels can be reused for 30 to 100 separations before losing resolution. The capillary is then discarded, since the polyacrylamide gel cannot be regenerated.

Flowable polymers have the advantage of wide fragment-separation ranges. A "flowable polymer" or "flowable polymer matrix" refers to viscous hydrophilic polymer solutions that can be pumped into a capillary, such as, but not limited to, hydroxypropyl methyl cellulose (HPMC), hydroxyethylcellulose (HEC), polyethylene oxide (PEO), or non-cross-linked linear polyacrylamide. In some embodiments, the same flowable polymer matrix can be used repeatedly when small molecules, such as synthetic oligonucleotides are being analyzed. Alternatively, the polymer can be used once, discarded, and replaced with fresh matrix prior to the next sample. This latter embodiment is preferred where larger DNA molecules are present in the samples—e.g., for fragment analysis and DNA sequencing analysis. A flowable polymer can be expelled from the capillary by pressure at the end of each electrophoretic separation; fresh matrix is then reloaded into the capillary prior to the next separation.

As noted previously, a coated capillary is usually utilized to eliminate the charge effects that are contributed by the native silica surface. With cellulose-derived polymers or some specially modified acrylamides, however, uncoated capillaries may be used, because of the strong interaction of the polymer with the inner surface of the bare fused-silica capillary, in essence forming its own coating.

Separation buffers for use in capillary electrophoretic methods are frequently variants of Tris/borate/EDTA (TBE) mixtures and are buffered at alkaline pH. Urea (e.g., 6 to 8 M) is often included in the buffer, as a denaturant, that keeps the DNA in single-stranded conformation when required, such as when analyzing ssDNA (e.g., synthetic oligonucleotides). Urea can be omitted from the buffer for analyses where secondary structure plays an important role in the separation, e.g., single-nucleotide polymorphisms or conformational polymorphisms. Samples are loaded onto the capillary by electrokinetic, or pressure, injection. Separation times range from 10 to 45 min, at voltages between 1 and 10 kV.

CE separation in its simplest form can be achieved by passing a high voltage between two buffer reservoirs that are joined by a fused silica capillary filled with liquid or gel. This results in an electric field that drives the nucleic acid molecules of interest from one end of the capillary to the other. The capillaries are preferably 20 to 80 cm long and 50 to 100 µm in internal diameter, with total volumes in the 1- to 2-µl range. The combination of high field strength and large surface-area-to-volume ratio of the capillaries results in rapid and very efficient separations of, for example, both ssDNA and dsDNA. Sample loading can be accomplished from as little as 1 µl, with starting sample concentrations of ~1 µg/ml for UV detection and ~1 pg/ml or less for laser-induced fluorescence detection. The capillaries are preferably thin walled, which allows for dissipation of the Joule heating resulting from the high voltages (10 to 30 kV) that are necessary for high-performance electrophoretic separations. The fused-silica capillary can be coated on the outside with a polyimide layer that eliminates oxidation of the fused-silica glass and confers tensile strength to the capillary. The polyimide sheathing can be carefully removed from a small portion of the capillary to expose a section of the silica. This clear section of the capillary can be inserted into the light path of a UV or fluorescence detector, and becomes an "on-column flow cell." As the nucleic acid molecules migrate through the capillary as a result of the electric field, they pass through the detector light path and are measured by UV or fluorescence detection.

In preferred embodiments of the aspects described herein, a CE instrument for use with the methods of detecting nucleic acid molecules comprises a suitable sample injection module and a detector module, and can further comprise additional modules, such as temperature control modules, etc.

High-throughput CE apparatuses are available commercially, for example, the SCE 9610 fully automated 96-capillary electrophoresis genetic analysis system from P/ACE 5000 series and CEQ series from Beckman Instruments Inc (Fullerton, Calif.); and ABI PRISM 3100, 3130 and 3730 genetic analyzers (Applied Biosystems, Foster City, Calif.), among others. In some embodiments, the high-throughput CE apparatus and related quantitative methods used with the methods described herein are based on the methods and apparatuses described in "Scalable Transcriptional Analysis Routine Multiplexed Q_PCR Platform for Gene Expression Analysis and Molecular Diagnostics." J Mol Diag 7 44 (2005), and/or as described in U.S. Pat. Nos. 7,550,266; 7,445,893; 7,674,582; 7,081,339; 7,368,246; and in US 20040014117, the contents of each of which are herein incorporated in their entireties by reference. Near the end of the CE column, in these devices the nucleic acid fragments pass a fluorescence detector which measures signals of fluorescent labels. Accordingly, these apparatuses provide automated high-throughput for the detection of surrogate markers or surrogate marker amplicons of different sizes, as described herein.

Multiplex

The methods described herein are particularly adapted to provide analysis of two or more species (i.e., a plurality, e.g., 2, 3, 4, 5, 6, 7, 9, 9, 10, 15, 20, 25, 30, 40, 50, 75, 100, 250, 1000, or more) of target nucleic acids from a single sample by choosing or assigning different predetermined lengths for one or more of the splint molecules, prosthetic molecules, reverse transcription primers, PCR amplification primer pairs, surrogate markers, amplified extended splints, amplified extended prosthetic molecules, amplicons, or any combination thereof generated for each of a plurality of target nucleic acid sequences of interest, such that each surrogate marker, extended splint, extended prosthetic molecule, amplified extended splint, amplified extended prosthetic molecule, or amplicon thereof generated from each starting nucleic acid sequence of interest has a unique size. Thus, the two or more surrogate markers, amplified extended splints, amplified extended prosthetic molecules, or surrogate marker amplicons can be detected and quantified in a single analysis when the markers or amplicons are size-separated and detected, e.g., by means of a label incorporated into such markers or amplicons.

In preferred aspects, the relative sizes of the surrogate markers, i.e., extended splints, extended prosthetic molecules, and/or surrogate marker amplicons thereof, i.e., extended splint amplicons, extended prosthetic molecule amplicons, are distinguishable by electrophoresis or capillary electrophoresis. In preferred embodiments, the amount of each surrogate marker, i.e., extended splint, extended prosthetic molecule, and/or surrogate marker amplicon thereof, i.e., extended splint amplicon, extended prosthetic molecule amplicon, is measured in real time while the PCR amplification is still in progress, for example by withdrawing aliquots from the amplification reaction between PCR cycles and subjecting them to CE analysis while the next cycle or cycles are in progress, and repeating this sampling and analysis procedure at multiple points during the PCR amplification, as described in U.S. Pat. No. 7,445,893. By determining the "threshold cycle" or "$C_t$" at which the signal corresponding to a particular surrogate marker, i.e., extended splint, extended prosthetic molecule, and/or surrogate marker amplicon thereof, i.e., extended splint amplicon, extended prosthetic molecule amplicon, reaches or passes a predetermined threshold, and comparing this with the $C_t$ values recorded for known nucleic acid sequences present at known concentrations, either in control samples processed in parallel with the test sample, or in the test sample itself following the addition of such known nucleic acid sequences prior to the initiation of the test procedure, the concentration of each surrogate marker, i.e., extended splint, extended prosthetic molecule, and/or surrogate marker amplicon thereof, i.e., extended splint amplicon, extended prosthetic molecule amplicon, can be reliably estimated. Accordingly, in some embodiments of the aspects described herein, in order to avoid (relatively) lengthy separation times that would make it harder to perform CE contemporaneously with amplification, the largest surrogate marker, surrogate marker, i.e., extended splint, extended prosthetic molecule, and/or surrogate marker amplicon thereof, i.e., extended splint amplicon, extended prosthetic molecule amplicon, generated in any given reaction is preferably no more than 250 base-pairs in length.

Kits

Also provided herein are kits for the detection of target nucleic acids using the methods described herein. A kit, as described herein, provides at least one expander oligonucleotide, e.g., at least one prosthetic oligonucleotide, at least one splint oligonucleotide, or any combination thereof. A kit can include any assemblage of components that are necessary or facilitate any method described herein. The components of the kits are not particularly limited or restricted. Kits can also include other primers necessary for any of the methods described herein, for example, one or more reverse-transcription primers, amplification primer pairs, or combinations thereof. Kits for use with the methods described herein can optionally contain written instructions describing how to use the kit and/or conduct the methods provided herein. Kits can also provide enzymes necessary for the methods described herein, e.g., reverse trancriptase, and/or DNA polymerases. In some embodiments, the DNA polymerases can be thermostable polymerases.

Accordingly, in one aspect, provided herein are kits comprising at least one expander oligonucleotide specific for a target nucleic acid sequence. The expander oligonucleotide is preferably a DNA polynucleotide, preferably single-stranded, of predefined and specific sequence length, and comprises a replica sequence substantially identical to the mirrored portion of a specific target nucleic acid. The replica sequence of the expander oligonucleotide can hybridize to a complementary nucleic acid molecule, such as a complementary DNA molecule, that comprises a sequence complementary to the mirrored portion of a specific target RNA or DNA molecule. Polymerase extension of the 3'-end of the expander oligonucleotide, or the 3'-end of both the expander oligonucleotide and the complementary DNA sequence, forms an extension product of specific length, and, in some embodiments, discrete length that provides for a surrogate marker indicative of the presence of the target RNA or DNA sequence in a sample. The extended expander oligonucleotide can be amplified with appropriate primers to generate a surrogate marker of selected length indicative of the presence of the target RNA or DNA sequence in a sample. In some embodiments, the kit further comprises amplification primer pairs for subsequent amplification steps.

In some embodiments of these aspects, a kit comprises at least one prosthetic molecule, which is preferably a DNA polynucleotide, preferably single-stranded, of predefined and specific sequence length comprising, in the 5' to 3' direction: (i) a spacer sequence of defined length, and (ii) a replica sequence substantially identical to the mirrored portion of a specific target nucleic acid. In some embodiments, the prosthetic molecule further comprises a forward primer sequence at its 5'-end, such that the prosthetic molecule comprises, in the 5' to 3' direction, (i) a forward primer sequence, (ii) a spacer sequence, and (iii) a replica sequence. The spacer sequence in a prosthetic molecule can be of any sequence, and is preferably designed to minimize the potential of the spacer sequence to anneal with any other nucleic acids present in the same reactions as the prosthetic molecule, for example, by including a multiplicity of A and T nucleotides that will reduce the $T_m$ of any duplexes involving the spacer sequence.

In some embodiments, where the kit is used to detect at least one target RNA sequence, the mirrored portion of the prosthetic molecule is closer than the RT primer site to the 5'-end of the target RNA. The 3'-end of the prosthetic molecule can be located immediately adjacent, on the 5'-side, to the RT primer site within the target RNA sequence, or can even overlap such site. Alternatively, in other embodiments, there can be a gap between the 3'-end of the prosthetic molecule and the RT primer site within the target RNA sequence.

In some embodiments of these aspects, a kit comprises at least one splint molecule, which is a DNA polynucleotide, preferably single-stranded, of predefined and specific sequence length, the greater part or all of which sequence comprises a replica sequence substantially identical to the mirrored portion of a specific target nucleic acid, such that the splint molecule can serve as a template for extension of nucleic acid sequences complementary to the target nucleic acid.

In some embodiments, where the kit is used to detect at least one target RNA sequence, the mirrored portion of the splint molecule is 5' of the RT primer site within the target RNA sequence. The replica sequence of the splint molecule extends to and comprises the 3'-end of the splint molecule, and can preferably comprise at least 25 nucleotides, at least 30 nucleotides, at least 35 nucleotides, at least 50 nucleotides, at least 75 nucleotides, at least 100 nucleotides, at least 150, or at least 175 nucleotides.

In those embodiments relating to target RNA sequences, the 3'-end of the splint molecule can be located immediately adjacent, on the 5'-side, to the RT primer site within the target RNA, or can even overlap such site. Alternatively, there can be a gap between the 3'-end of the splint molecule and the RT primer site within the target RNA sequence. In some embodiments, an amplification primer for any subsequent amplification steps comprises a sequence within the 5' end of the splint molecule.

Examples

Methods to detect and quantify multiple different target nucleic acids in samples comprising different types of nucleic acids, e.g., DNAs and RNAs, multiple classes of RNA, and/or degraded nucleic acid molecules are currently lacking. In general, for example, the preferred method for quantifying RNA target sequences or species extracted from formalin-fixed paraffin-embedded (FFPE) tissue samples is reverse-transcriptase real-time quantitative PCR (RT-qPCR). This approach, employed by assays such as OncotypeDX (Genomic Health, Inc.), allows analysis of degraded RNA recovered from FFPE samples, which typically comprise RNA fragments of 100 nucleotides or less. However, most real-time qPCR methods, including RT-qPCR, are extremely difficult to multiplex because they generally solely rely on fluorescence to detect amplification; in such multiplex formats, each amplicon is detected by virtue of its association with a specific fluorophore, but the overlap in emission spectra of different fluorophores makes it difficult to quantify more than a few fluorophores simultaneously in a single reaction. As a result, detection and quantification of multiple targets is cumbersome and has to be performed in numerous singleplex reactions.

One approach to circumvent these difficulties is to generate and differentiate products or amplicons on the basis of size, rather than using only fluorogenic probes. Amplification primers can be selected such that each amplicon has a unique size, and the amplicons are separated from one another by capillary electrophoresis (CE) and quantified. This approach allows a high level of PCR multiplexing (e.g., 40 targets) in a single reaction. An exemplary platform for such size-based differentiation for use with the methods described herein is the STAR (Scalable Target Amplication Routine) technology (PrimeraDx, Inc.).

However, to ensure adequate separation between adjacent amplicons during electrophoresis, each amplicon should preferably be at least five base-pairs larger or smaller than the amplicons closest to it in size. Further, to ensure adequate separation of amplicons from unincorporated primers, primer-dimers, and other by-products of the amplification reaction, the smallest amplicon in any set should preferably be at least 100 base-pairs in length. Finally, to optimize separation time, the largest surrogate marker amplicon in any set should preferably be no more than 250 base-pairs in length.

The combined impact of these conditions has posed particular challenges for the application of CE-based methods to multiplex analysis of RNA extracted from FFPE samples, which, as described herein, is typically 100 nucleotides in length. These challenges can be illustrated by reference to the OncotypeDx assay, which requires amplification and quantification of 21 different transcripts. If amplicons for this assay were designed according to the requirements for electrophoresis, the smallest would be 100 base-pairs and the other twenty could range in size from 105 to 200 base-pairs; all but the smallest would therefore need to be longer than the average length of the RNAs from which they are derived—the larger amplicons considerably so.

Accordingly, in order to apply CE-based methods to FFPE samples, and other samples comprising, for example, multiple classes of short RNA targets, such as microRNAs and degraded mRNAs, or, for example, multiple types of nucleic acid target sequences, e.g., DNA and RNA targets, the methods described herein have been developed to generate amplicons that are significantly longer than their target nucleic acid molecules. Traditionally, this has been achieved for RNA molecules simply by using extra-long primers for reverse transcription and for subsequent amplification of the cDNA that is produced. A 100-nucleotide RNA can be converted, for example, into a 180 base-pair amplicon by including 40 extra nucleotides at the 5'-ends of the primers used for reverse transcription and PCR. In practice, however, this quickly becomes a highly complex undertaking, because the presence of multiple pairs of lengthy primers increases the probability of artifactual PCR products being formed, and primer designs that help to reduce such artifacts only add to the length of the primers.

Accordingly, provided herein are novel methods that represent alternative approaches that use "expander oligonucleotides," also known as splint molecules or prosthetic molecules, to generate surrogate markers, i.e., extended splint molecules or extended prosthetic molecules, or surrogate marker amplicons thereof, i.e., amplified extended splints or amplified extended prosthetic molecules larger than the target nucleic acids that are being detected. These methods take advantage, in part, of advances in DNA synthesis technology that make it possible to synthesize oligonucleotides or polynucleotides up to 200 nucleotides in length at reasonable cost.

An advantage of the methods described herein is that excess expander oligonucleotides—used at moderately high concentrations in the initial stages to drive, for example, conversion of cDNAs into amplifiable double-stranded (ds)DNA—can, if necessary, be removed enzymatically from the reaction prior to the amplification stages, significantly reducing the potential for formation of artifactual PCR products.

The key steps in the methods related to those embodiments pertaining to splint molecules are summarized in FIG. 3. For simplicity, and strictly by way of example, this example focuses on the production of two different amplicons corresponding to a 120-nucleotide segment of one mRNA target sequence ("RNA 1") and a 150-nucleotide segment of a second mRNA target sequence ("RNA 2"), in both cases from a sample comprising fragmented RNAs with an average length of 100 nucleotides extracted from FFPE samples [Step 1 in FIG. 3]. Many variations are possible on the specific embodiments of the method shown in this illustration; some such non-limiting variations are discussed below.

The embodiment of the method described in FIG. 3 depends on the use of a "splint molecule" for each target nucleic acid, comprising a replica sequence substantially identical to a segment of that target nucleic acid sequence (i.e., the "mirrored portion" of such target nucleic acid). In those embodiments in which at least one target nucleic acid sequence is an RNA sequence, a first-strand cDNA molecule, derived from reverse transcription of RNA molecules using a target-specific primer [Step 2], is annealed to the splint molecule [Step 3], which is designed to be substantially identical to a sequence just 3' proximal of the RT primer site on the target RNA, thus forming a partially double-stranded structure that is then extended or "repaired" (converted to fully dsDNA) using Taq DNA polymerase [2nd strand synthesis, Step 4]. Irrespective of the length of the RNA fragment that was first reverse-transcribed, the dsDNA or surrogate marker, i.e., extended splint molecule, in this embodiment, has a length equal to the length of the splint plus the length of the reverse transcriptase (RT) primer (plus, in an embodiment as described below, the length of any gap between the RT primer site on the target RNA sequence and the 3' end of the splint molecule). In some embodiments, treatment with a single-stand-specific nuclease can be performed [Step 5], such as an Exonuclease I, to remove excess splint molecules, and excess RT primers, leaving only dsDNA surrogate markers or double-stranded extended splint molecules ready for any further amplification steps [Step 6]. This nuclease treatment can significantly reduce the generation of amplification artifacts during PCR.

Variations on such embodiments include, but are not limited to:
  STEP 2: Use of random hexamers for priming of the initial cDNA synthesis step, instead of a gene-specific RT primer. These can be used to drive efficient copying of the entire RNA population into first-strand cDNAs. Excess hexamers can then be removed prior to Step 3(b) and 4 (addition of splint molecules and extension of partially dsDNA surrogate markers). This can be accomplished by treatment with a thermolabile single-strand-specific nuclease at Step 3(a) (in place of, or in addition to, treatment with RNases).
  STEP 2: RT primers can be selected that anneal somewhat downstream (i.e., 3') of the mirrored portion of the target RNA (i.e., closer to the 3'-end of the target RNA sequence), such that there is a gap between the splint molecule and the RT primer site that is "bridged" by cDNA sequence added to the RT primer during first-strand synthesis by reverse transcription. This allows the use of shorter splint molecules. For example, RNA 2 in FIG. 3 can be reverse-transcribed using a primer that anneals 40 nucleotides downstream of the mirrored portion of the RNA sequence, allowing the use of a 110-nucleotide splint molecule to produce the same amplicon that would require a 150-nucleotide splint molecule in those embodiments where the RT primer annealed immediately adjacent to the mirrored portion of RNA 2. Moving the RT priming site downstream does, however, reduce the length of the region within the first-strand cDNA that will be complementary to the splint molecule and, to some extent, the percentage of the RNA fragments in FPPE-derived samples that can yield cDNAs capable of annealing to the splint molecule. However, with fragmented RNAs of an average size of 100 nucleotides, an RT primer that anneals with its 3' end (i) 20 nucleotides in from the 3' end of an RNA fragment, and (ii) 50 nucleotides downstream of the mirrored portion of the target RNA, still yields a first-strand cDNA with 30 nucleotides of complementarity to the splint molecule, which is more than sufficient for the cDNA and splint molecule to anneal prior to "repair" with Taq DNA polymerase in Step 4.
STEP 3: In some embodiments, the addition of RNase H (with or without another RNase) can be omitted at this step, as many reverse transcriptases include an intrinsic RNase H activity; RNA can be hydrolyzed when the temperature is elevated to denature all nucleic acids prior to addition of the DNA splint molecules; and the latter are added in large excess, to drive annealing to the target first-strand cDNAs.
STEP 4: Any DNA polymerase can be utilized for this step, although in some embodiments the same enzyme that is employed for subsequent PCR amplification can be utilized.
STEP 5: In some embodiments, addition of a single-strand-specific nuclease can be omitted at this step. The single-stranded nucleic acids present in a reaction comprise unused RT primers and splint molecules (both of which would have been added in large excess at earlier stages), together with any RNA that has survived to this stage. In some embodiments, if carried over into STEP 6, the RT primers can be used as reverse primers for the PCR. In other embodiments, excess RT primers and splint molecules can be removed to allow the PCR to begin with a "clean" population of dsDNA surrogate markers derived from the target RNAs, which can simplify primer design and reduce the potential for spurious amplification products to be formed.
STEP 6: Various designs of PCR primer pairs can be adopted in different embodiments to allow, for example, the addition of further length to the double-stranded surrogate markers resulting from Step 4. If, for example, the double-stranded surrogate marker corresponding to a particular RNA is amplified with 40-nucleotide-long forward and reverse primers, each comprising a 20-nucleotide "tag" sequence at the 5' end and a 20-nucleotide sequence specific for the double-stranded surrogate marker at the 3' end, the resulting amplicon is 40 nucleotides longer than the double-stranded surrogate marker. Again using RNA 2 from FIG. 3 as an example, in another embodiment, if (i) the initial RT primer is 20 nucleotides long; (ii) there is a 40-nucleotide gap between the RT primer and the mirrored portion of the RNA; and (iii) the forward and reverse primers used in Step 6 add a further 40 nucleotides to the amplicon, then the splint molecule only needs to be 70 nucleotides long to produce an amplicon 170 base-pairs in length, as illustrated in FIG. 4. In other embodiments, if each of the forward primers used for the initial round of amplification comprises a common 5' tag upstream of the target-specific priming sequence, and the reverse primers comprises a similar design but with a different common 5' tag sequence, then subsequent rounds of amplification can be accomplished using universal forward and reverse primers complementary to the common 5' tags present in the initial primer sets.

Figure 6:
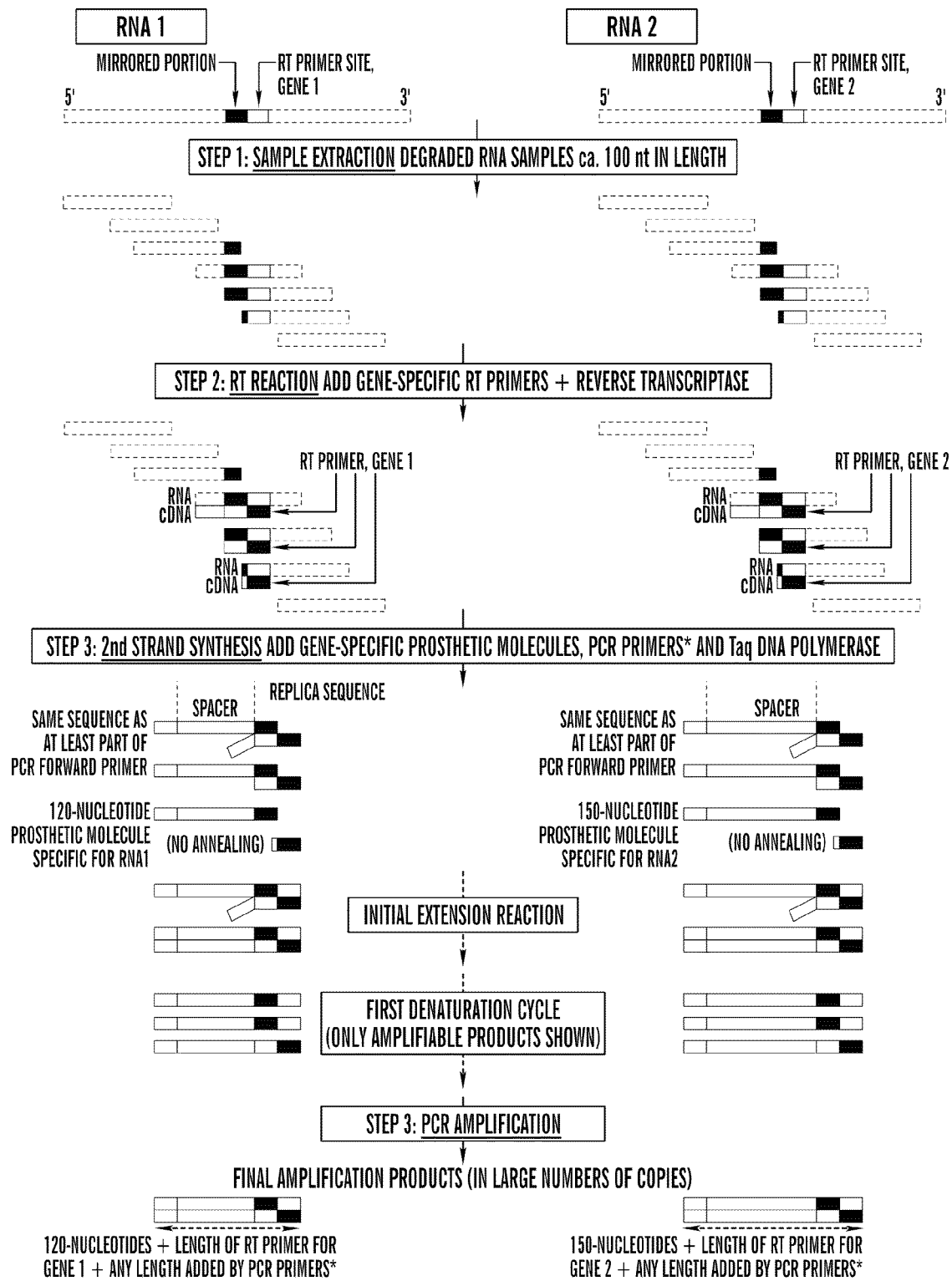
FIG. 6 provides a schematic for a method for generating extended template oligonucleotide amplicons of different, predetermined lengths from FFPE-extracted RNA according to one aspect of the methods described herein. In this schematic diagram, different expander/prosthetic oligonucleotides of defined and different lengths and specific for two different target RNA sequences are extended, upon hybridization to a complementary cDNA molecule, and amplified into multiple copies having specific, predefined lengths, such that each extended prosthetic molecule is indicative of the presence of a specific RNA target sequence in the sample. RNAs are shown using dotted lines for their outlines, with the solid line sections within each one indicating the mirrored portion of the target sequence and the RT primer site.
Figure 7:
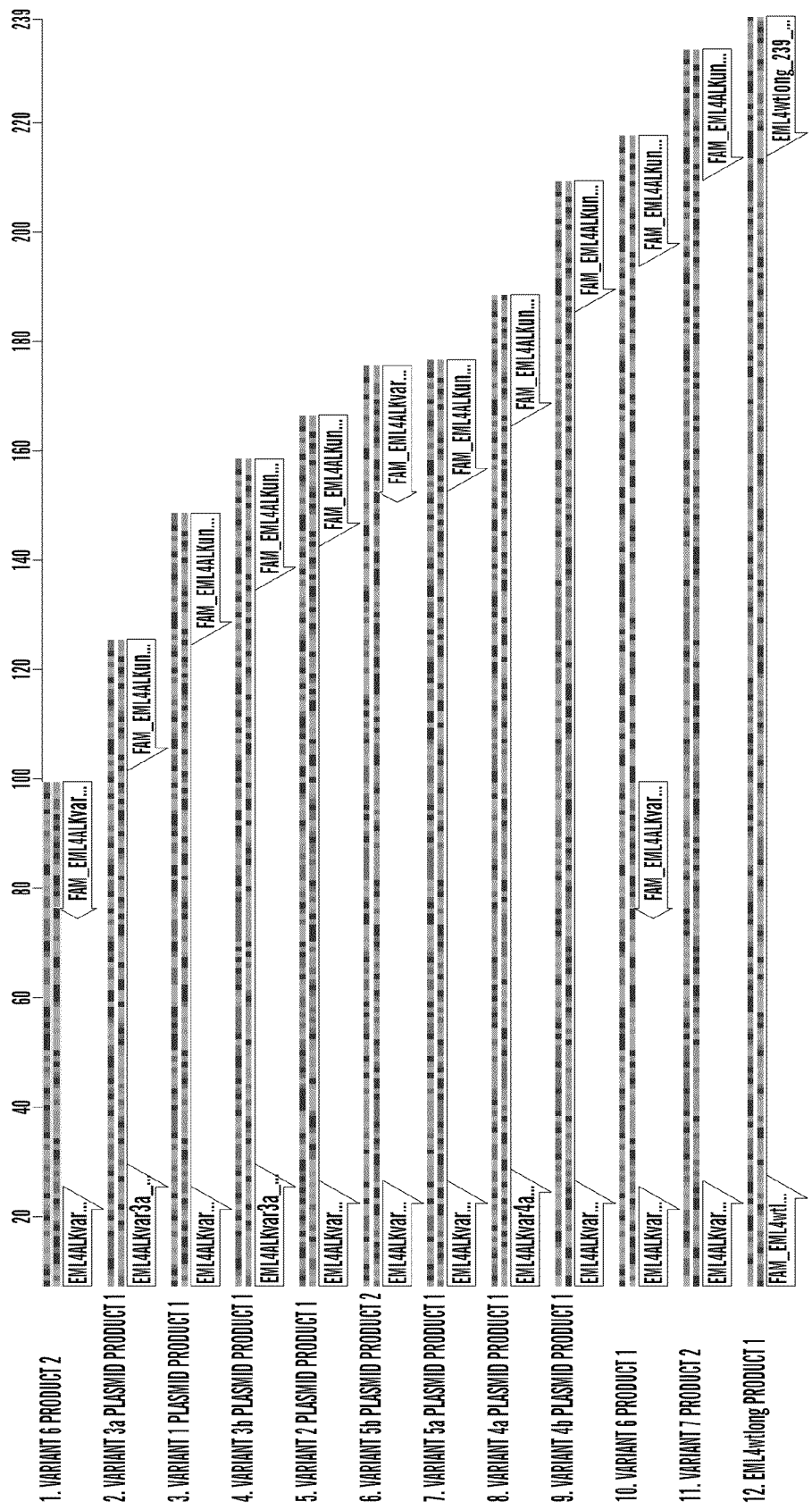
FIGS. 7-10 provide design and demonstrate function of a multiplex RT-PCR EML4 ALK detection assay using an embodiment of the expander approach described herein. The EML4 ALK oncogene is the result of a fusion between the EML4 (echinoderm microtubule-associated protein-like 4) gene and the ALK (anaplastic lymphoma kinase) gene that yields a kinase that is highly active and associated with non-small cell lung cancers. Not all non-small cell lung cancers express the EML4 ALK oncogene fusion, but those that do can be targeted with inhibitors of the EML4-ALK tyrosine kinase for treatment. Thus, an assay that detects the fusion can provide valuable information to guide therapy. The fusion is known to occur at a number of different fusion breakpoints, and an assay that can detect a number of them, and preferably substantially all of them in a single reaction is advantageous. Sequences for expander templates and primers sufficient to detect fusion variants 1, 2, 3a, 3b, 4a, 4b, 5a, 5b and 6 as well as wild-type EML4 and ALK are provided in Table 1. In Figures showing assay results, each lane represents a different cycle of the reaction.
Figure 8:
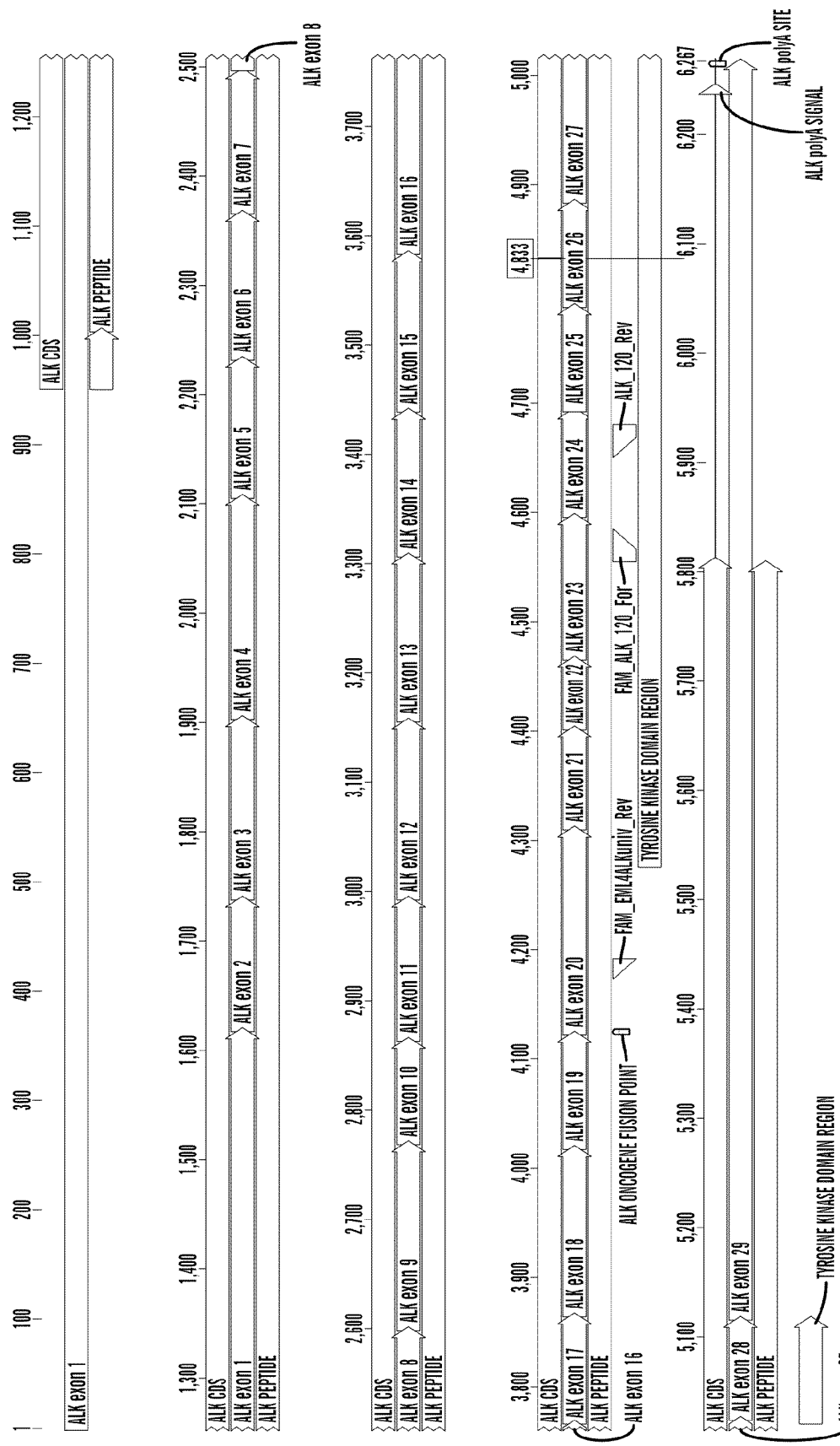
Figure 9:
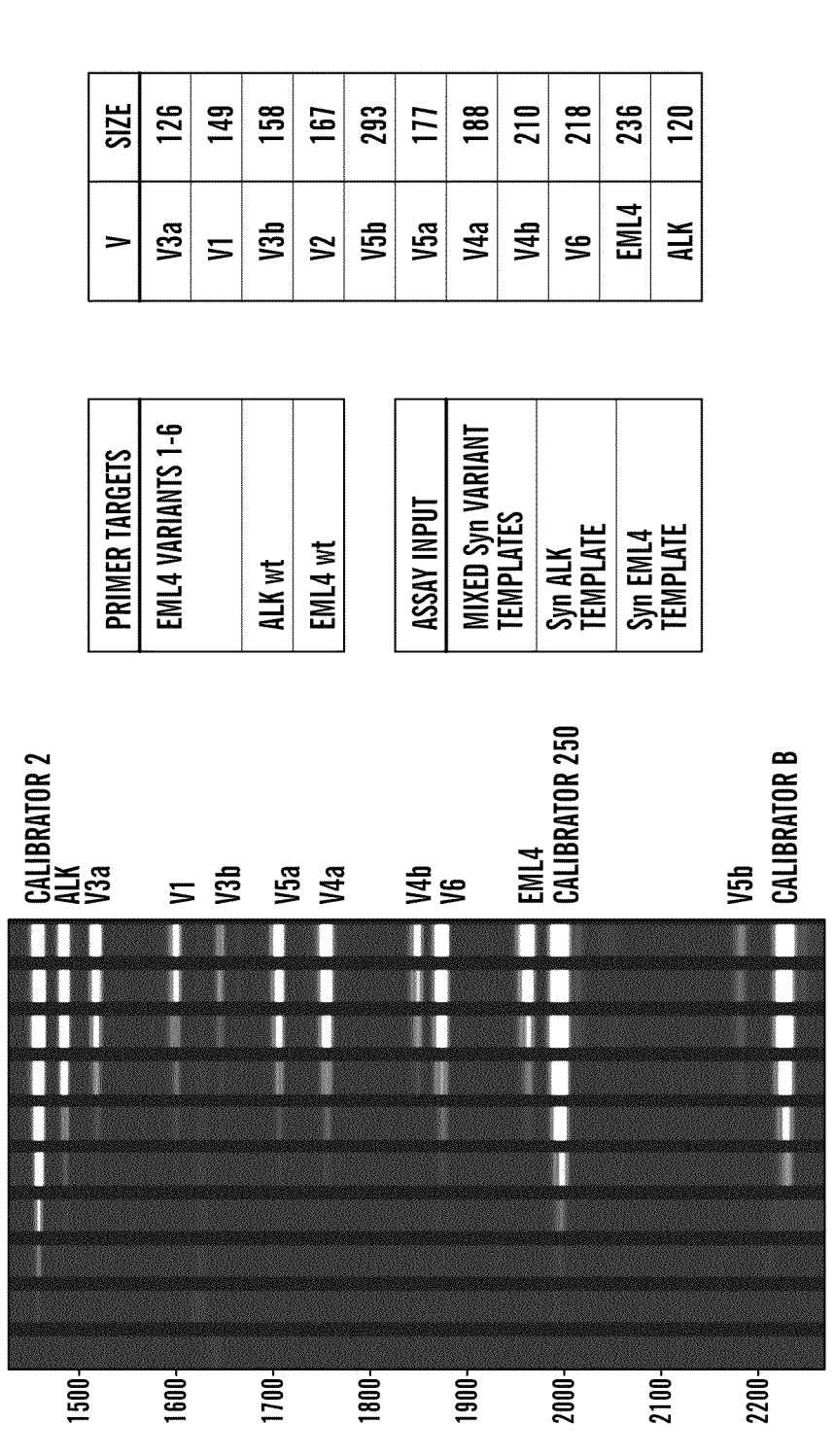
Figure 10:
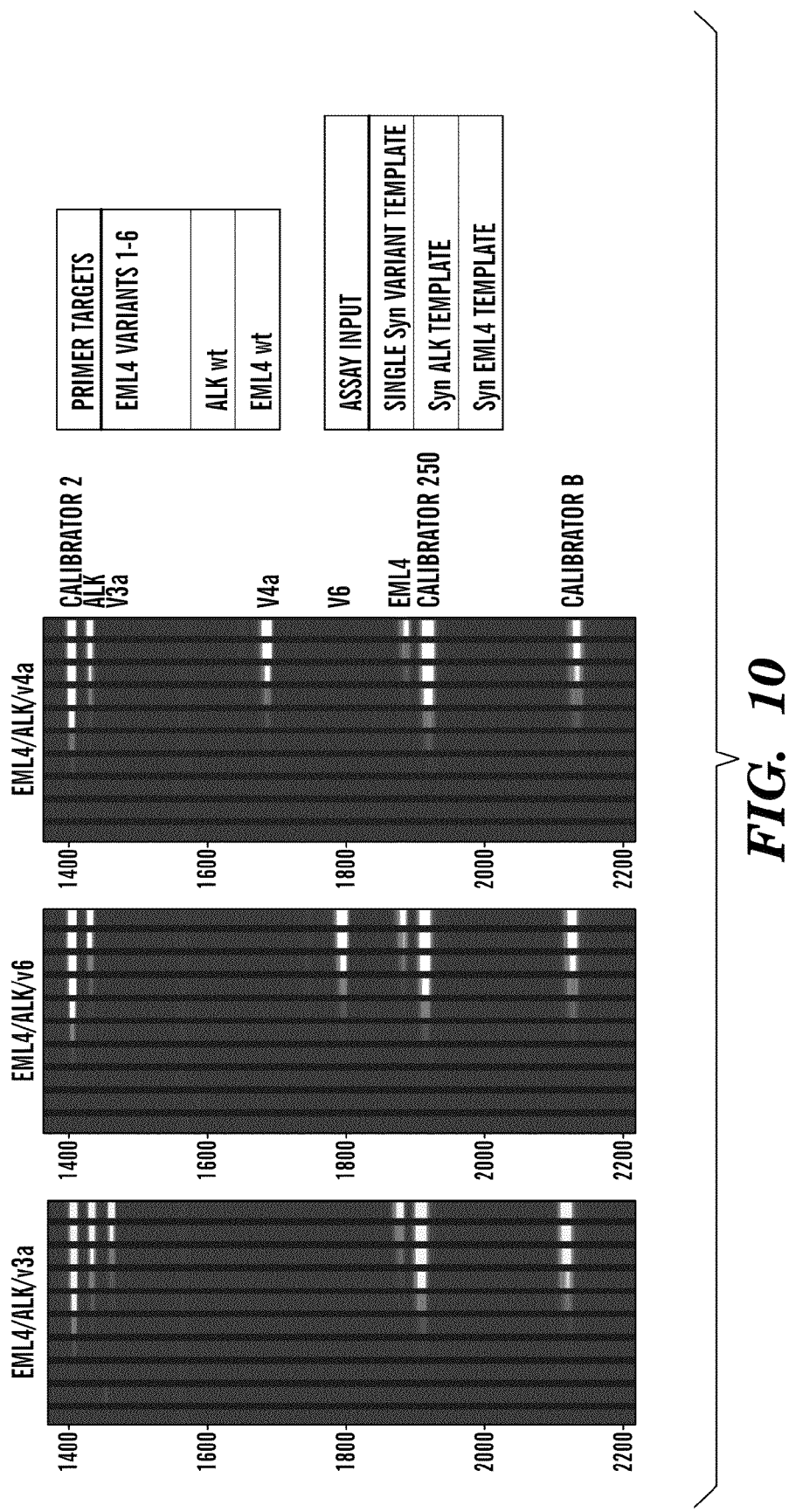
Figure 11:
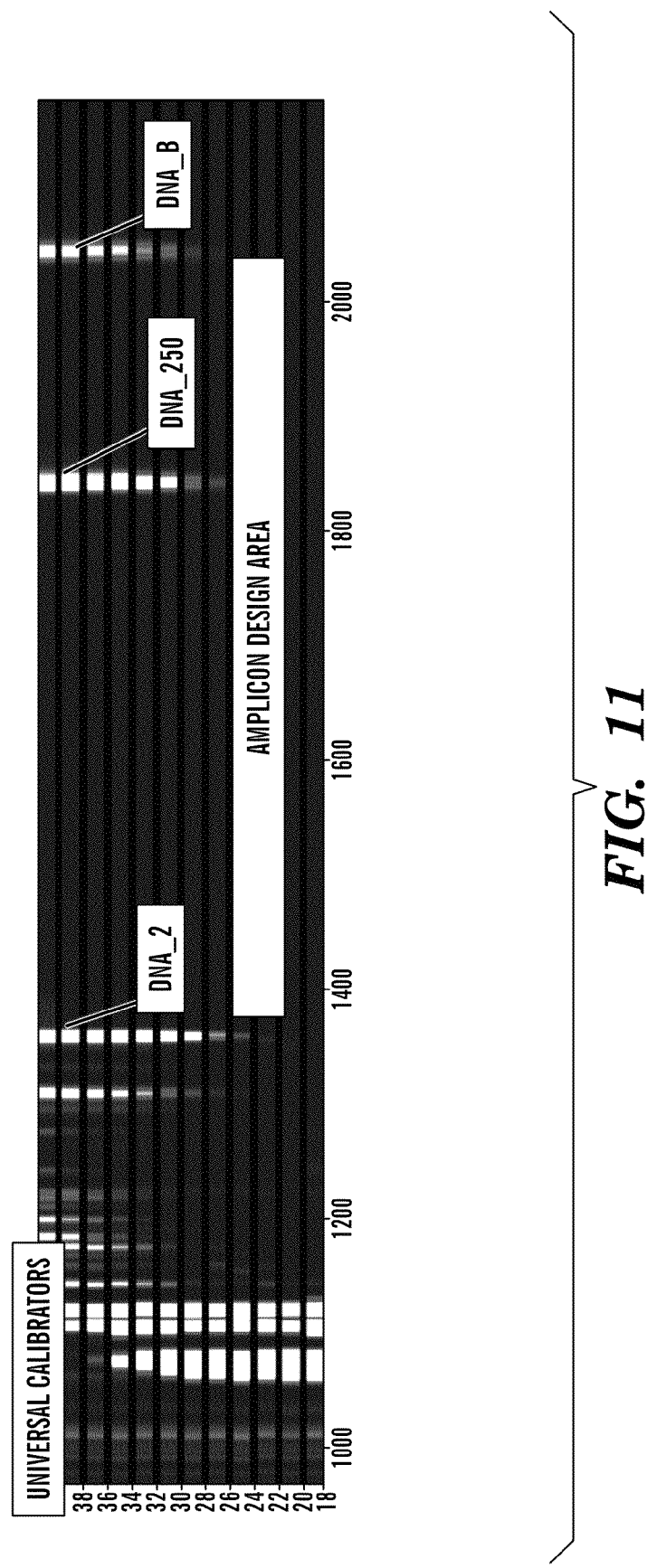
FIG. 11 shows an example of the amplicon size space available for multiplex PCR assays as described herein. The area flanked by calibrators DNA_2 (111 nt) and DNA_B (305 nt) permits space for more than 35 individual targets per dye label channel (FAM or TYE) where the amplicon sizes are designed to be 5-10 nt apart.
Figure 12:
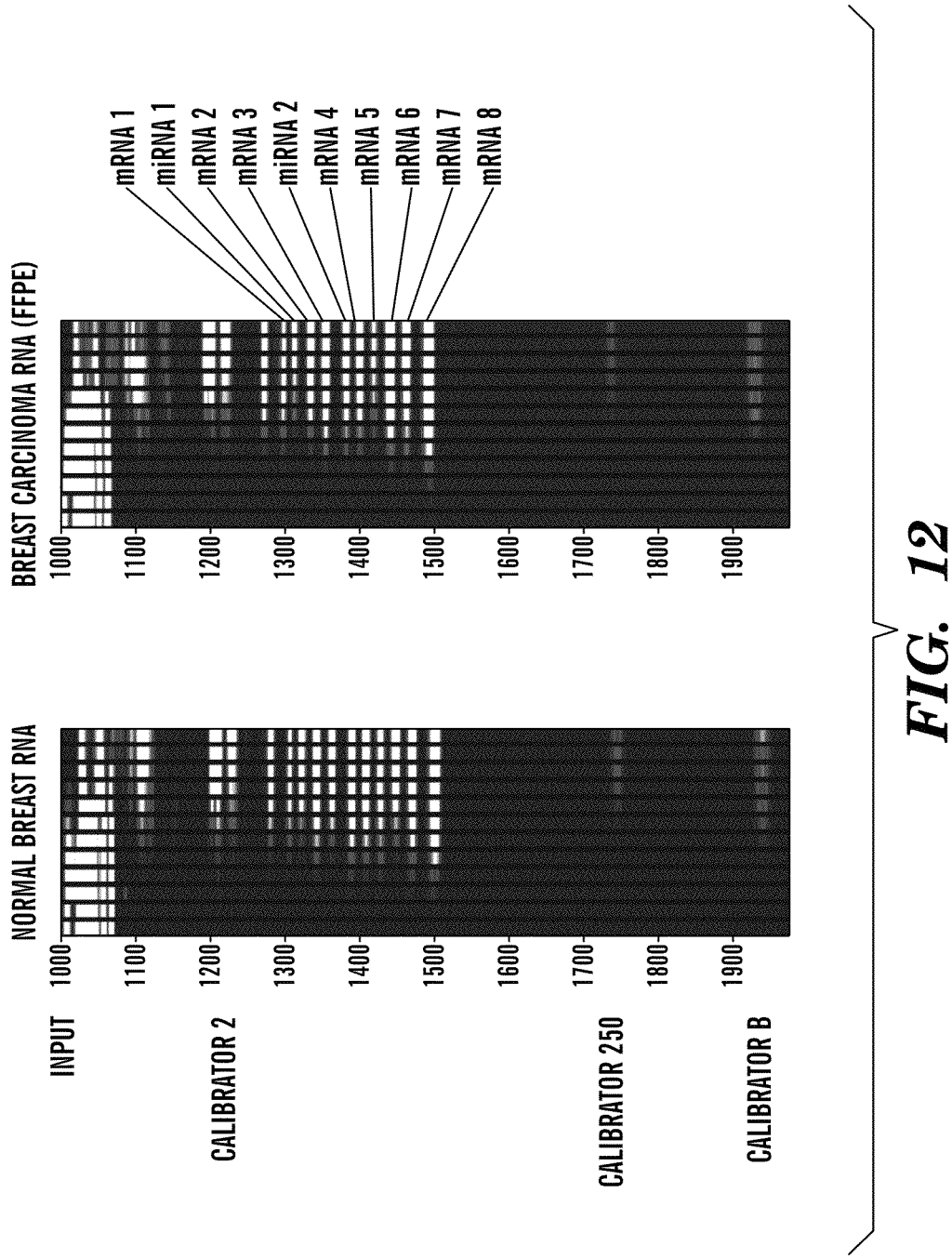
FIG. 12 shows an example of a multiplex, multimodal PCR assay for the detection of a panel of different miRNA and mRNA targets in the same reaction using the expander technology described herein. Normal breast RNA (left panel) is compared with RNA isolated from an FFPE breast carcinoma sample. Eight different mRNAs and two different miRNAs are detected with similar signals in each sample, thereby demonstrating the power of the expander technology for multimodal detection of target RNAs in degraded RNA samples. The sampling of the PCR reaction at multiple cycles can permit quantitation of initial target template amounts.
Figure 13:
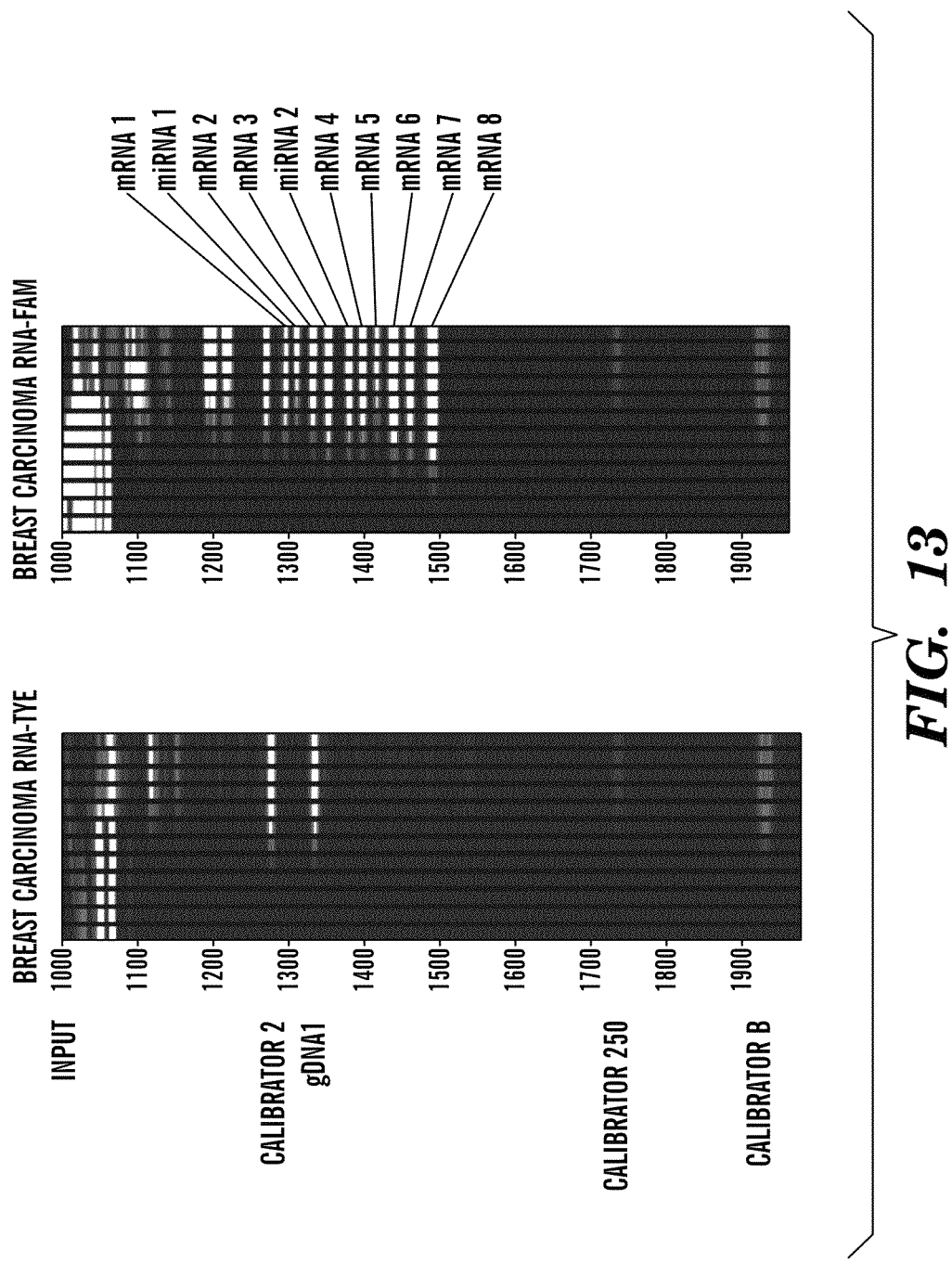
FIG. 13 shows an example of a multiplex, multimodal PCR assay for the detection of a panel of different miRNA and mRNA targets and a DNA target in the same reaction using the expander technology described herein. Input RNA was isolated from an FFPE breast carcinoma sample. Eight different mRNAs, two different miRNAs and a genomic DNA target are detected using two different fluorescent dye markers/channels, FAM and TYE. The sampling of the PCR reaction at multiple cycles can permit quantitation of initial target template amounts.

The key steps of various embodiments of the methods related to prosthetic molecules are summarized in FIG. 1 and FIG. 6. For simplicity, and strictly by way of example, FIG. 6 focuses on the production of two different amplicons corresponding to a 120-nucleotide segment of one target RNA ("RNA 1") and a 150-nucleotide segment of a second target RNA ("RNA 2"), in both cases from a sample comprising fragmented RNAs with an average length of 100 nucleotides extracted from, for example, FFPE samples [Step 1 in FIG. 6]. Many variations are possible on the specific embodiments of the method shown in this illustration; some such variations are discussed herein.

The embodiment of the methods described, for example, in FIG. 6 depends on the use of a single-stranded DNA "prosthetic molecule" specific for each target RNA, comprising at its 3' end a replica sequence substantially identical to the mirrored portion of that target RNA sequence. Each prosthetic molecule, in the embodiment shown herein, comprises, in the 5' to 3' direction, a forward primer binding sequence, a spacer sequence of defined length, and a target-specific replica sequence.

First-strand cDNA, derived from reverse transcription of the target RNA sequence using a target-specific primer [Step 2], is annealed to the prosthetic molecule, [Step 3] which is designed such that its replica sequence is substantially identical to a mirrored portion of the RNA sequence just 3' proximate to the RT primer site, forming a partially double-stranded structure that is then extended using a template-specific polymerase, such as Taq DNA polymerase, generating an extended prosthesis [2nd strand synthesis, Step 3]. Irrespective of the length of the RNA fragment that was first reverse-transcribed, the extended prosthesis has a length equal to the length of the prosthetic molecule plus the length of the reverse transcriptase (RT) primer. Thus, the extended prosthetic molecule produced for each target RNA sequence does not have a different and discrete length, in the embodiment shown. As described elsewhere herein, in some embodiments relating to prosthetic molecules, the extended prosthetic molecule produced for each target nucleic acid sequence is not a different and discrete length, and instead obtains a length unique for its target nucleic acid sequence only upon subsequent amplification steps.

As in embodiments featuring splint molecules, the RT primers used in step 2 of a procedure involving prosthetic molecules can be selected to anneal somewhat downstream of the mirrored portion of the target mRNA (i.e., closer to the 3'-end of the RNA), such that there is a gap between the replica sequence of the prosthetic molecule and the RT primer site that is "bridged" by cDNA sequence added to the RT primer during first-strand synthesis by reverse transcription. This allows the use of shorter prosthetic molecules. For example, RNA 2 in FIG. 6 can be reverse-transcribed using a primer that anneals 40 nucleotides downstream of the mirrored portion of the target RNA sequence, allowing the use of a 110-nucleotide prosthetic molecule to produce the same extended prosthesis that would require a 150-nucleotide prosthetic molecule in those embodiments where the RT primer annealed immediately adjacent to the mirrored portion of RNA 2. Moving the RT priming site downstream does, however, reduce the percentage of the RNA fragments in FPPE-derived samples that can yield cDNAs capable of annealing to the prosthetic molecule. However, with fragmented RNAs of an average size of 100 nucleotides, an RT primer that anneals with its 3' end (i) 20 nucleotides in from the 3' end of an RNA fragment, and (ii) 50 nucleotides downstream of the mirrored portion of the target RNA sequence, still yields a first-strand cDNA that extends 30 nucleotides beyond the 3'-end of the replica sequence in the prosthetic molecule, and given that this replica sequence need not be even 20 nucleotides in length to ensure specific annealing of the cDNA and prosthetic molecule, should be more than sufficient to allow annealing and extension of the prosthetic molecule.

Various designs of PCR primer pairs for amplification steps can be adopted to allow, for example, the addition of further length to the extended prosthetic molecules resulting from Step 3. If, for example, the extended prosthetic corresponding to a particular RNA is amplified with 40-nucleotide-long forward and reverse primers, each comprising a 20-nucleotide "tag" sequence at the 5' end and a 20-nucleotide sequence corresponding to, respectively, a sequence present at the 5'-end of the prosthetic molecule and the RT primer sequence, the resulting extended prosthetic amplicon is 40 nucleotides longer than the original extended prosthesis.

5-Plex RT-PCR of Multiple Classes of RNA Targets from FFPE Extracted Material

Described herein are exemplary conditions used for performing an embodiment of the methods described herein to analyze five different target RNA sequences from FFPE extracted material in multiplex.

1. A 1 µl aliquot of a 1 µM solution of RT primer mix (GAPDH_PDx_RTs-2,5'-GGC AGA GAT GAT GAC C-3' (SEQ ID NO: 1), GUSB_PDx_RTs-2,5'-CCT TTT TAT TCC CCA GC-3" (SEQ ID NO: 2), RPLPO_PDx_RTs-2,5'-ACA AAG GCA GAT GGA TC-3" (SEQ ID NO: 3), TFRC_PDx_RTs-2,5'-ACT CAG GCC CAT TTC C-3" (SEQ ID NO: 4) and ACTB_PDx_RTs-2,5'-GAG TTG AAG GTA GTT TCG-3' (SEQ ID NO: 5)) was combined with 50 ng of RNA, extracted from FFPE material using the QuickExtract FFPE RNA extraction kit according to the manufacturer's (EPICENTRE) recommendations for total RNA extraction, in 20 µl reaction buffer: 50 mM Tris-HCl, 75 mM KCl, 3 mM MgCl$_2$, 5 mM dithiothreitol, 0.5 mM dNTPs (deoxyribonucleotide triphosphates), pH 8.3, containing 40 U of SuperScript III reverse transcriptase (Invitrogen) and incubated for 30 minutes at 42° C., followed by 5 minutes at 90° C.

2. A 5 µl aliquot of the RT reaction was combined with a 1 µl aliquot 1.25 µM solution of MIA primer mix (GAPDH_MTA_F1, 5'-AGT GGT TGG AGC TGT CTC AGT CTT CAT ATA AAT TTT TAT AAA TTT TAT TAT TTT TAA TAA ATA ATA TTT TTA AAT ATA AAA GTC CAC TGG CGT CTT CAC CAC CAT G-3' (SEQ ID NO: 6), GUSB_MTA_F1, 5'-AAG CGT GCA CTT ACC TAG TGT GCT GAT ATA CGT GGT TGG AGA GCT CAT TTG GAA TT-3' (SEQ ID NO: 7), RPLPO_MTA_F1,5'-AGC ACC TAT CGA GCC TAC TCT ACG CAT ATA AAT TTT TAT AAA TTT TAT TAT TTT TAA TAA ATA ATA TTT TTA AAT ACG GAT TAC ACC TTC CCA CTT GCT G-3' (SEQ ID NO: 8), TFRC_ MTA i1, 5'-AAG CGT GCA CTT ACC TAG TGT GCT GAT ATA AAT TTT TAT AAA TTT TAT TAT TTT TAA TCC AAC TGC TTT CAT TTG TGA GGG ATC TGA-3' (SEQ ID NO: 9) and ACTB_MTA_F1,5'-ACT GTT GGA ACT CCA CTG GTG AGA GAT ATA AAT TTT TAT AAA TTT TAT TAT TTT TAA TAA ATA ATA TTT TTA AAT ATA AAA ATT AAT ATT TAT ATA AAT TTA AAT TAT AAA AGA GGC ACT CTT CCA GCC TTC CTT CC-3) (SEQ ID NO: 10) and a 1 µl aliquot of a 5 µM PCR primer mix (GAPDH_Syn_F-1,5'-AGT GGT TGG AGC TGT CTC AGT CTT C-3' (SEQ ID NO: 11), GUSB_Syn_F-1,5'-AAG CGT GCA CTT ACC TAG TGT GCT G-3' (SEQ ID NO: 12), RPLPO_Syn_F-1,5'-AGC ACC TAT CGA GCC TAC TCT ACG C-3 (SEQ ID NO: 13), TFRC_Syn_F-1, AAG CGT GCA CTT ACC TAG TGT GCT G-3' (SEQ ID NO: 14), ACTB_Syn_F-1,5'-ACT GTT GGA ACT CCA CTG GTG AGA G-3 (SEQ ID NO: 15)', GAPDH_PDx_Rev-1 FAM, 5'-/56-FAM/AGG CAG AGA TGA TGA CCC TTT TGG CT-3' (SEQ ID NO: 16), GUSB_ PDx_Rev-1 FAM, 5'-/56-FAM/CCT TTT TAT TCC CCA GCA CTC TCG TCG-3' (SEQ ID NO: 17), RPLPO_PDx_Rev-1 FAM, 5'-/56-FAM/ACA AAG GCA GAT GGA TCA GCC AAG AAG-3' (SEQ ID NO: 18), TFRC_PDx_Rev-1 FAM, 5'-/56-FAM/ACT CAG GCC CAT TTC CTT TAT GTC TGC-3' (SEQ ID NO: 19), and ACTB_PDx_Rev-1 FAM, 5'-/56-FAM/AGA GTT GAA GGT AGT TTC GTG GAT GCC A-3' (SEQ ID NO: 20)); 12.5 µl of Multiplex PCR Master Mix (Qiagen) and 1.25 U of HotStar Taq DNA polymerase (Qiagen) to a final reaction volume of 25 µl in a single well of a 96-well microtiter plate.

3. The PCR reaction and subsequent CE separations were performed in an ICEPlex instrument according to the manufacturer's (PrimeraDx's) instructions with the cycling conditions defined as follows: After initial denaturation and enzyme activation for 15 minutes at 98° C., the reaction mix is incubated for 30 seconds at 57° C., followed by 60 seconds at 66° C., followed by 18 cycles of incubation for 20 seconds at 96° C. and 120 seconds at 66° C., followed by 24 cycles of incubation for 20 seconds at 96° C., followed by 90 seconds at 66° C. and 120 seconds at 72° C., with CE sampling occurring every other cycle.

Multiplex RT-PCR and qPCR of DNA and Multiple Classes of RNA Targets from FFPE Extracted Material Described herein are exemplary conditions used for performing an embodiment of the multi-modal analysis approach to analyze five target RNA sequences belonging to two different classes and a single target DNA sequence from FFPE extracted material in multiplex.

1. A 1 µl aliquot of a 1 µM solution of RT primer mix for three mRNA targets (CTSL2_RT2,5'-CAG TCG CAC TAA AAG C-3' (SEQ ID NO: 21), MMP11_RT2,5'-CCA GTA CCT GGC GAA G-3" (SEQ ID NO: 22), CD68_RT2,5'-GTT GGG GTT CAG TAC AG-3" (SEQ ID NO: 23) and two miRNA targets (Let7a_RT1,5'-CTA ACT AGA ACT TGT TAC TTA ACT ATA C-3" (SEQ ID NO: 24) and Let7b_RT2, 5'-CTA ACT AGA ACT TGT TAC TTA TTA TAA CCA CAC-3' (SEQ ID NO: 25) was combined with 50 ng of RNA, extracted from FFPE material using the QuickExtract FFPE RNA extraction kit according to the manufacturer's (EPI-CENTRE) for recommendations for total nucleic acid extraction, in 20 µl reaction buffer: 50 mM Tris-HCl, 75 mM KCl, 3 mM MgCl$_2$, 5 mM dithiothreitol, 0.5 mM dNTPs (deoxyribonucleotide triphosphates), pH 8.3, containing 20 U of SuperScript III reverse transcriptase (Invitrogen) and incubated for 30 minutes at 42° C., followed by 5 minutes at 90° C.

2. A 5 µl aliquot of the RT reaction was combined with a 1 µl aliquot of an expander oligo mix containing 1.25 µM of each oligo (CTSL2-MTA_F1,5'-ATA GAC GAG TCT CAA CAC AGA CGC GAT ATA AAT GTG GAT TGG AGA AAG AAA GGC TAC GTG-3' ((SEQ ID NO: 26)), MMP11_MTA_F2,5'-AGT GGT TGG AGC TGT CTC AGT CTT CAT ATA AAT TTT TAT AAA TTT TAT TAT TTT TAA TAA ATA ATA TTT TTA AAT ATA GCG ATG TGA CGC CAC TCA CCT TTA C-3' ((SEQ ID NO: 27)), CD68-MTA_F1,5'-TAC CAG TCT GTG TCG AAC AGC GAT CAT ATA AAT TTT TAT AAA TTT TAT TAT TTT TAA TAA ATA ATA TTT TTA AAT ATA AAA ATT AAT ATT TAT ATA AAT TTC CAC CTC CAA GCC CAG ATT CAG A-3' ((SEQ ID NO: 28)) for three mRNA targets, Let7ab_MTA_F1, 5'-ACT GTT GGA ACT CCA CTG GTG AGA GAT ATA AAT TTT TAT AAA TTT TAT TAT TTT TAA TAA ATA ATA TTT TTA AAT TGA GGT AGT AGG TTG-3' ((SEQ ID NO: 29)) for two miRNA targets, and TFRC_MTA_F2,5'-GCG CTC CTG AGT CTC TAA CTA CCA CAT AAA TCT GTG GAT TAG AGA CCT AGG ACA-3 ((SEQ ID NO: 30)) for a single DNA target), and a 1 µl aliquot of a PCR primer mix containing 5 µM of each forward (F) and reverse primer (R, labeled with fluorophore) (CTSL2_Syn_F1, 5'-ATA GAC GAG TCT CAA CAC AGA CGC G-3' ((SEQ ID NO: 31)), CTSL2_R1, 5'-/56-FAM/CAG TCG CAC TAA AAG CCC AAC AAG AAC-3' ((SEQ ID NO: 32)), MMP11_Syn_F1, 5'-AGT GGT TGG AGC TGT CTC AGT CTT C-3 ((SEQ ID NO: 33)), MMP11_R1,5'-/56-FAM/CCA GTA CCT GGC GAA GTC GAT CAT G-3' ((SEQ ID NO: 34)), CD68_Syn_F1, 5'-TAC CAG TCT GTG TCG AAC AGC GAT C-3 ((SEQ ID NO: 35))', CD68_R1,5'-/56-FAM/AGT TGG GGT TCA GTA CAG AGA TGC CC-3' ((SEQ ID NO: 36)), for three mRNA targets, Let7_Syn_F1,_5'-ACT GTT GGA ACT CCA CTG GTG AGA G-3' ((SEQ ID NO: 37)) and Let7_R1,5'-/56-FAM/ACA CAA CGG CGT CTA ACT AGA ACT TGT TAC TT-3' ((SEQ ID NO: 38)), for two miRNA samples, and TFRC_Syn_F1, 5'-/GCG CTC CTG AGT CTC TAA CTA CCA C-3' ((SEQ ID NO: 39)) and TFRC_R2,5'-/5TYE665/ATA AAA ATT ATG CCT GGG AGA CAT GAG TGA CGA AA-3' ((SEQ ID NO: 40)) for a single DNA target), with 1× FastStart Taq DNA polymerase (Roche) reaction mix (at 6 mM MgCl$_2$, 0.4 mM dNTP) to which 0.3 ul (1.5 U) of Fast-Start Taq DNA polymerase and 0.3 ul (1.5 U) of HotStar Taq DNA polymerase (Qiagen) was added to a final reaction volume of 25 µl in a single well of a 96-well microtiter plate.

3. The PCR reaction and subsequent CE separations were performed in an ICEPlex instrument according to the manufacturer's (PrimeraDx's) instructions with the cycling conditions defined as follows: After initial denaturation and enzyme activation for 10 minutes at 98° C., the reaction mix is incubated for 18 pre-CE cycles at 60° C. for 20 seconds, 72° C. for 20 seconds, and 98° C. for 5 seconds, followed by 24 PCR cycles with 90 seconds at 66° C., followed by 140 seconds at 72° C. and 10 seconds at 96° C. with CE sampling occurring every other cycle.

Sample Reactions

Table 1 describes primer/template sequences, including non-target-specific sequences as appropriate, for the EML4-ALK panel. Table 2 presents reverse transcriptase reaction mixtures appropriate for use with the primer/template sequences of Table 1, Table 3 presents PCR reaction mixtures appropriate for use with the primer/template sequences of Table 1, and Table 4 presents thermocycling conditions appropriate for use with the primer/template sequences of Table 1.

TABLE 1

EML4-ALK Panel.

| Primer | Sequence | SEQ ID NO: |
|---|---|---|
| Reverse Primers | | |
| EML4_ALK uni_Rev | TTG CTC AGC TTG TAC TCA GGG CTC | 41 |
| ALK/I19_uni_Rev | ATA AAA ATT AAG CAC TAC ACA GGC CAC TTC CT | 42 |
| ALK pan Rev | ATA AAA ATT ATG ATG TTG CCA GCA CTG AGT CAT TAT C | 43 |
| EML4 wt Rev | ATA AAA ATT AGA TCG CAC CAG TGC ATT GAT ATC TGT | 44 |
| Var 5b_Rev FAM | ATA AAA ATT AAT ATT TAA AGC CTC CCT GGA TCT CCA TAT CCT | 45 |
| Var 5b(+2)_Rev | ATA AAA TTA ATA TTT ATA TAA GCC TCC CTG GAT CTC CAT ATC CT | 46 |
| ALK Rev FAM | ATA AAA ATT AAT ATT TAT ACA AGT GGA CCA TAT TCT ATC GGC AA | 47 |
| MTA Primers | | |
| ALK Pan_MTA | CCA CCG CCT TCA AGT TTA ACG ACA CAT ATA AAT TTT TAT AAA TTT TAT TAT TTT TAA TAA ATA ATA TTT GGA AGT TCT GGA GTT TGT CAC | 48 |
| ALK wt_MTA | ACC TCG CTG GTA GAC CTC GTC TAA CAT ATA AAT TTT TAT AAA TTT TAT TAT TTT TAA TAA ATA ATA TTT TTA AAT AAT CTT TCT CCG GCA TCA TGA TTG T | 49 |
| EML4 wt_MTA | TTG CAC CGC ACC ACA TAC TAG TAC GAT ATA AAT TTT TAT AAA TTT TAT TAT TTT TAA TAA ATA ATA TTT TTA AGG ACA TTG ATT GGA CGA CAT ATA C | 50 |
| Var 1_MTA | AGC CTT GCG GTA CGG TTA GTG TTT CAT ATA AAT TTT TAT AAA TTT TAT TAT TTT TAA TAA ATA ATA ACA CCT GGG AAA GGA CCT A | 51 |
| Var 2_MTA | AGC CTT GCG GTA CGG TTA GTG TTT CAT ATA AAT TTT TAT AAA TTT TAT TAT TTT TAA TAA ATA ATA ACT CGG GAG ACT ATG AAA TAT TGT AC | 52 |
| Var 3a-2_MTA | AGC CTT GCG GTA CGG TTA GTG TTT CAT ATA CAT AAA GAT GTC ATC ATC AAC CAA GTG | 53 |
| Var 3b_MTA | AGC CTT GCG GTA CGG TTA GTG TTT CAT ATA AAT TTT TAT AAA TTT TAT TAT TTT TGT CAA CTC GCG AAA AAA ACA G | 54 |
| Var 4a_MTA | AGC CTT GCG GTA CGG TTA GTG TTT CAT ATA AAT TTT TAT AAA TTA ATG ATG GCT TCC AAA TAG AAG TAC | 55 |
| Var 4b_MTA | AGC CTT GCG GTA CGG TTA GTG TTT CAT ATA AAT TTG ACA GAA AAA TAA TTC TGT GGG ATC A | 56 |
| Var 4b_MTA | AGC CTT GCG GTA CGG TTA GTG TTT CAT ATA AAT TTG ACA GAA AAA TAA TTC TGT GGG ATC A | 57 |
| Var 5a_MTA | AGC CTT GCG GTA CGG TTA GTG TTT CAT ATA ACT CAG TGA AAA AAT CAG TCT CAA GTA A | 58 |
| ALK MTA_3 | CCA CCG CCT TCA AGT TTA ACG ACA CAT ATA AAT TTT TAT AAA TTT TAT TAT TTT TAA TAA ATA ATA TTT GCC ATC ATT TTG GAG AGG ATT GA | 59 |
| RT Primers | | |
| EML4_ALK RT | TTG CTC AGC TTG TAC T | 60 |
| ALK pan RT | TGA TGT TGC CAG CAC | 61 |
| EML4 wt RT | GAT CGC ACC AGT GCA | 62 |

TABLE 1-continued

EML4-ALK Panel.

| Primer | Sequence | SEQ ID NO: |
|---|---|---|
| Var 5b RT | AAG CCT CCC TGG ATC | 63 |
| Var ALK RT | ACA AGT GGA CCA TAT TCT | 64 |

Synthetic PCR Primers

| Primer | Sequence | SEQ ID NO: |
|---|---|---|
| S6x | AGC CTT GCG GTA CGG TTA GTG TTT C | 65 |
| S12y | ACC TCG CTG GTA GAC CTC GTC TAA C | 66 |
| S2x | CCA CCG CCT TCA AGT TTA ACG ACA C | 67 |
| S0x | TTG CAC CGC ACC ACA TAC TAG TAC G | 68 |
| S6x | AGC CTT GCG GTA CGG TTA GTG TTT C | 69 |
| S2x | CCA CCG CCT TCA AGT TTA ACG ACA C | 70 |
| S0x | TTG CAC CGC ACC ACA TAC TAG TAC G | 71 |

Target-specific sequences are not underlined.
Names indicate the target variation.

TABLE 2

Reverse Transcriptase Reaction Reagent Composition

| Reagent Name | Stock | [Final] | per run (ul) |
|---|---|---|---|
| 5x Reverse Transcription Buffer | 5x | 1x | 4 |
| dNTP Mix | 10 mM | 500 mM | 1 |
| DTT | 100 mM | 5 mM | 1 |
| Reverse Primer Mix | 1 uM | 50 nM | 2 |
| SuperScript III (Enzyme) | 200 U/ul | 20 U/ul | 0.1 |
| Template | | | 5 |
| H2O | | | 6.9 |
| | | Total | 20 |

TABLE 3

PCR Reaction Composition

| Reagent Name | Stock | [Final] | per run (ul) |
|---|---|---|---|
| 10x FastStart (20 mM MgCl2) | 10x | 1x | 2.5 |
| MgCl2 | 25 mM | 2 mM | 4 |
| dNTPs | 10 mM | 0.4 mM | 1 |
| FastStart (enzyme) | 5 U/ul | 2 U | 0.6 |
| Primner Mix | 12.5x | 1x | 2 |
| Dna2BΔC (undil) | 25x | 0.25x | 0.25 |

TABLE 3-continued

PCR Reaction Composition

| Reagent Name | Stock | [Final] | per run (ul) |
|---|---|---|---|
| Template | | | 4 |
| H2O | | | 10.65 |
| | | Total | 25 |

TABLE 4

Thermocycling Conditions

| 1046 K | EW_Speed_2_62C/ 4MTA | Temperature | Time |
|---|---|---|---|
| Intial Denaturation | 1x | 96 C. | 600 sec |
| MTA Cycling | 4x | 62 C. | 25 sec |
| | | 72 C. | 25 sec |
| | | 96 C. | 5 sec |
| Pre-CE Cycling | 18x | 66 C. | 15 sec |
| | | 72 C. | 25 sec |
| | | 96 C. | 5 sec |
| PCR-CE Cycling | 19x | 66 C. | 90 sec |
| | | 72 C. | 140 sec |
| | | 96 C. | 10 sec |
| CE Sampling | 10x | 10 separations 22, 24 . . . 40 | |
| Separation Time | | 340 sec | |
| Total Run Time | | 2 hrs 20 min 58 sec | |

---

The invention claimed is:

1. A method for producing a discretely sized surrogate marker indicative of the presence and/or quantity of each of a plurality of DNA and RNA target nucleic acid molecules present in a nucleic acid sample, the method comprising:
   a) providing a nucleic acid sample comprising target DNA and target RNA nucleic acid molecules;
   b) hybridizing a plurality of different reverse-transcription primers to the nucleic acid sample comprising target DNA and target RNA molecules of step (a), wherein each different reverse-transcription primer is specific for a different target RNA member of said plurality of target nucleic acid molecules;
   c) extending the hybridized reverse-transcription primers of step (b) with an enzyme comprising reverse-transcriptase activity to produce a mixture comprising a population of cDNA molecules corresponding to the population of target RNA molecules hybridized in step (b), wherein the cDNA molecules corresponding to any given target RNA can differ in size;
   d) hybridizing the nucleic acids existing in said mixture after step (c) with a plurality of different single-stranded expander oligonucleotides to produce a plurality of expander oligonucleotide:DNA hybrid molecules, wherein each said expander oligonucleotide (i) corresponds to one DNA or RNA member of the plurality of DNA and RNA target nucleic acid molecules, (ii) comprises a replica sequence that is substantially identical to a mirrored sequence within its corresponding target nucleic acid molecule, wherein, when the target nucleic acid molecule is an RNA molecule, said mirrored sequence is located closer to the 5'-end of said target RNA molecule than the sequence to which the reverse-transcription primers of step (b) hybridizes, and wherein T is substituted for U in the replica sequence;
   e) extending the 3' end of the expander oligonucleotide strand in each of the plurality of expander oligonucleotide:DNA hybrid molecules produced in step (d) using a template-dependent polymerase enzyme, the extension producing in the same reaction, for each target DNA and RNA nucleic acid molecule, a surrogate marker for the presence of each of the plurality of DNA and RNA target nucleic acid molecules present in the nucleic acid sample, wherein either: (i) each surrogate marker is of a different characteristic size relative to surrogate markers for other target nucleic acids; or amplification products of respective surrogate markers are of different characteristic sizes relative to other surrogate markers or amplification products thereof; and
   f) amplifying at least a portion of the plurality of extended expander oligonucleotides by PCR amplification using a plurality of amplification primer pairs, thereby generating a plurality of extended expander oligonucleotide amplicons, wherein each said amplification primer pair comprises a forward amplification primer and a reverse amplification primer, wherein each said amplicon generated has a different length, and wherein each said amplicon generated provides a surrogate marker amplicon indicative of the presence and/or amount of one of said plurality of target nucleic acid molecules present in the nucleic acid sample.

2. The method of claim 1, wherein said plurality of target nucleic acid molecules comprises target RNAs of different classes.

3. The method of claim 2, wherein said target RNAs of different classes include two or more of mRNA, microRNA, siRNA, or hnRNA.

4. The method of claim 1, wherein each said expander oligonucleotide further comprises a forward primer sequence 5' of the replica sequence of the expander oligonucleotide.

5. The method of claim 1, wherein each said expander oligonucleotide further comprises a spacer sequence, wherein the spacer sequence is immediately 5' of the replica sequence of the expander oligonucleotide that is substantially identical to the mirrored sequence within the corresponding target nucleic acid molecule.

6. The method of claim 5, wherein said spacer sequence within each member of the plurality of expander oligonucleotides is of a different, discrete length than said spacer sequence in all other members of said plurality of expander oligonucleotides.

7. The method of claim 1, wherein said nucleic acid sample comprises partially, substantially randomly degraded target nucleic acids.

8. The method of claim 1 wherein each of the plurality of forward amplification primers used for amplification comprises a common 5' tag sequence.

9. The method of claim 1, wherein the plurality of forward amplification primers used for amplification are not all of the same length.

10. The method of claim 1, wherein the plurality of reverse amplification primers used for amplification are not all of the same length.

* * * * *